United States Patent [19]
Anderson et al.

[11] Patent Number: 5,994,104
[45] Date of Patent: Nov. 30, 1999

[54] INTERLEUKIN-12 FUSION PROTEIN

[75] Inventors: Robert James Anderson; Hugh Grant Prentice; Ian Duncan MacDonald, all of London, United Kingdom

[73] Assignee: Royal Free Hospital School Of Medicine, London, United Kingdom

[21] Appl. No.: 08/751,767

[22] Filed: Nov. 8, 1996

[51] Int. Cl.$^6$ .............................. C12N 15/19; C07K 14/54
[52] U.S. Cl. .................. 435/69.52; 435/69.5; 435/69.51; 435/69.7; 435/252.3; 435/320.1; 435/325; 530/351; 536/23.4; 536/23.5; 424/85.2; 930/141
[58] Field of Search .............................. 435/69.52, 69.7, 435/320.1, 252.3, 325; 536/23.5; 530/351; 424/85.2

[56] References Cited

U.S. PATENT DOCUMENTS

| | | | |
|---|---|---|---|
| 5,457,038 | 10/1995 | Trinchieri et al. | 435/69.52 |
| 5,635,599 | 6/1997 | Pastan et al. | 530/351 |
| 5,648,467 | 7/1997 | Trinchieri et al. | 530/351 |
| 5,650,492 | 7/1997 | Gately et al. | 530/351 |
| 5,705,484 | 1/1998 | Thomason | 514/12 |

FOREIGN PATENT DOCUMENTS

| | | |
|---|---|---|
| 0 640 689 A2 | 3/1995 | European Pat. Off. . |
| WO 96/24676 | 8/1996 | WIPO . |

OTHER PUBLICATIONS

Huston et al. PNAS USA vol. 85, pp. 5879–5883 (Aug. 1988).

R.J. Anderson et al. "Adeno–associated virus mediated . . . " Experimental Haematology 23, 939 (Abstract).

C.M. Bacon et al. "Interleuken 12 (IL–12) induces tyrosine . . . " J. Ex. Med 181, pp. 399–404.

C.M. Bacon et al. "Interleukin 12 induces tyrosine . . . " Proc. Natl. Acad. Sci. USA, 92, pp. 7307–7311.

M.J. Brunda et al. "Antitumor and antimetastatic activity . . . " J. Ex. Med 178, pp. 1223–1230.

J. Chehimi et al. "Natural killer (NK) cell stimulatory factor . . . " J. Ex. Med 175, pp. 789–796.

D'Andrea et al. "Production of natural killer cell . . . " J. Ex. Med 176, pp. 1387–1398.

Freeman et al. J. Immunol., vol. 143, No. 8 (1989), pp. 2714–2722.

M.K. Gately et al. "Regulation of human lymphocyte proliferation . . . " J. Immunol. 147, pp. 874–882.

R.T. Gazzinelli et al. "Interleukin 12 is required for the T–lymphocyte–independent . . . " Proc. Natl. Acad. Sci. USA 90, pp. 6115–6119.

U. Gubler et al. Coexpression of two distinct genes is required . . . Proc. Natl Acad. Sci, USA, 88, pp. 4143–4147.

L. Hatam et al. "Flow cytometric analysis . . . " Cytometry 16, pp. 59–68.

M. Kobayashi et al. "Identification and purification of natural killer . . . " J. Ex. Med 170, pp. 827–845.

M. Kubin et al. Interleukin 12 synergizes with B7/CD28 . . . J. Ex. Med 180, pp. 211–222.

R. Manetti et al. "Natural killer cell stimulatory factor . . . " J. Ex. Med 177, pp. 1199–1204.

F. Mattner et al. "The interleukin–12 subunit p.40 . . . " Eur. J. Immunol. 23, pp. 2202–2208.

J. Mu et al. "Administration of recombinant interleukin 12 . . . " Cancer Res. 55, pp. 4404–4408.

E.E. Murphy et al. "B7 and Interleukin 12 cooperate . . . " J. Ex. Med 180, pp. 223–231.

T.L. Murphy et al. "Regulation of interleukin 12 p.40 . . . " Mol Cell Biol. 15, pp. 5258–5267.

C.L. Nastala et al. "Recombinant IL–12 administration induces . . . " J. Immunol. 153, pp. 1697–1706.

P. Scott. "IL–12: initiation cytokine for cell–mediated . . . " Science, 260, pp. 496–497.

A.S. Stern et al. "Purification to homogeneity and partial . . . ", Natl. Acad. Sci. USA, 87, pp. 6808–6812.

M. Sykes, et al. "Interleukin–12 inhibits . . . " Blood, 86, pp. 2429–2438.

H. Tahara et al. "Fibroblasts genetically engineered . . . " Cancer Res. 54, pp. 182–189.

H. Tahara et al. "Effective eradication of established , , ," J. Immunol. 154, pp. 6466–6474.

S.F. Wolf et al. "Cloning of cDNA for natural killer cell stimulatory . . . " J. Immunol., 146, pp. 3074–3081.

L. Zitvogel et al. "Construction and characterization of retroviral . . . " Gene Ther. 5, pp. 1493–1506.

J.J. Zou et al. "Structure–function analysis . . . " J. Biol. Chem., 270, pp. 5864–5871.

Freeman et al. Science 262 (5135) (1993), pp. 909–911.

Azuma et al. Nature 366 (6450), (1993), pp. 76–79.

Couglin et al, Cancer Research 55, (1995), pp. 4980–4987.

Curtis et al. P.N.A.S. 88, (1991), pp. 5809–5813.

Zhao et al. Stem Cells 12, (1994), pp. 339–347.

Wang et al. Experimental Haematology, vol. 24, No. 9 (Aug. 24 1996): abstract from a presentation at the 25th Annual Meeting of the Intl Soc. For Exp. Haematology (Aug. 23–27, 1996) New York.

Anderson et al. Abstract from a presentation at the conference in New York, Nov. 9–12, 1996 +poster details.

Anderson et al. Abstract from a presentation at the 2nd Euro. Haematology Assoc., Paris, France May 29–Jun. 1, 1996.

*Primary Examiner*—Garnette D. Draper
*Attorney, Agent, or Firm*—Nixon & Vanderhye, P.C.

[57] ABSTRACT

This invention relates to Interleukin-12 fusion proteins and nucleic acid constructs encoding them, and to the use of such fusion proteins and constructs in tumour therapy, especially therapy of leukaemia. More particularly it relates to carrying out such therapy by means of cell therapy.

15 Claims, 24 Drawing Sheets

cDNA AND ENCODED AMINO ACID SEQUENCE OF HUMAN p35

```
GAATTCCCAG AAAGCAAGAG ACCAGAGTCC CGGGAAAGTC CTGCCGCGCC TCGGGACAAT      60
TATAAAAATG TGGCCCCCTG GGTCAGCCTC CCAGCCACCG CCCTCACCTG CCGCGGCCAC     120
AGGTCTGCAT CCAGCGGCTC GCCCTGTGTC CCTGCAGTGC CGGCTCAGC ATG TGT        175
                                                      Met Cys
                                                       1
```

| Codons | Amino acids | Pos |
|---|---|---|
| CCA GCG CGC AGC CTC CTC CTT GTG GCT ACC CTG GTC CTC CTG GAC CAC | Pro Ala Arg Ser Leu Leu Leu Val Ala Thr Leu Val Leu Leu Asp His | 223 |
|  | 5            10            15 |  |
| CTC AGT TTG GCC AGA AAC CTC CCC GTG GCC ACT CCA GAC CCA GGA ATG | Leu Ser Leu Ala Arg Asn Leu Pro Val Ala Thr Pro Asp Pro Gly Met | 271 |
|  | 20            25            30 |  |
| TTC CCA TGC CTT CAC CAC TCC CAA AAC CTG CTG AGG GCC GTC AGC AAC | Phe Pro Cys Leu His His Ser Gln Asn Leu Leu Arg Ala Val Ser Asn | 319 |
|  | 35            40            45            50 |  |
| ATG CTC CAG AAG GCC AGA CAA ACT CTA GAA TTT TAC CCT TGC ACT TCT | Met Leu Gln Lys Ala Arg Gln Thr Leu Glu Phe Tyr Pro Cys Thr Ser | 367 |
|  | 55            60            65 |  |
| GAA GAG ATT GAT CAT GAA GAT ATC ACA AAA GAT AAA ACC AGC ACA GTG | Glu Glu Ile Asp His Glu Asp Ile Thr Lys Asp Lys Thr Ser Thr Val | 415 |
|  | 70            75            80 |  |
| GAG GCC TGT TTA CCA TTG GAA TTA ACC AAG AAT GAG AGT TGC CTA AAT | Glu Ala Cys Leu Pro Leu Glu Leu Thr Lys Asn Glu Ser Cys Leu Asn | 463 |
|  | 85            90            95 |  |
| TCC AGA GAG ACC TCT TTC ATA ACT AAT GGG AGT TGC CTG GCC TCC AGA | Ser Arg Glu Thr Ser Phe Ile Thr Asn Gly Ser Cys Leu Ala Ser Arg | 511 |
|  | 100            105            110 |  |
| AAG ACC TCT TTT ATG ATG GCC CTG TGC CTT AGT AGT ATT TAT GAA GAC | Lys Thr Ser Phe Met Met Ala Leu Cys Leu Ser Ser Ile Tyr Glu Asp | 559 |
|  | 115            120            125            130 |  |
| TTG AAG ATG TAC CAG GTG GAG TTC AAG ACC ATG AAT GCA AAG CTT CTG | Leu Lys Met Tyr Gln Val Glu Phe Lys Thr Met Asn Ala Lys Leu Leu | 607 |
|  | 135            140            145 |  |
| ATG GAT CCT AAG AGG CAG ATC TTT CTA GAT CAA AAC ATG CTG GCA GTT | Met Asp Pro Lys Arg Gln Ile Phe Leu Asp Gln Asn Met Leu Ala Val | 655 |
|  | 150            155            160 |  |
| ATT GAT GAG CTG ATG CAG GCC CTG AAT TTC AAC AGT GAG ACT GTG CCA | Ile Asp Glu Leu Met Gln Ala Leu Asn Phe Asn Ser Glu Thr Val Pro | 703 |
|  | 165            170            175 |  |
| CAA AAA TCC TCC CTT GAA GAA CCG GAT TTT TAT AAA ACT AAA ATC AAG | Gln Lys Ser Ser Leu Glu Glu Pro Asp Phe Tyr Lys Thr Lys Ile Lys | 751 |
|  | 180            185            190 |  |
| CTC TGC ATA CTT CTT CAT GCT TTC AGA ATT CGG GCA GTG ACT ATT GAC | Leu Cys Ile Leu Leu His Ala Phe Arg Ile Arg Ala Val Thr Ile Asp | 799 |
|  | 195            200            205            210 |  |
| AGA GTG ACG AGC TAT CTG AAT GCT TCC TAA AAAGCGAGGT CCCTCCAAAC | Arg Val Thr Ser Tyr Leu Asn Ala Ser * | 849 |
|  | 215            220 |  |

```
CGTTGTCATT TTTATAAAAC TTTGAAATGA GGAAACTTTG ATAGGATGTG GATTAAGAAC    909
TAGGGAGGGG GAAAGAAGGA TGGGACTATT ACATCCACAT GATACCTCTG ATCAAGTATT    969
TTTGACATTT ACTGTGGATA AATTGTTTTT AAGTTTTCAT GAATGAATTG CTAAGAA      1026
```

Fig. 9.

cDNA AND ENCODED AMINO ACID SEQUENCE OF HUMAN p40

```
CTGTTTCAGG GCCATTGGAC TCTCCGTCCT GCCCAGAGCA AG ATG TGT CAC CAG         54
                                                Met Cys His Gln
                                                 1

CAG TTG GTC ATC TCT TGG TTT TCC CTG GTT TTT CTG GCA TCT CCC CTC       102
Gln Leu Val Ile Ser Trp Phe Ser Leu Val Phe Leu Ala Ser Pro Leu
 5               10                  15                  20

GTG GCC ATA TGG GAA CTG AAG AAA GAT GTT TAT GTC GTA GAA TTG GAT       150
Val Ala Ile Trp Glu Leu Lys Lys Asp Val Tyr Val Val Glu Leu Asp
                 25                  30                  35

TGG TAT CCG GAT GCC CCT GGA GAA ATG GTG GTC CTC ACC TGT GAC ACC       198
Trp Tyr Pro Asp Ala Pro Gly Glu Met Val Val Leu Thr Cys Asp Thr
             40                  45                  50

CCT GAA GAA GAT GGT ATC ACC TGG ACC TTG GAC CAG AGC AGT GAG GTC       246
Pro Glu Glu Asp Gly Ile Thr Trp Thr Leu Asp Gln Ser Ser Glu Val
         55                  60                  65

TTA GGC TCT GGC AAA ACC CTG ACC ATC CAA GTC AAA GAG TTT GGA GAT       294
Leu Gly Ser Gly Lys Thr Leu Thr Ile Gln Val Lys Glu Phe Gly Asp
     70                  75                  80

GCT GGC CAG TAC ACC TGT CAC AAA GGA GGC GAG GTT CTA AGC CAT TCG       342
Ala Gly Gln Tyr Thr Cys His Lys Gly Gly Glu Val Leu Ser His Ser
 85                  90                  95                 100

CTC CTG CTG CTT CAC AAA AAG GAA GAT GGA ATT TGG TCC ACT GAT ATT       390
Leu Leu Leu Leu His Lys Lys Glu Asp Gly Ile Trp Ser Thr Asp Ile
                105                 110                 115

TTA AAG GAC CAG AAA GAA CCC AAA AAT AAG ACC TTT CTA AGA TGC GAG       438
Leu Lys Asp Gln Lys Glu Pro Lys Asn Lys Thr Phe Leu Arg Cys Glu
            120                 125                 130

GCC AAG AAT TAT TCT GGA CGT TTC ACC TGC TGG TGG CTG ACG ACA ATC       486
Ala Lys Asn Tyr Ser Gly Arg Phe Thr Cys Trp Trp Leu Thr Thr Ile
        135                 140                 145

AGT ACT GAT TTG ACA TTC AGT GTC AAA AGC AGC AGA GGC TCT TCT GAC       534
Ser Thr Asp Leu Thr Phe Ser Val Lys Ser Ser Arg Gly Ser Ser Asp
    150                 155                 160

CCC CAA GGG GTG ACG TGC GGA GCT GCT ACA CTC TCT GCA GAG AGA GTC       582
Pro Gln Gly Val Thr Cys Gly Ala Ala Thr Leu Ser Ala Glu Arg Val
165                 170                 175                 180

AGA GGG GAC AAC AAG GAG TAT GAG TAC TCA GTG GAG TGC CAG GAG GAC       630
Arg Gly Asp Asn Lys Glu Tyr Glu Tyr Ser Val Glu Cys Gln Glu Asp
                185                 190                 195

AGT GCC TGC CCA GCT GCT GAG GAG AGT CTG CCC ATT GAG GTC ATG GTG       678
Ser Ala Cys Pro Ala Ala Glu Glu Ser Leu Pro Ile Glu Val Met Val
            200                 205                 210

GAT GCC GTT CAC AAG CTC AAG TAT GAA AAC TAC ACC AGC AGC TTC TTC       726
Asp Ala Val His Lys Leu Lys Tyr Glu Asn Tyr Thr Ser Ser Phe Phe
        215                 220                 225

ATC AGG GAC ATC ATC AAA CCT GAC CCA CCC AAG AAC TTG CAG CTG AAG       774
Ile Arg Asp Ile Ile Lys Pro Asp Pro Pro Lys Asn Leu Gln Leu Lys
    230                 235                 240

CCA TTA AAG AAT TCT CGG CAG GTG GAG GTC AGC TGG GAG TAC CCT GAC       822
Pro Leu Lys Asn Ser Arg Gln Val Glu Val Ser Trp Glu Tyr Pro Asp
```

Fig.9 (Cont).

```
        245                     250                     255                     260
ACC TGG AGT ACT CCA CAT TCC TAC TTC TCC CTG ACA TTC TGC GTT CAG            870
Thr Trp Ser Thr Pro His Ser Tyr Phe Ser Leu Thr Phe Cys Val Gln
                265                     270                     275

GTC CAG GGC AAG AGC AAG AGA GAA AAG AAA GAT AGA GTC TTC ACG GAC            918
Val Gln Gly Lys Ser Lys Arg Glu Lys Lys Asp Arg Val Phe Thr Asp
            280                     285                     290

AAG ACC TCA GCC ACG GTC ATC TGC CGC AAA AAT GCC AGC ATT AGC GTG            966
Lys Thr Ser Ala Thr Val Ile Cys Arg Lys Asn Ala Ser Ile Ser Val
            295                     300                     305

CGG GCC CAG GAC CGC TAC TAT AGC TCA TCT TGG AGC GAA TGG GCA TCT           1014
Arg Ala Gln Asp Arg Tyr Tyr Ser Ser Ser Trp Ser Glu Trp Ala Ser
            310                     315                     320

GTG CCC TGC AGT TAG GTTCTGATCC AGGATGAAAA TTTGGAGGAA AAGTGGAAGA           1069
Val Pro Cys Ser  *
325

TATTAAGCAA AATGTTTAAA GACACAACGG AATAGACCCA AAAAGATAAT TTCTATCTGA         1129
TTTGCTTTAA AACGTTTTTT TAGGATCACA ATGATATCTT TGCTGTATTT GTATAGTTAG         1189
ATGCTAAATG CTCATTGAAA CAATCAGCTA ATTTATGTAT AGATTTTCCA GCTCTCAAGT         1249
TGCCATGGGC CTTCATGCTA TTTAAATATT TAAGTAATTT ATGTATTTAT TAGTATATTA         1309
CTGTTATTTA ACGTTTGTCT GCCAGGATGT ATGGAATGTT TCATACTCTT ATGACCTGAT         1369
CCATCAGGAT CAGTCCCTAT TATGCAAAAT                                          1399
```

Fig.10.

cDNA AND ENCODED AMINO ACID SEQUENCE OF HUMAN B7.1

```
CCAAAGAAAA AGTGATTTGT CATTGCTTTA TAGACTGTAA GAAGAGAACA TCTCAGAAGT      60
GGAGTCTTAC CCTGAAATCA AAGGATTTAA AGAAAAAGTG GAATTTTTCT TCAGCAAGCT     120
GTGAAACTAA ATCCACAACC TTTGGAGACC CAGGAACACC CTCCAATCTC TGTGTGTTTT     180
GTAAACATCA CTGGAGGGTC TTCTACGTGA GCAATGGAT TGTCATCAGC CCTGCCTGTT      240
TTGCACCTGG GAAGTGCCCT GGTCTTACTT GGGTCCAAAT TGTTGGCTTT CACTTTTGAC     300
CCTAAGCATC TGAAGCC ATG GGC CAC ACA CGG AGG CAG GGA ACA TCA CCA        350
                   Met Gly His Thr Arg Arg Gln Gly Thr Ser Pro
                    1               5                       10

TCC AAG TGT CCA TAC CTC AAT TTC TTT CAG CTC TTG GTG CTG GCT GGT       398
Ser Lys Cys Pro Tyr Leu Asn Phe Phe Gln Leu Leu Val Leu Ala Gly
            15                  20                  25

CTT TCT CAC TTC TGT TCA GGT GTT ATC CAC GTG ACC AAG GAA GTG AAA       446
Leu Ser His Phe Cys Ser Gly Val Ile His Val Thr Lys Glu Val Lys
        30                  35                  40

GAA GTG GCA ACG CTG TCC TGT GGT CAC AAT GTT TCT GTT GAA GAG CTG       494
Glu Val Ala Thr Leu Ser Cys Gly His Asn Val Ser Val Glu Glu Leu
    45                  50                  55

GCA CAA ACT CGC ATC TAC TGG CAA AAG GAG AAG AAA ATG GTG CTG ACT       542
Ala Gln Thr Arg Ile Tyr Trp Gln Lys Glu Lys Lys Met Val Leu Thr
60                  65                  70                  75

ATG ATG TCT GGG GAC ATG AAT ATA TGG CCC GAG TAC AAG AAC CGG ACC       590
Met Met Ser Gly Asp Met Asn Ile Trp Pro Glu Tyr Lys Asn Arg Thr
                80                  85                  90

ATC TTT GAT ATC ACT AAT AAC CTC TCC ATT GTG ATC CTG GCT CTG CGC       638
Ile Phe Asp Ile Thr Asn Asn Leu Ser Ile Val Ile Leu Ala Leu Arg
            95                  100                 105

CCA TCT GAC GAG GGC ACA TAC GAG TGT GTT GTT CTG AAG TAT GAA AAA       686
Pro Ser Asp Glu Gly Thr Tyr Glu Cys Val Val Leu Lys Tyr Glu Lys
        110                 115                 120

GAC GCT TTC AAG CGG GAA CAC CTG GCT GAA GTG ACG TTA TCA GTC AAA       734
Asp Ala Phe Lys Arg Glu His Leu Ala Glu Val Thr Leu Ser Val Lys
    125                 130                 135

GCT GAC TTC CCT ACA CCT AGT ATA TCT GAC TTT GAA ATT CCA ACT TCT       782
Ala Asp Phe Pro Thr Pro Ser Ile Ser Asp Phe Glu Ile Pro Thr Ser
140                 145                 150                 155

AAT ATT AGA AGG ATA ATT TGC TCA ACC TCT GGA GGT TTT CCA GAG CCT       830
Asn Ile Arg Arg Ile Ile Cys Ser Thr Ser Gly Gly Phe Pro Glu Pro
                160                 165                 170

CAC CTC TCC TGG TTG GAA AAT GGA GAA GAA TTA AAT GCC ATC AAC ACA       878
His Leu Ser Trp Leu Glu Asn Gly Glu Glu Leu Asn Ala Ile Asn Thr
            175                 180                 185

ACA GTT TCC CAA GAT CCT GAA ACT GAG CTC TAT GCT GTT AGC AGC AAA       926
Thr Val Ser Gln Asp Pro Glu Thr Glu Leu Tyr Ala Val Ser Ser Lys
        190                 195                 200

CTG GAT TTC AAT ATG ACA ACC AAC CAC AGC TTC ATG TGT CTC ATC AAG       974
Leu Asp Phe Asn Met Thr Thr Asn His Ser Phe Met Cys Leu Ile Lys
    205                 210                 215

TAT GGA CAT TTA AGA GTG AAT CAG ACC TTC AAC TGG AAT ACA ACC AAG      1022
Tyr Gly His Leu Arg Val Asn Gln Thr Phe Asn Trp Asn Thr Thr Lys
220                 225                 230                 235

CAA GAG CAT TTT CCT GAT AAC CTG CTC CCA TCC TGG GCC ATT ACC TTA      1070
```

Fig.10 (Cont).

```
              Gln Glu His Phe Pro Asp Asn Leu Leu Pro Ser Trp Ala Ile Thr Leu
                              240                 245                 250
ATC TCA GTA AAT GGA ATT TTT GTG ATA TGC TGC CTG ACC TAC TGC TTT              1118
Ile Ser Val Asn Gly Ile Phe Val Ile Cys Cys Leu Thr Tyr Cys Phe
            255                 260                 265
GCC CCA AGA TGC AGA GAG AGA AGG AGG AAT GAG AGA TTG AGA AGG GAA              1166
Ala Pro Arg Cys Arg Glu Arg Arg Arg Asn Glu Arg Leu Arg Arg Glu
        270                 275                 280
AGT GTA CGC CCT GTA TAA CAGTGTCCGC AGAAGCAAGG GGCTGAAAAG                     1214
Ser Val Arg Pro Val  *
        285
ATCTGAAGGT AGCCTCCGTC ATCTCTTCTG GGATACATGG ATCGTGGGGA TCATGAGGCA            1274
TTCTTCCCTT AACAAATTTA AGCTGTTTTA CCCACTACCT CACCTTCTTA AAAACCTCTT            1334
TCAGATTAAG CTGAACAGTT ACAAGATGGC TGGCATCCCT CTCCTTTCTC CCCATATGCA            1394
ATTTGCTTAA TGTAACCTCT TCTTTTGCCA TGTTTCCATT CTGCCATCTT GAATTGTCTT            1454
GTCAGCCAAT TCATTATCTA TTAAACACTA ATTTGAG                                     1491
```

Fig. 11.

```
                                                                                                Ssp I
GCACTTTTCGGGGAAATGTGCGCGGGAACCCTGTATTTGTTATTTTTCTAAATACATTCAAATATGTATCCGCTCATGAGACAATAACCCTGATAAATGTTCAATATATTGAAAAGGA  120
CGTGAAAGCCCCTTTACACGCGCCCTTGGGACATAAACAAATAAAGATTTATAAGTTTATACATAGGCGAGTACTCTGTATTGGGACTATTTACGAAGTTATTATAACTTTTTCCT
Gly Thr Phe Arg Gly Asn Val Arg Gly Thr Pro Ile Cys Leu Phe Phe •  Ile His Ser Asn Met Tyr Pro Leu Met Arg Gln •  • Met Leu Gln • Tyr • Lys Arg
           Bsu36 I         Pvu II                                                                          Sph I
                                                                                                            Nsi I
AGAGTCCTGAGGCGGAAAGAACCAGCTGTGTGGAATGTGTCAGTTAGGGTGTGGAAAGTCCCCAGGCTCCCCAGGCAGAGGCAGAAGTATGCAAAGCATGCATCCAATTAGTCAGCAACCAG  240
TCTCAGGACTCCGCCTTTCTTGGTCGACACAGTTACACACCTTACACAGTCAATCCCACACCTTTCAGGGGTCCGAGGGTCGTCCGTCTTCATACGTTTCGTACGTAGTTAATCAGTCGTTGGTC
Lys Ser Pro Glu Ala Glu Arg Thr Ser Cys Gly Met Cys Val Ser • Gly Val Glu Ser Pro Gln Ala Pro Gln Ala Glu Val Cys Lys Ala Cys Ile Ser Gln Pro
                                                             Sph I
                                                             Nsi I
GTGTGTGAAAGTCCCCAGGCTCCCCAGCAGGCAGAAGCATGCAAAGCATGCATCCAATTAGTCAGCAACCATAGTCCCGCCCATCCCGCCCCTAACTCCGCCCAGTTC  360
CACACACTTTCAGGGGTCCGAGGGGTCGTCCGTCTTCGTACTTTCGTACGTAGGTTAATCAGTCGTTGGTATCAGGGATCAGGGCGGGTAGGGCGGGGATTGAGGCGGGTCAAG
Gly Val Glu Ser Pro Gln Ala Pro Gln Ala Glu Val Cys Lys Ala Cys Ile Ser Gln Pro • Ser Arg Pro • Leu Arg Pro Ser Arg Pro • Leu Arg Pro Val
         Nco I                                                    Bgl I                                    Stu I
                                                                                                           Avr II
CGGCCATTCTCCGCCCATGGCTGACTAATTTTTTTTATTTATTGCAGAGATTCCGGCCTCTGAGCTATTCCAGAAGTAGTGAGGAGGCTTTTTTGGAGGCCTAGGCTTTTG  480
GCGGGTAAGAGGCGGGTACCGACTGATTAAAAAAATAAATACGTCTCTAATAAGGTCTTCATCACTCCTCCGAAAAAACCTCCGGATCCGAAAAC
Pro Pro Ile Leu Arg Pro Met Ala Asp • Phe Phe Leu Phe Met Gln Arg Pro Arg Pro Pro Arg Pro Leu Ser Tyr Ser Arg Ser Ser Glu Glu Val Glu Glu Val Glu Ala Phe Leu Glu Ala • Ala Phe
```

```
Msl I
     ATGGGCGATGCCTGCTTGCCGAATATCATGTGGAAAATGGCCGCTTTTCTGGATTCATCGACTGTGTGGCCGGCTGGGTGTGGGGACCGCTATCAGGACATAGCGTTGGCTACCCGTGATA
     TACCGCTACGGACGAACGGCTTATAGTACCACCTTTTACCGGGCGAAAAGACCTAAGTAGCTGACACGGCCGACCCACACGGCCGGCGACCGCCTGGCGATAGTCCTGTATCGCAACGATGGGCACTAT     1200
     His Gly Asp Ala Cys Leu Pro Asn Ile Met Val Glu Asn Gly Arg Phe Ser Gly Arg Leu Gly Val Ala Asp Arg Tyr Gln Asp Ile Ala Leu Ala Thr Arg Asp

TTGCTGAAGAGCTTGGCCGGCGAATGGGCTGACCGCTTCCTCGTGCTTACGGTATCGCCGCTCCCGATTCGCAGGCGCATCGCCTTCTATCGCCTTCTTGACGAGTTCTTCTGAGCGGGAC
     AACGACTTCTCGAACCGCCGCCTTACCCGACTGGCGAAGGAGCACGAGAATGCCATAGCGGCGAGGGCTAAGCGTCGCGTAGCCGAAGATAGCGGAAGAACTGCTCAAGAAGACTCGCCCTG     1320
     Ile Ala Glu Leu Gly Glu Trp Ala Asp Arg Phe Leu Val Leu Tyr Gly Ile Ala Ala Pro Asp Ser Gln Arg Ile Ala Phe Tyr Arg Leu Leu Asp Glu Phe Phe • Ala Gly

TCTGGGGTTCGAAATGACCGACCAAGGACGCCCAACCTGCCATCACGAGATTTCGATTCCACCGCGCCTTCTATGAAAGGTTGGGCTTCGGAATCGTTTTCCGGGACGCCGGCTGGAT
     AGACCCCAAGCTTTACTGGCTGGTTCGCTGCGGGTTGGACGTAGTCTCTAAAGCTAAGGTGCTCTAAAGCTAAGGTGGGCGGAAGTACTTTCCAACCGAAGCCTTAGCACAAAAGGCCCTGCGGCCGACCTA     1440
     Leu Trp Gly Ser Lys • Pro Thr Gly Lys Arg Arg Pro Thr Cys His His Glu Ile Ser Ile Pro Pro Pro Pro Ser Met Lys Gly Trp Ala Ser Glu Ser Phe Ser Gly Thr Pro Ala Gly
                                                                     AvrII
     GATCCTCCAGCGCGGGATCTCATGCTGGAGTTCTTCGCCCCACCCTAGGGGAGGCTAACTGAAACACGGAAGGAGACAATACCGAAGGAACCCGCTATGACGGCAATAAAAGACA
     CTAGGAGGTCGCGCCCTAGAGTACGACCTCAAGAAGCGGGGATCCCCCTCCGATTGACTTTGTGCCTTCCTCGTGTTATGGCCTTCCTTGGGCGATACTGCCGTTATTTTCTGT     1560
     • Ser Ser Ser Ala Gly Ile Ser Cys Trp Ser Ser Ser Pro Thr Leu Gly Gly Gly • Leu Lys His Gly Arg Arg Gln Tyr Arg Lys Glu Pro Ala Leu • Arg Gln • Lys Asp

GAATAAAACGCACGGTTGGGTCGTTTGTTCATAAACGCGGGTTCGGTCCCAGGGGTTCGGTCCCAGGGCTGGCACTCTGTCGATACCCCACCGAGACCCATTGGGGCCAATACGCCCGCGTTTCTTCCTT
     CTTATTTTGCGTGCCACAACCCAGCACCAAGTATTTGCGCCCAAGCAAGCCAGGTCCCGACCGTGGAGACAGCTATGGGGTAACCCGGTTATGCGGGCGCAAAGAAGGAA     1680
     Arg Ile Lys Arg Thr Val Leu Gly Arg Leu Phe Ile Asn Ala Gly Phe Gly Pro Arg Ala Gly Thr Leu Ser Ile Pro His Arg Asp Pro Ile Gly Ala Asn Thr Pro Ala Phe Leu Pro

Bsu36 I
     TTCCCCACCCCACCCCCAAGTTCGGGTGAAGGCCCAGGGGCTCGCAGCAACGTCGGGGCGGCAACGTCGGGGCGGCCTGCCATAGCCTCAGGTTACTCAAGCCTCATATATACTTTAGATTGATTTAAACTTCA
     AAGGGGTGGGGTGGGGGTTCAAGCCCACTTCGGGTTGCAGCCCCGCGTCGGTTGCAGCCCCGCTGCAGCCCGTATCGGAGTCCAATGAGTATATGAAATCTAACTAAATTTGAAGT     1800
     Phe Pro His Pro Thr Pro Gln Val Arg Val Lys Ala Gln Gly Ser Gly Pro Thr Ser Gly Arg Gln Pro Gly Ala Leu Pro • Pro Gln Val Thr His Ile Tyr Phe Arg Leu Ile • Asn Phe
```

Fig.11 (Cont 3).

```
TTTTTAATTTAAAAGGATCTAGGTGAAGATCCTTTTTGATAATCTCATGACCAAATCCCTTAACGTGAGTTTCGTTCCACTGAGCGTCAGACCCGTAGAAAGATCAAAGGATCTTC
AAAAATTAAATTTTCCTAGATCCACTTCTAGGAAAACTATTAGAGTACTGGTTTTAGGGAAATTGCACTGAAAGCAAGGTGACTCGCAGTCGGGGCATCTTTTCTAGTTTCTAGAAG   1920
Ile Phe Asn Leu Lys Gly Ser Arg   Arg Ser Phe Leu Ile Ile Ser   Pro Lys Ser Leu Asn Val Ser Phe Arg Ser Thr Glu Arg Gln Thr Pro    Lys Arg Ser Lys Asp Leu

TTGAGATCCTTTTTTTCTGCGCGTAATCTGCTTGCAAACAAAAAACCACCGCTACCAGCGGTGGTTTGTTTGCCGGATCAAGAGCTACCAACTCTTTTTCCGAAGGTAACTGGCTT
AACTCTAGGAAAAAAAGAGCGCATTAGACGACGAACGTTTGTTTTTTTGGTGGCGATGGTCGCCACCAAACAAACGGCCTAGTTCTCGATGGTTGAGAAAAAGGCTTCCATTGACCGAA   2040
Leu Glu Ile Leu Phe Cys Ala   Ser Ala Ala Cys Lys Gln Lys Asn His Arg Tyr Gln Arg Trp Phe Val Cys Arg Ile Lys Ser Tyr Gln Leu Phe Arg Arg    Leu Ala

CAGCAGAGCGCAGATACCAAATACTGTCCTTCTAGTGTAGCCGTAGTTAGGCCACCACTTCAAGAACTCTGTAGCACCGCCTACATCCGCTCTGCTAATCCTGTTACCAGTGGCTGC
GTCGTCTCGCGTCTATGGTTTATGACAGGAAGATCACATCGGCATCAATCCGGTGGTGAAGTTCTTGAGACATCGTGGCGGATGTATGGAGCGAGACGATTAGGACAATGGTCACCGACG   2160
Ser Ala Glu Arg Arg Tyr Gln Ile Leu Ser Phe   Cys Ser Arg Ser   Ala Thr Thr Ser Arg Thr Leu   His Arg Leu His Thr Ser Leu Cys    Ser Cys Tyr Gln Trp Leu

TGCCAGTGCGGCGATAAGTCGTGTCTTACCGGGTTGGACTCAAGACGATAGTTACCGGATAAGGCGCAGCGGTCGGGCTGAACGGGGGGTTCGTGCACACAGCCCAGCTTGGAGCGAACGAC
ACGGTCACGCCGCTATTCAGCACACAGAATGGCCAACCTGAGTTCTGCTATCAATGCCTATTCCGCGTCGCCAGCCCGACTTGCCCCCCAAGCACGTGTCGGTGTCGAACCTCGCTTGCTG   2280
Leu Pro Val Ala Ile Ser Arg Val Leu Pro Gly Trp Thr Gln Asp Asp Ser Tyr Arg Ile Arg Arg Ser Gly Arg Ala Glu Arg Gly Val Arg Ala His Ser Pro Ala Trp Ser Glu Arg

CTACACCGAACTGAGATACCTACAGCGTGAGCTATGAGAAGCGCCACGCTTCCCGAAGGAGAAAAGCGGACTATCCGGTAAGCCCAGCCTTGCGCGTGTCCTCTCGCGTGTCCCT
GATGTGGCTTGACTCTATGGATGTCGCACTCGATACTCTTTCGCGAAGGGCTTCCCTCTTTTCGCCTGTCCATAGGCCATTCGGAGCCTGTCCTTCGGAATGCCATTCGCCGGGTCGGAACGCGCGCAGAGGA   2400
Pro Thr Pro Asn   Asp Thr Tyr Ser Val Ser Tyr Glu Lys Ala Pro Arg Phe Pro Lys Gly Arg Arg Thr Gly Ile Arg    Ala Ala Gly Ser Glu Gln Glu Ser Ala Arg Gly

GCTTCCAGGGGGAAACGCCTGGTATCTTTATAGTCCTGTCTGGGTTTCGCCACTCTGACTTGAGCGTCGATTTTGTGATGTCGTCAGGGGGGGAGCCTATGGAAAAACGCCAGCAA
CGAAGGTCCCCCTTTGCGGACCATAGAAATATCAGGACAGCCCAAAGCGGTGAGACTGAACTCGCAGCTAAAAACACTACGAGCAGTCCCCCGCCTCGATACCTTTTGCGGTCGTT   2520
Ser Phe Gln Gly Glu Thr Pro Gly Ile Phe Ile Val Leu Ser Gly Phe Ala Thr Ser Asp Leu Ser Val Asp Phe Cys Asp Ala Arg Gln Gly Gly Ala Tyr Gly Lys Thr Pro Ala
```

Fig.11 (Cont 4).

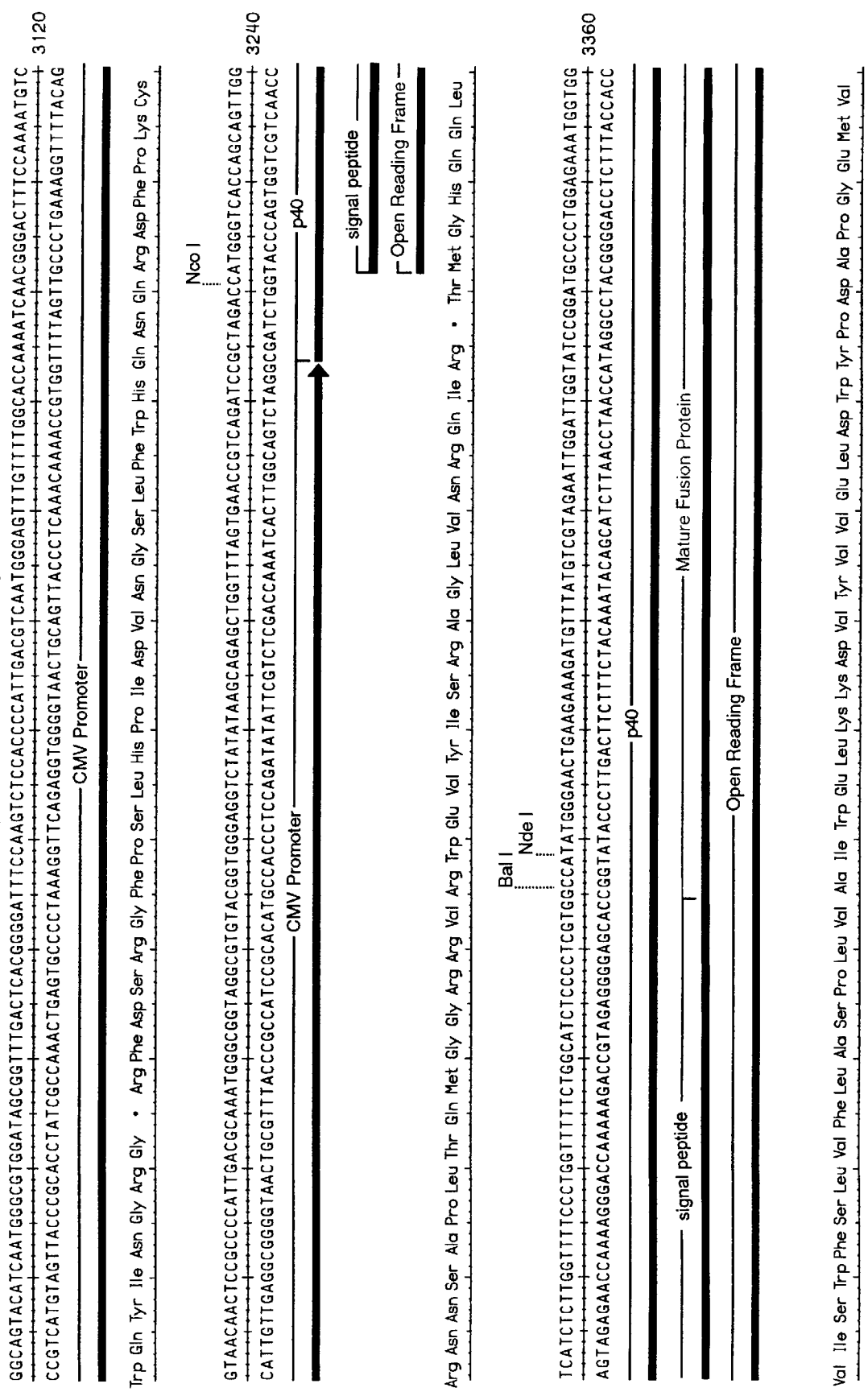
Fig. 11 (Cont 5).

Fig.11 (Cont 6).

```
                                                                    Bal I
                                                                    ......
TCCTCACCTGTGACACCCCTGAAGAAGATGGTATCACCTGGACCTTGGACCAGAGCAGTGAGGTCTTAGGCTCTGGCAAAACCCTGACCATCCAAGTCAAAGAGTTTGGAGATGCTGGCC
                                                                                                                        3480
AGGAGTGGACACTGTGGGGACTTCTTCTACCATAGTGGACCTGGAACCTGGAGACCGTGGTCTCGTCACTCGAGACCGTTTTGGGACTGTAGGTTCAGTTCTCAAACCTCTACGACCGG
——————————————————————— Mature Fusion Protein ———————————————————————
——————————————————————— Open Reading Frame ———————————————————————
——————————————————————— p40 ———————————————————————

Val Leu Thr Cys Asp Thr Pro Glu Glu Asp Gly Ile Thr Trp Thr Leu Asp Gln Ser Ser Glu Val Leu Gly Ser Gly Lys Thr Leu Thr Ile Gln Val Lys Glu Phe Gly Asp Ala Gly
AGTACACCTGTCACAAAGGAGGCGAGGTTCTAAGCCATTCGCTCTGCTTCACAAAAAGGAAGATGGAATTTGGTCCACTGATATTTAAAGGACCAGAAGAACCCAAAATAAGA
                                                                                                                    3600
TCATGTGGACAGTGTTTCCTCCGCTCCAAGATTCGGTAAGCGAGGAGGACGACGAAGTGTTTTCCTTCTACCTTAAACCAGGTGACTATAAAATTTCCTGGTCTCTTCTTGGGTTTTATTCT
——————————————————————— Mature Fusion Protein ———————————————————————
——————————————————————— Open Reading Frame ———————————————————————
——————————————————————— p40 ———————————————————————

Gln Tyr Thr Cys His Lys Gly Gly Glu Val Leu Ser His Ser Leu Leu Leu Leu His Lys Lys Glu Asp Gly Ile Trp Ser Thr Asp Ile Leu Lys Asp Gln Lys Glu Pro Lys Asn Lys
                                                      Sca I
                                                      ......
CCTTTCTAAGATGCGAGGCCAAGAATTATTCTGGACGTTTCACCTGCTGGTGCTGACGACAATCAGTACTGATTTGACATTCAGTGTCAAAAGCAGCAGGACGAGGCTCTTCTGACCCCCAAG
                                                                                                                         3720
GGAAAGATTCTACGCTCCGGTTCTTAATAAGACCTGCAAAGTGGACGACCACCGACTGCTGTTAGTCATGACTAAACTGTAAGTCACAGTTTTCGTCGTCTCCGAGAAGACTGGGGGTTC
——————————————————————— Mature Fusion Protein ———————————————————————
——————————————————————— Open Reading Frame ———————————————————————
——————————————————————— p40 ———————————————————————
```

Fig.11 (Cont 7).

Thr Phe Leu Arg Cys Glu Ala Lys Asn Tyr Ser Gly Arg Phe Thr Cys Trp Trp Leu Thr Thr Ile Ser Thr Asp Leu Thr Phe Ser Val Lys Ser Ser Arg Gly Ser Ser Asp Pro Gln

```
                       Pst I                                              Sca I                                   Pvu II
GGGTGACGTGCCGAGCTGCTACACTCTCTGCAGAGAGTCAGAGGGGACAACAAGGAGTATGAGTACTCAGTGGAGTGCCAGGAGACAGTGCCTGCCCAGCTGCTGAGGAGAGTCTGC    3840
CCCACTGCACGGCTCGACGATGTGAGAGACGTCTCTCAGTCTCCTCAGTCTCCCCTGTTGTTCCTCATATCATGAGTCACCTCACGGTCCTCCTGTCACGGACGGGTCGACGACTCCTCTCAGACG
                                                              ─── p40 ───
                                                         ─── Mature Fusion Protein ───
                                                         ─── Open Reading Frame ───
```

Gly Val Thr Cys Gly Ala Ala Thr Leu Ser Ala Glu Arg Val Arg Gly Asp Asn Lys Glu Arg Val Glu Cys Gln Glu Asp Ser Ala Cys Pro Ala Ala Glu Glu Ser Leu

```
                                                                                                                Pvu II
CCATTGAGGTCATGGTGGATGCCGTTCACAAGCTCAAGTATGAAAACTACACCAGCAGCTTCTTCATCAGGACATCATCAAACCTGACCCACCCAAGAACTTGCAGCTGAAGCCATTAA    3960
GGTAACTCCAGTACCACCTACGGCAAGTTCGAGTTCATACTTTTGATGGTCGTCGAAGAAGTAGTCCCTGTAGTAGTTTGGACTGGGTTCTTGAACGTCGACTTCGGTAATT
                                                              ─── p40 ───
                                                         ─── Mature Fusion Protein ───
                                                         ─── Open Reading Frame ───
```

Pro Ile Glu Val Met Val Asp Ala Val His Lys Leu Lys Tyr Glu Asn Tyr Thr Ser Ser Phe Phe Ile Arg Asp Ile Ile Lys Pro Asp Pro Pro Lys Asn Leu Gln Leu Lys Pro Leu

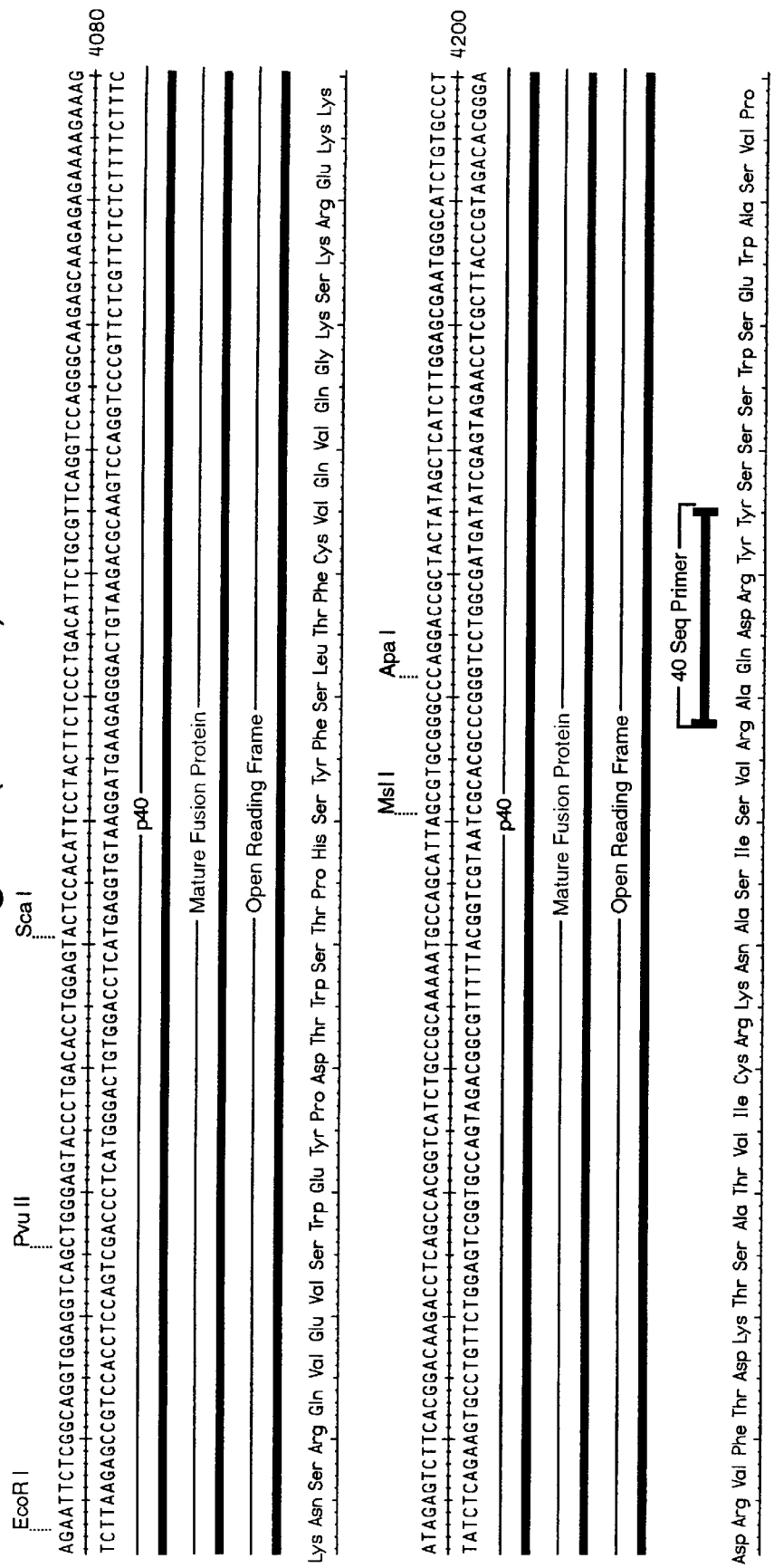
Fig. 11 (Cont 8).

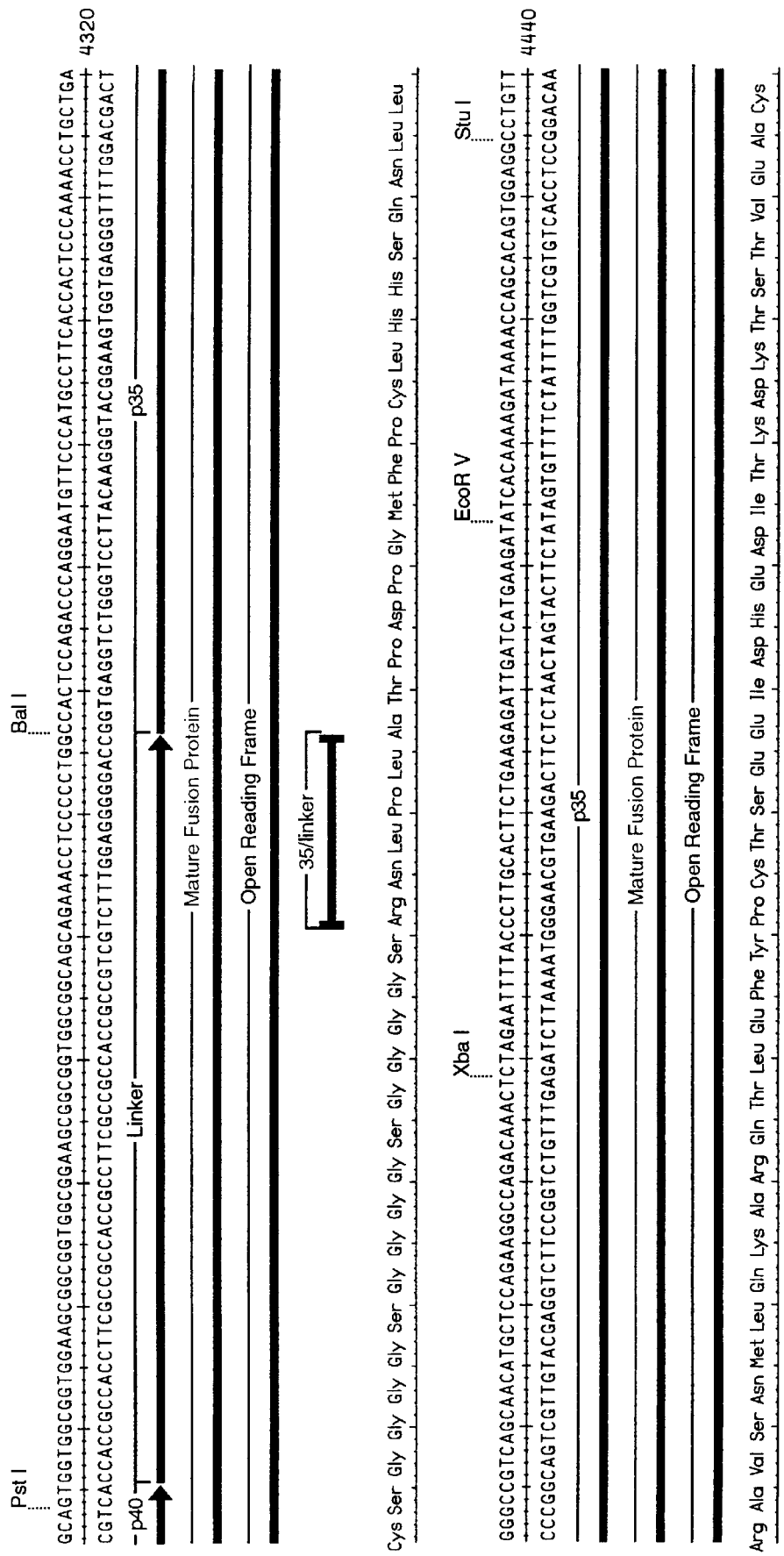
Fig.11 (Cont 9).

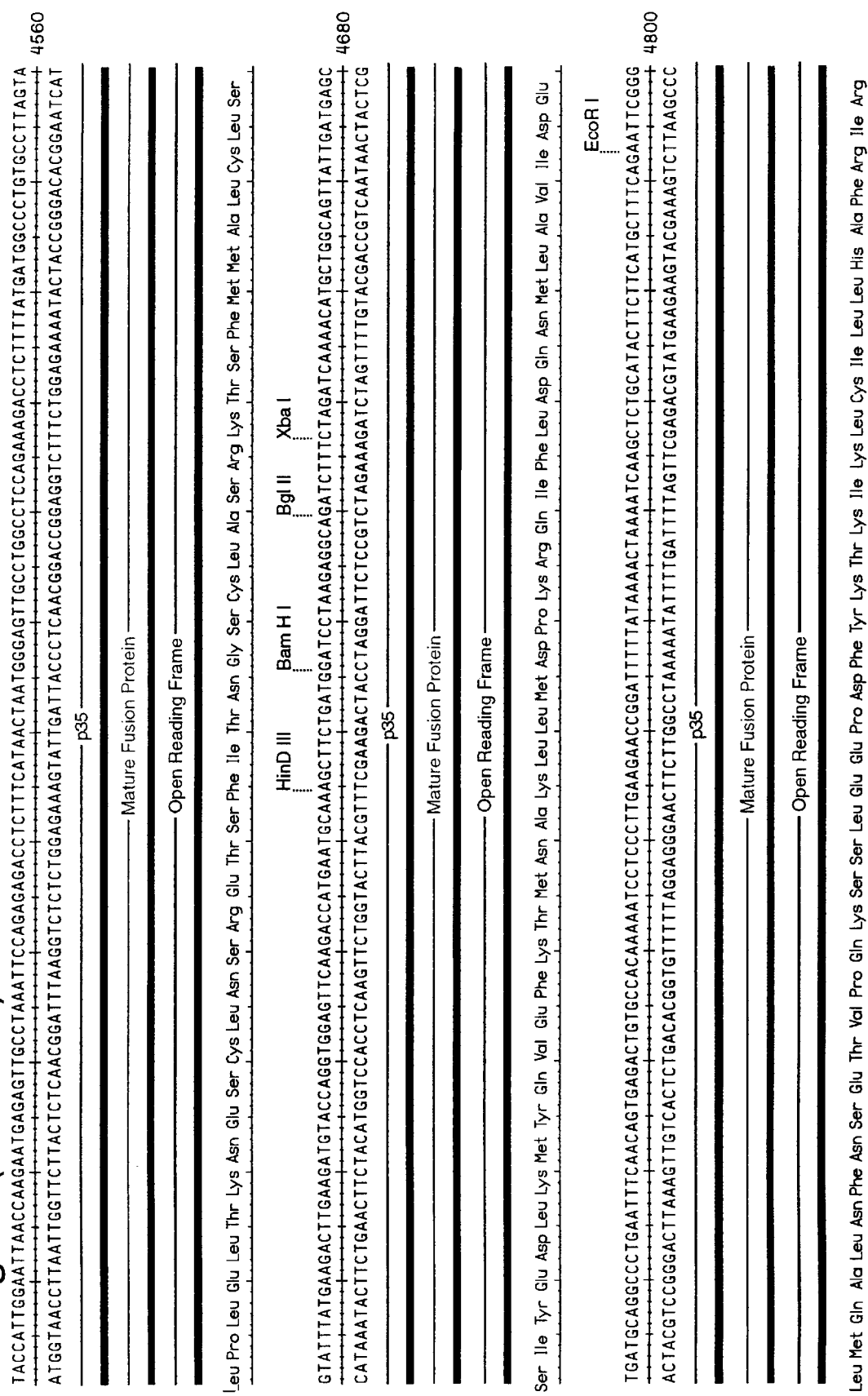
Fig. 11 (Cont 10).

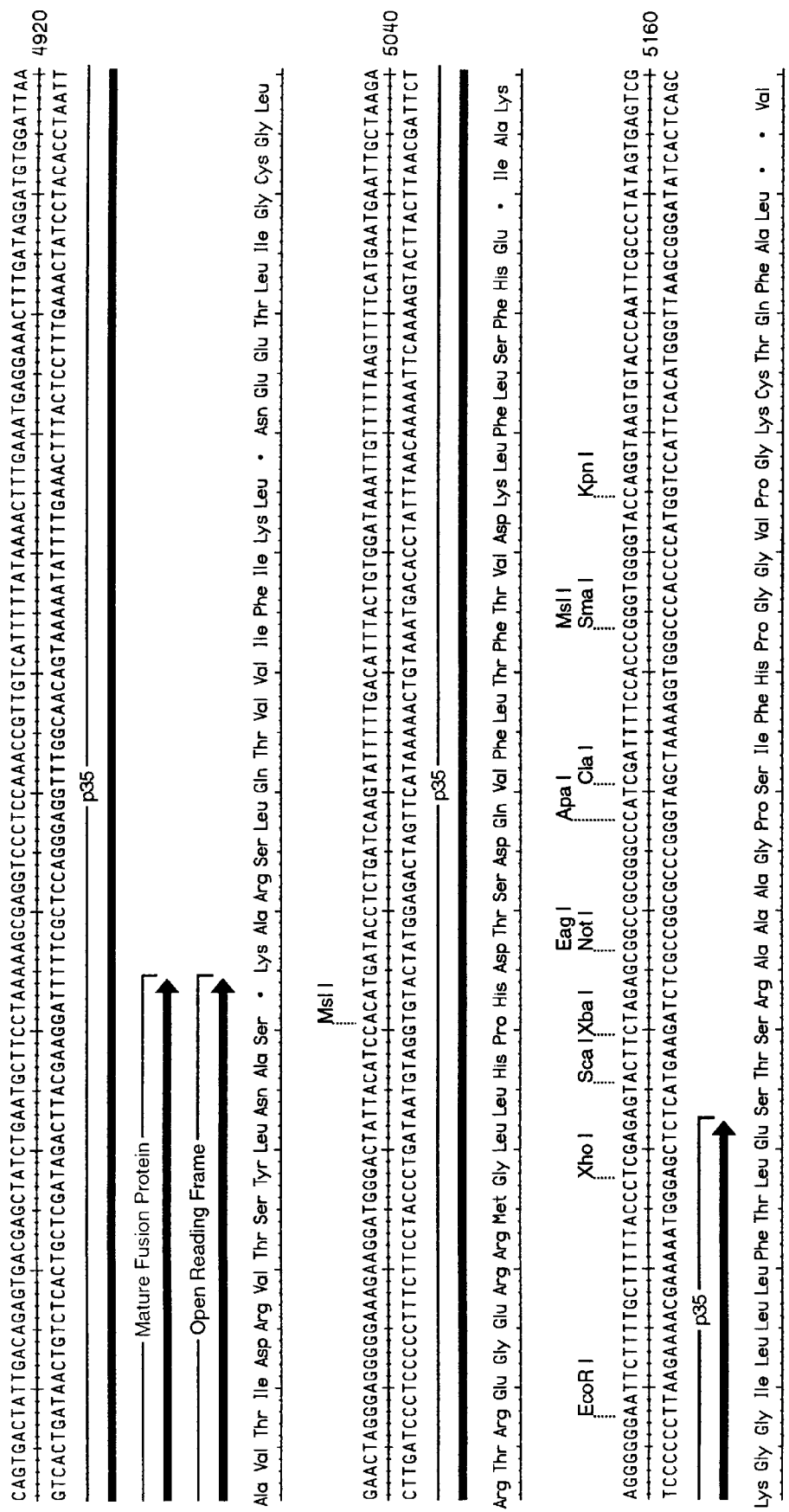
Fig. 11 (Cont 11).

```
             Dra III
TATCAGGGCGATGGCCCACTACTGTGAACCATCACCCTAATCAAGTTTTTTGGGGTCGAGGTGCCGTAAAGCACTAAATCGGAACCCTAAAGGGAGCCCCGATTTAGAGCTTGACGGGGA
                                                                                                                      6000
ATAGTCCCGCTACCGGGTGATGCACTTGGTAGTGCCATTAGTTCAAAAAACCCCAGCTCCACGGCATTTCGTGATTAGCCTTGGATTTCCCTCGGGGGCTAAATCTCGAACTGCCCCT
Leu Ser Gly Arg Trp Pro Thr Thr • Thr Ile Thr Leu Ile Lys Phe Phe Gly Val Glu Val Pro • Ser Thr Lys Ser Glu Pro • Arg Glu Pro Pro Ile • Ser Leu Thr Gly

AAGCCGGCGAACGTGGCGAGAAAGGAAGAAGCGAAAGGAGCGGGGCGCTAGGGGCGCTGGCAAGTAGCGGTCACGCTGCCGTAACCACCACCCGCCGCCGCTTAATGCCCG
                                                                                                              6120
TTCGGCCGCTTGCACCGCTCTTTCCTTCTTCGCTTTCCTCGGCCCGCGTTCACATCGCCAGTGCCGACGCGCATTGGTGTGGTGTGGGCGGCGAATTACGCGGC
Lys Ala Gly Glu Arg Gly Lys Gly Arg Glu Glu Ser Glu Arg Ser Gly Arg • Gly Ala Gly Lys Cys Ser Gly His Ala Ala Arg Asn His Thr Arg Arg Ala • Cys Ala

CTACAGGGCGCGTCAGGTG
                   6139
GATGTCCCGGCCAGTCCAC
Ala Thr Gly Arg Val Arg Trp
```

INTERLEUKIN-12 FUSION PROTEIN

FIELD OF THE INVENTION

This invention relates to Interleukin-12 fusion proteins and nucleic acid constructs encoding them, and to the use of such fusion proteins and constructs in tumour therapy especially therapy of leukaemia. More particularly it relates to carrying out such therapy by means of cell therapy.

BACKGROUND OF THE INVENTION

Interleukin-12 (IL-12), is a cytokine, first described as Natural Killer Stimulatory Factor and Cytotoxic Lymphocyte Maturation factor in the late 1980s (Kobayashi et al., 1989; Stern et al., 1990), is a monocyte/macrophage derived cytokine (D'Andrea et al., 1992; Gazzinelli et al., 1993). IL-12 has become the most promising cytokine for the immunotherapy of many cancers due to its pleiotropic effects both In vitro and in vivo. IL-12 has pronounced mitogenic activity on activated T and Natural Killer (NK) cells via an IL-2 independent mechanism (Gately et al., 1991), it also enances the lytic effects of NK cells (Kobayashi et al., 1989) and can promote the expansion of activated T and NK cells (Gately et al., 1991). However, the major interest in IL-12 for cancer immunotherapy is due to its ability to directly stimulate the production of Interferon-γ (INF-γ) from peripheral blood T and NK cells (Wolf et al., 1991) and its ability to promote the development of Th1 CD4+ T helper cells from naive Th0 cells (Manetti et al., 1993; Scott, 1993). Th1 cells propagate cell mediated immune reactions. Indeed both systemic and intra-tumoural administration of recombinant IL-12 (rIL-12) have shown potent anti-tumour activity in every murine tumour studied and reported to date (Brunda et al., 1993; Nastala et al., 1994). Systemic administration of IL-12 has been shown to elicit potent anti-tumour activity in all murine models studfed to date (Brunda et al., 1993; Nastala et al., 1994). It appears that this anti-tumour effect is mediated via activation of CD8+ T cells and requires INF-γ. Additionally, it Mas been recently shown that rIL-12 is capable of preventing tumour metastasis (Mu et al., 1995) and acute graft versus host disease (Sykes et al., 1995). The most promising results with rIL-12, including total tumour regression and establishment of immunological memory, were obseeed using fibroblasts that had been genetically engineered to secrete IL-12 using an IRES-containing retrovirus. These cells were admixed with tumour cells before being returned to the animal (Tahara et al., 1994). It has been hypothesised that local secretion of cytokines from turhour cells will activate the anti-tumour effectors to establish immunity in vivo by best approximating the natural role of IL-12 in eliciting an immune response.

Although rIL-12 has demonstrated potent anti-tumour effects, all cytokines should be delivered in a manner to reduce toxicity to the patient. Indeed administration of rIL-12 has been shown to give the best therapeutic effects when delivered atlthe site of the tumour (Brunda et al., 1993).

It has been that IL-12 has a synergistic effect with the B7/CD28 interaction between the antigen-presenting cell and the appr riate T cell, in inducing proliferation and promoting a Th1 pattern cytokine production in mitogen activated peripheral blood T cells (Kubin et al., 1994; Murphy et al., 1991).

A major difficulty in the construction of a vector designed to deliver IL-12 results from the way in which IL-12 is naturally sythesised. The functional cytokine is a glycosylated, disulphide linked, heterodimer of molecular weight 70 kDa (p70) which is comprised of two unrelated subunits, a light thain of 35 kDa (p35) and heavy chain of 40 kDa (p40). Functional IL-12 requires co-expression of both of the individual genes which encode each subunit (Gubler et al., 1991), Using the internal ribosome entry site (IRES) element of the encephalomyocarditis virus to allow cap-independent translation, a retroviral construct that allows coordinated high level expression of IL-12 has been developed (Zitvogel et al., 1994). This construct has subsequently been used to eradicate established murine sarcomas (Tahara et al., 1995). ronzever, the use of IRES elements presents serious problems. To express an additional gene in these constructs, such a B7, would involve an additional IRES element and there would be a risk of homologous recombination between these IRES elements resulting in the splicing out of apportion of the insert.

Another potential drawback of using multiple IRES elements is that it leads to a reduction of expression downstream from each IRES element (Zitvogel et al., 1994) which affects the overall efficiency of any IRES-containing vector where maximal expression is required. Expression from each successive downstream IRES element is lower than from the previous one so the more IRES elements, the lower the expression of the gene products regulated by those located downstream.

Additionally, in the murine model, homodimeric p40 is antagonistic to the activity of heterodimeric p70 (mattner et al., 1993). Thus, where p35 and p40 are translated independently, there is the possibility that some p40 will homodimerise rathkr than heterodimerising with p35. This reduces the pool of p40 available for heterodimerisation, as well as actively inhibiting p70 (i.e. functional IL-12) activity.

SUMMARY OF THE INVENTION

The present invention seeks to provide a solution to the problems of unregulated translation and homologous recombination in three-gene vectors. The invention provides a fusion protein that encodes both the p35 and p40 cDNAs of IL-12, employing a linker sequence. This allows both polypeptides to fold into their native three-dimensional structure. This reduces the need for an IRES sequence within a viral vector and therefore greatly reduces the possibility of homologous recombination within vector sequences. It also eliminates unregulated expression of the two IL-12 cDNA's. We have constructed a cDNA which allows expression of such a protein which we have called Flexi-12. We demonstrate here that the cDNA encoding Flexi-12 produces a protein that mimics the biological activities of rIL-12 such as the proliferation of activated T cells, production of INF-γ from activated T cells, activation of NK cells and phosphorylation of the same intercellular signal transduction proteins as rIL-12.

The invention, thus provides: a nucleic acid construct comprising a coding region encoding an interleukin-12 (IL-12) fusion protein, said fusion protein comprising: (a) an IL-12 p35 subunit (b) an IL-12 p40 subunit; and (c) joining said subunits, a linker peptide;

A viral vector comprising a nucleic acid construct comprising a coding region encoding an interleukin-12 (IL-12) fusion proteinl said fusion protein comprising: (a) an IL-12 p35 subunit; (b) an IL-12 p40 subunit; and (c) joining said subunits, a linker peptide;

A host cell transfected with a viral vector comprising a nucleic acid construct comprising a coding region encoding an interleukin-12 (IL-12) fusion protein, said fusion protein comprising: (a) an IL-12 p35 subunit; (b) an IL-12 p40 subunit; and (c) joining said subunits, a linker peptide; and An interleukin-12 (IL-12) fusion protein, said fusion protein comprising (a) an IL-12 p35 subunit (b) an IL-12 p40 subunit; and (c) joining said subunits, a linker peptide.

The invention also provides pharmaceutical compositions compr ising such constructs, vectors, cells and proteins.

The invention also provides methods of treating diseases involving uncontrolled cell proliferation, especially leukaemia, using such constructs, vectors, cells and proteins.

Using actin control primers it was possible to show that the PCR is amplifying the RT product rather than contaminating DNA. Control DNA from normal bone marrow (Lane A) gives a arger product (608 bp, arrowed) than the RT product from cells either mock transfected (Lane B) or transfected with the Flexi-12 DNA (Lane C) or an IL-12 IRES construct (Lane D), which gives a smaller product (181 bp, arrowed). No evidence of amplification of the COS-7 genomic DNA is present. Molecular weights (Lane M) are 1000, 700, 500, 400, 300, 200 and 100 bp.

Figure 1A:
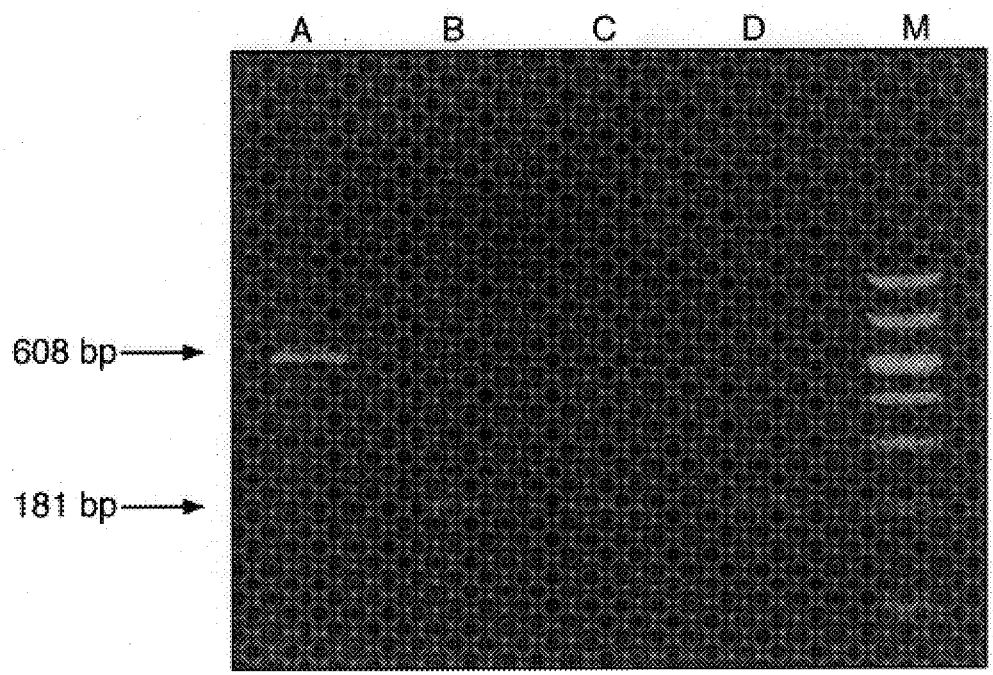
FIGS. 1 and 1A.
RT-PCR analysis of transfected and untransfected COS-7 cells.
Figure 1B:
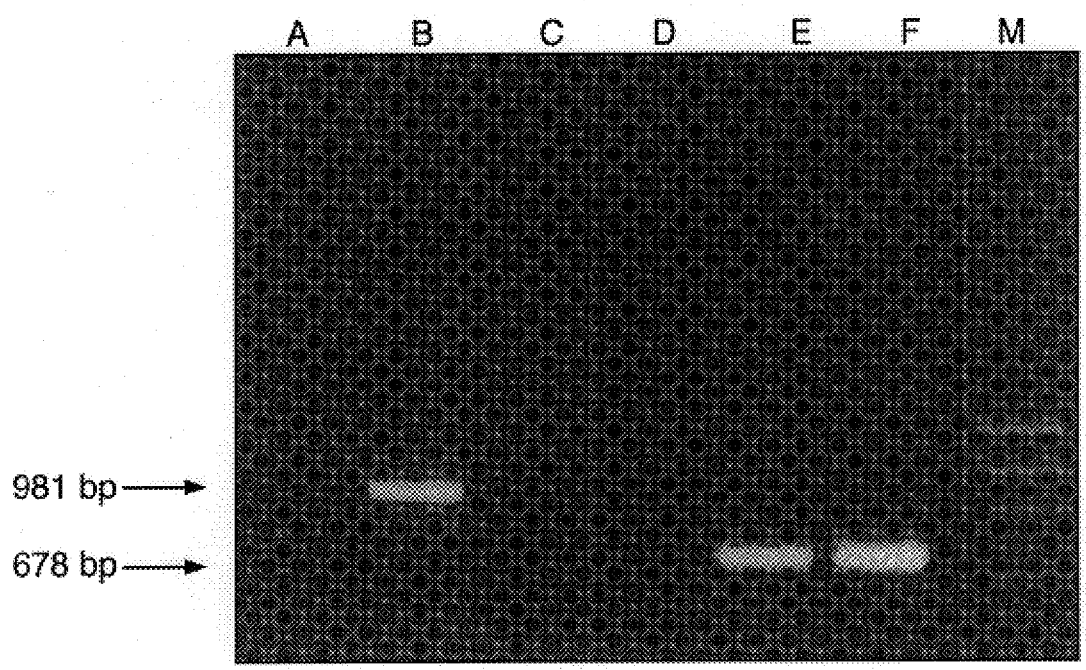

FIG. 1B.
RT-PCR analysis for Flexi-12 and IL-12 p40 in transfected and untransfected COS-7 cells.

Using primers specific for the linker/p35 junction region of the fusion molecule, no bands were seen with either IL-12 IRES construct (Lane A) or mock infected cells (Lane C) but a specific bard of 981 bp (arrowed) was observed only with the Flexi-12 construct (Lane B).

Using primers specific for the p40 cDNA, no signal was detected in the mock transfected cells (Lane D) whilst both the Flexi-12 construct (Lane E) and the IL-12 IRES construct (Lane F) gave a specific band of 678 bp (arrowed). Molecular weights (Lane M) are 1353, 1078, 872 and 603 bp.

Figure 2:
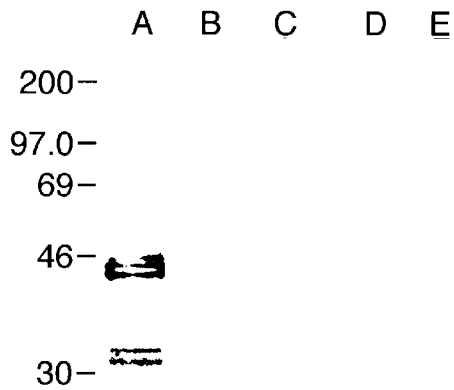

FIG. 2.
Western blot analysis of the COS-7 transfacted supernatant.

Recombinant IL-12, mock transfected supernatant and Flexi-12 transfected supernatant separated by SDS-PAGE under reducing conditionb and analysed as described in Materials and Methods. 1 ng Recombinant IL-12 (Lane A) gave bands at 35 and 40 kDa. The multiple bands seen are due to differential glycosylation of the recombinant protein. 50 µl (Lane B) and 1000 µl (Lane C) mock transfected supernatant showed no band, whilst 0.5 ng (50 µl) Flexi-12 (Lane D) and 1 ng (100 µl) Flexi-12 (Lane E) gave just a single band at 70 kDa with no free 35 or 40 kDa bands present. Molecular weights in kDa ate indicated on the left.

Figure 3:
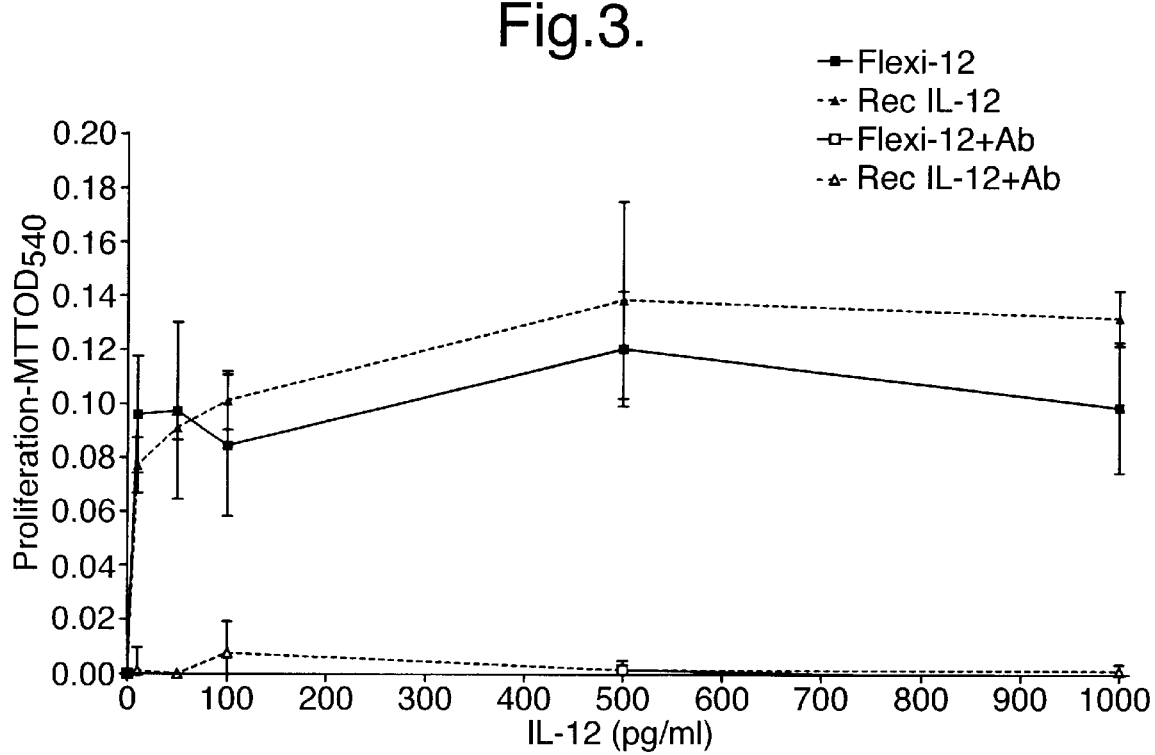

FIG. 3.
Mitogenic activity of Flexi-12.

PHA blasts were ikcubated with either Flexi-12 (solid line, closed squares) or recombinant IL-12 (dotted line, closed triangles), Both IL-12 and Flexi-12 were able to induce the proliferation of PRA blasts in a dose dependent manner. The differences seen between Flexi-12 and recombinabt IL-12 were not significant.

The addition of 10 µg/ml neutralising anti-IL-12 antibodies was able to preve t the mitogenic response of both Flexi-12 (solid line, open squares) and recombinant IL-12 (dotted line, open triangles).

The results are expressed as the means ±SD of six independent experiments less the mean of unstimulated control cells.

Figure 4:
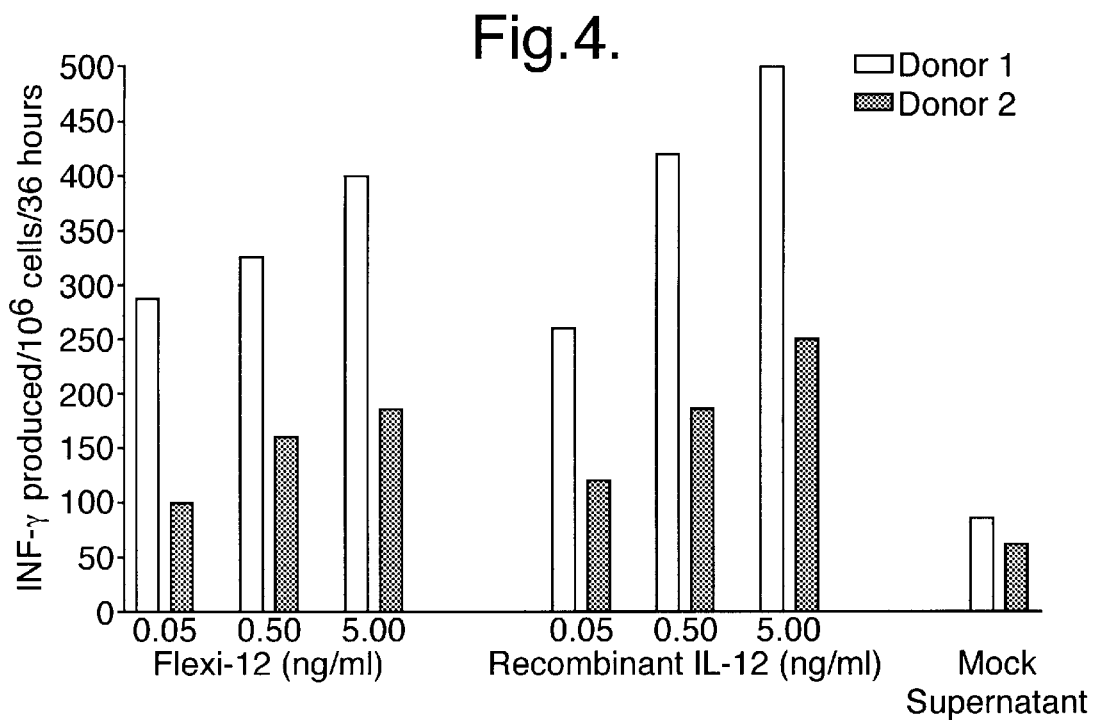

FIG. 4.
Flexi-12 incubated PEA blasts secrete INF-γ in a dose dependant manner.

PHA blasts were in ubated with either IL-12 or Flexi-12 as described in Materials and Methods. Supernatants were assayed by ELISA for IFN-γ 36 hours after addition of either IL-12 or Flexi-12.

Figure 5:
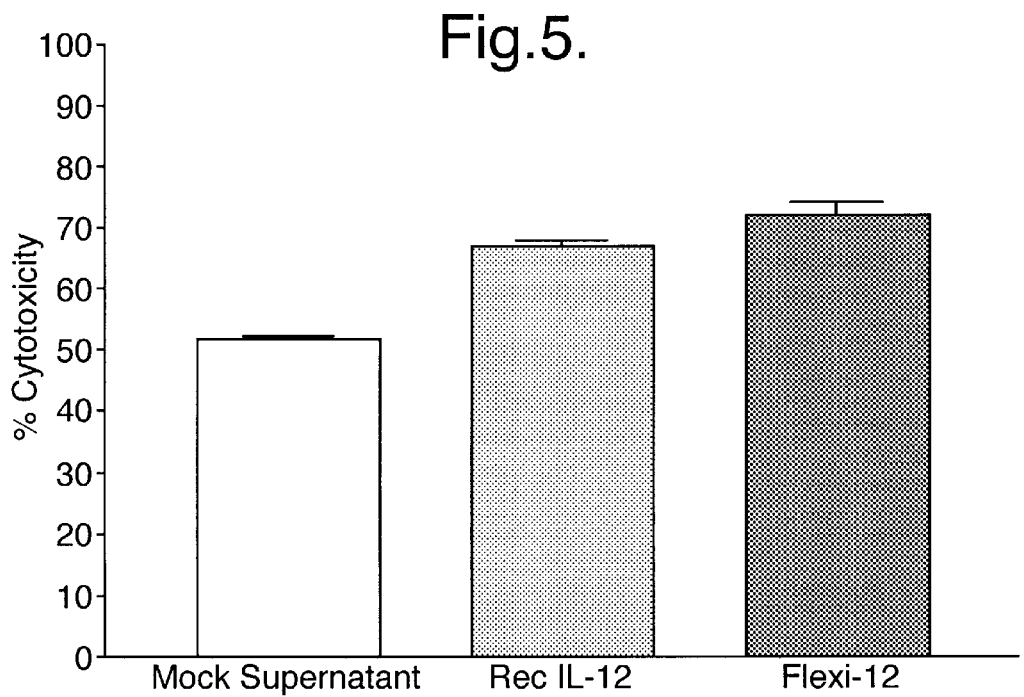

FIG. 5.
Flexi-12 mediates enhanced NK cell killing.

PBLs were incubated with either IL-12 or Flexi-12 as described in Mater,als and Methods. PBLs were incubated with labelled K562 targets in a 4 hour cytotoxicity assay. E:T ratio was 10:1. Both recombinant IL-12 (open column) and Flexi-12 (shaded column) showed enhanced killing above mock transfected cell supernatant (filled column).

FIG. 6.
Both IL-12 and Flexi-12 induce the tyrosine phosphorylation of the STAT 4 member of the STAT family of proteins.

PHA activated T cells ($2\times10^7$) were incubated in medium alone or with IL-12 or Flexi-12. STAT 4 immunoprecipitates were resolved by SDS-PAGE and analysed by anti-phosphotyrosine immunoblotting.

Figure 6A:
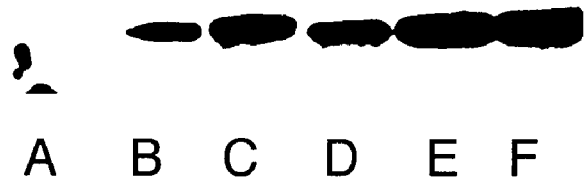

FIG. 6A.
Lane A, mock transfected COS-7 cell supernatant, Lane B 1 ng/ml Flexi-12, 15 minute incubation, Lane C 1 ng/ml Flexi-12, 30 minute incubation, Lane D 1 ng/ml IL-12, 5 minute incubation, Lane E 1 ng/ml IL-12, 15 minute incubation and Lane F 1 ng/ml IL-12, 30 minute incubation.

Figure 6B:

FIG. 6B.
As a loading control, the blot was stripped and reprobed with anti-STAT 4 antibody to a different epitope as described above.

Figure 7:
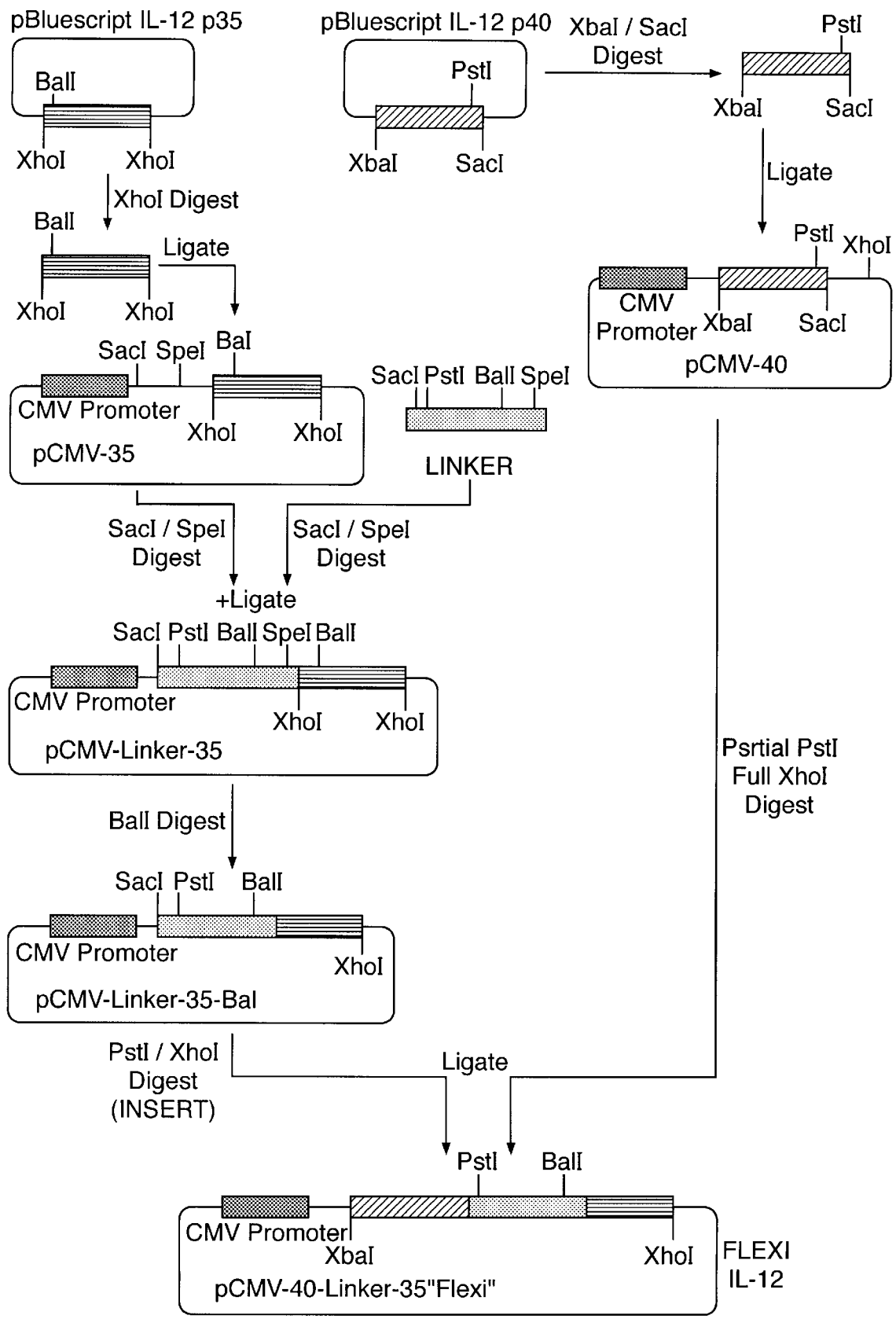

FIG. 7.
A schematic diagram of the construction of Flexi-12.

Starting plasmids were pBK-CMV (Stratagene), and the human cDNAs for IL-12 p35 and p40 in pbluescript.

FIG. 8
cDNA and translates amino acid sequence of human p35 (cDNA sequence is SEQ ID No. 1, amino acid sequence is SEQ ID No. 2).

FIG. 9
cDNA and translated amino acid sequence of human p40 (cDNA sequence is SEQ ID No. 3, amino acid sequence is SEQ ID No. 4).

FIG. 10
cDNA and translated amino acid sequence of human B7.1 (cDNA sequence is SEQ ID No. 5, amino acid sequence is SEQ ID No. 6).

Figure 11:
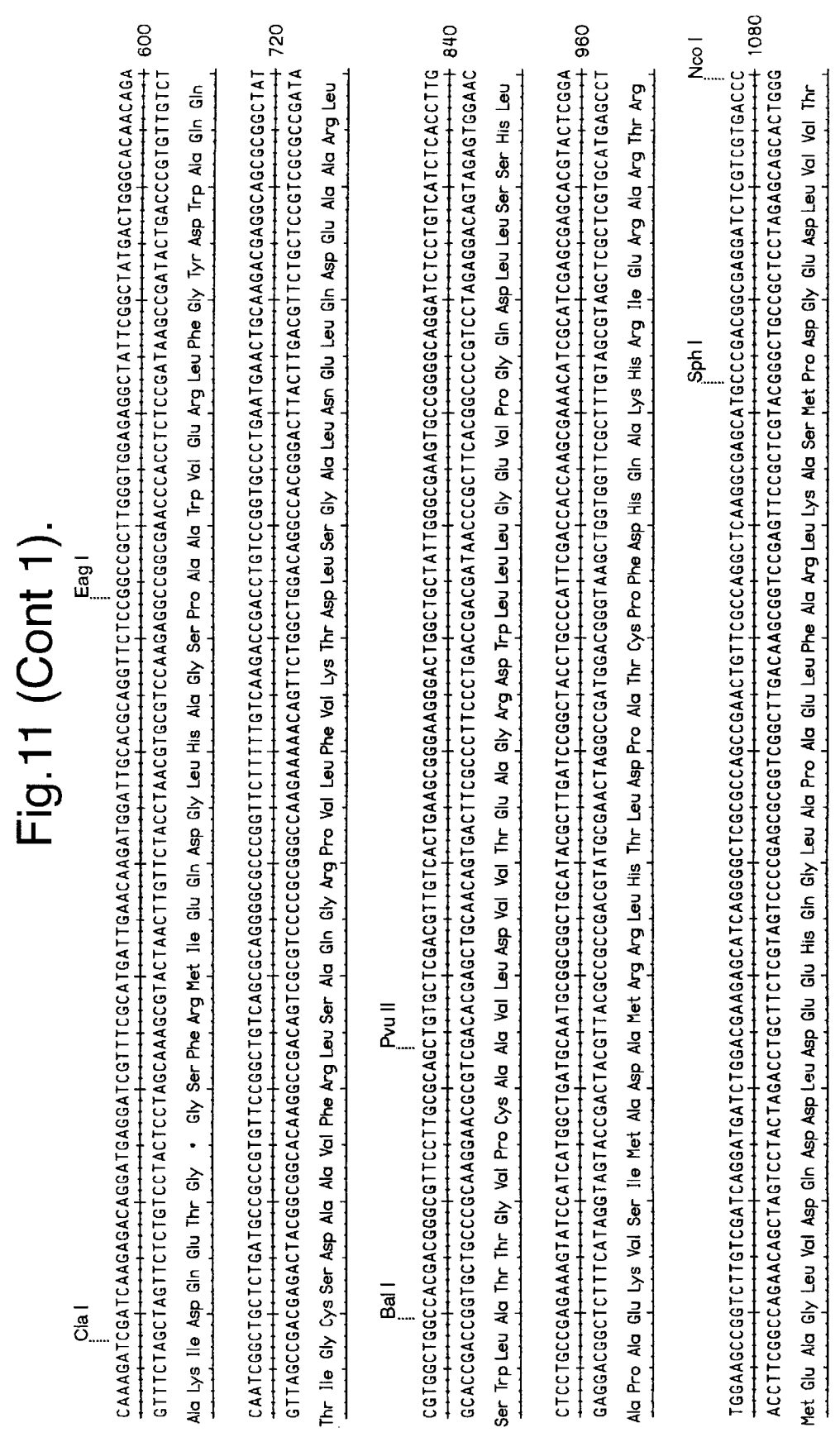
Figure 11:
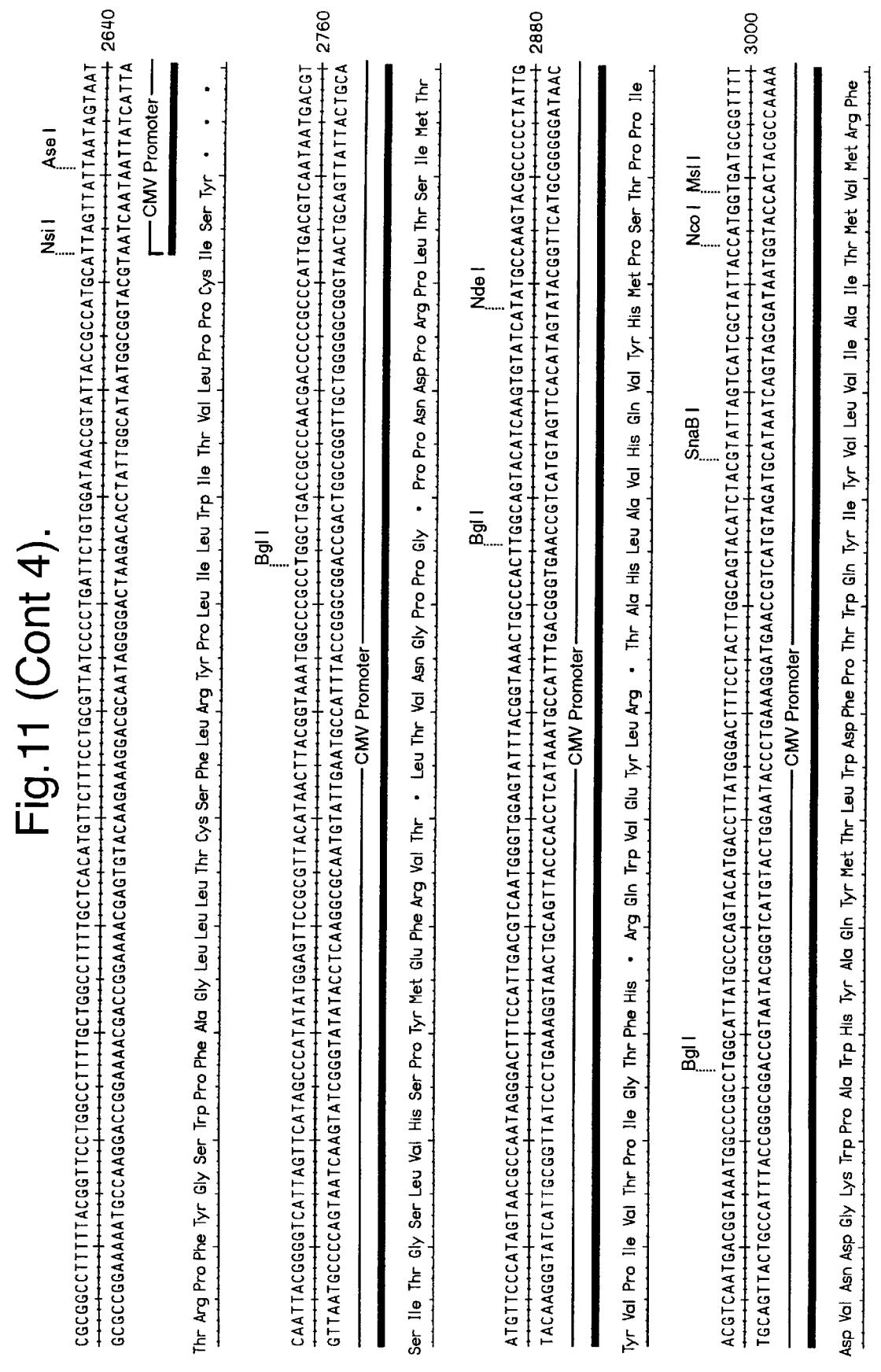
Figure 11:
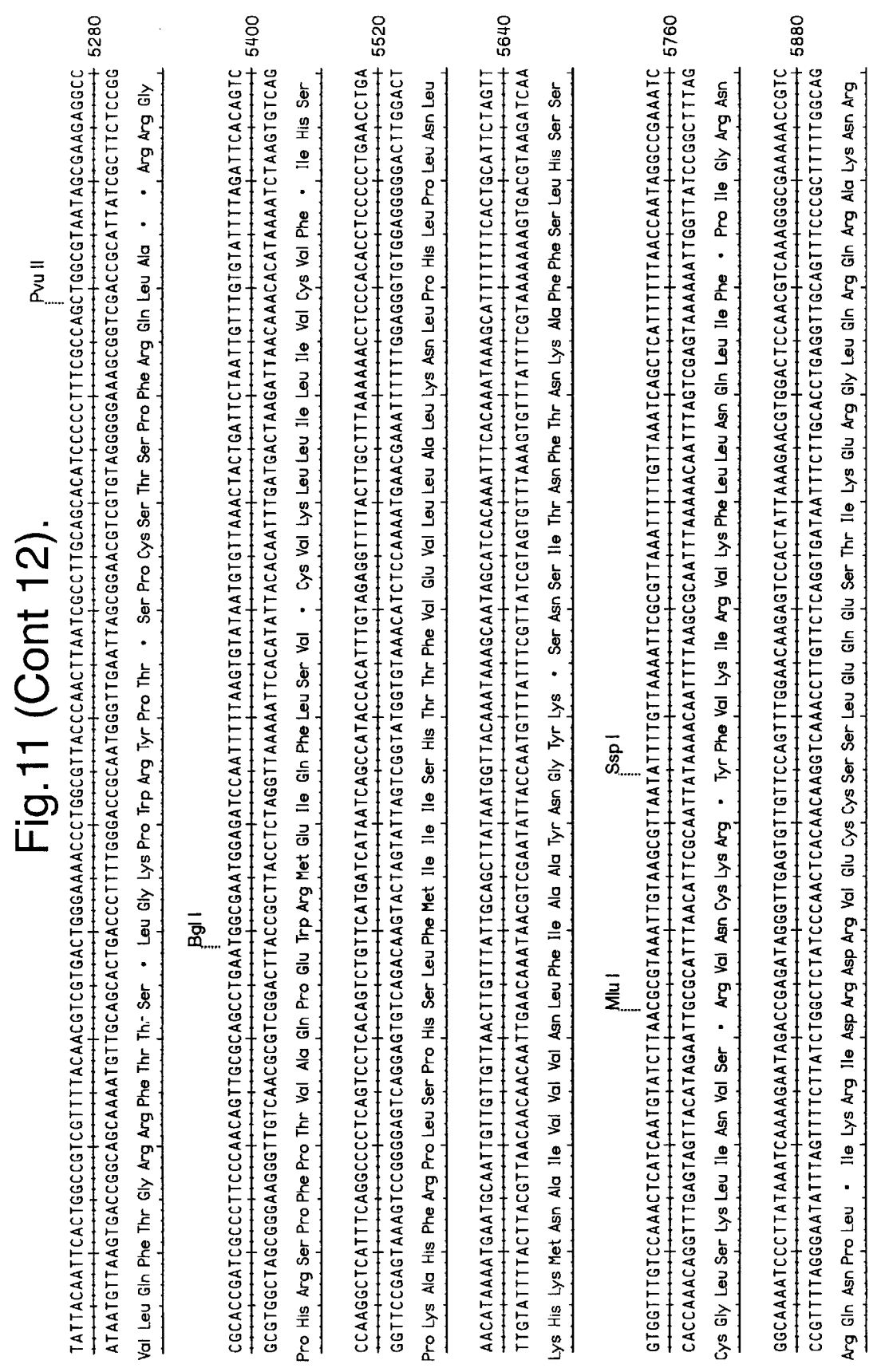

FIG. 11
DNA and encoded amino acid sequence of Flexi-12 inserted into pBK-CMV (stratagene). The following features of the sequence are indicated: sequence of the CMV promoter; sequence of the p40 subunit; sequence of the linker and the element of the linker that reproduces the first 6 amino acids of p35; sequence of the p35 subunit; sequence of the signal peptide and mature Flexi-12 fusion protein; sequence of the open reading frame encoding Flexi-12; and restriction enzyme sites.

In FIG. 11, the entire sequence is SEQ ID No. 7 (DNA) and SEQ ID No. 8 (amino acid). The sequence of the open reading frame encoding Flexi-12 is SEQ ID No. 9 (DNA) and SEQ ID No. 10 (amino acid). The sequence of the mature Flexi-12 protein without the signal sequence is SEQ ID No. 11 (DNA) and SEQ ID No. 12 (amino acid). The sequence of the linker including the portion that reproduces the first six amino acids of p35 is SEQ ID. No. 13 (DNA) and SEQ ID No. 14 (amino acid).

DETAILED DESCRIPTION OF THE INVENTION

The present invention provides Interleukin-12 (IL-12) fusion proteins ("Flexi-12" proteins) comprising the following components: (a) an IL-12 p35 subunit; (b) an IL-12 p40 subunit; and (c) joining said subunits and a linker peptide.

The Flexi-12 fusion proteins of the invention have IL-12 activity. Herein, IL-12 activity is defined as being at least one biological property of naturally occurring IL-12. Such properties include (i) mitogenic effects on activated T- and Natural Killer (NK) cells(s); (ii) enhancement of the lytic effects of NK cells; (iii) promotion of the expansion of activated T and NK cells, (iv) ability to stimulate interferon-$\gamma$ (IFN-$\gamma$) from peripheral blood T and NK cells; and (v) ability to promote the development of CD4+ T helper (Th1) cells from naive Th0 cells. A further property is (vi) anti-tumour effects in any tumour in any mammal, for example mice as experimental models, but preferably humans as patients, Human IL-12 is believed to be functional in this way ((vi)) only in humans whereas murine IL-12 is believed to be functional in mice and humans. Thus, where the fusion protein comprises human subunits, it is expected to have anti-tumour effects in humans. Where it comprises mouse subunits, it may have such effects in mice or humans. Further, the subunits of the Flexi-12 fusion proteins of the invention have the same sequence as those of naturally occurring IL-12, or similar sequences as described below.

Immune co-stimulatory molecules, particularly of the B7 family, may be used in combination with the Flexi-12 fusion proteins of the invention. Herein, B7 molecules are defined as immune co-stimulatory molecules as previously described in the art. B7 molecules suitable for use according to the invention share at least one biological property of a naturally occurring B7 molecule. For example, they may share B7's ability to interact with CD28 or CTLA4 when CD28 or CTLA4 is presented at a T-cell surface. Preferably, as a result of this interaction, they share B7's ability to stimulate the secretion of IL-2, which stimulates proliferation and/or differentiation of the T-cells.

The invention provides nucleic acid constructs encoding the IL-12 fusion proteins of the invention. These comprise coding regions encoding p35 and p40 subunits, and they preferably also comprise a coding region encoding a B7 molecule.

The cDNA sequences of human p35 and human p40 and the human B7 molecule B7.1 are given in FIGS. 8, 9 and 10 respectively (SEQ ID No. 1, 3 and 5 respectively). These sequences are preferred sequences of the invention. However, the invention is not limited to the use of these sequences in constructs of the invention. Rather, it also provides for the use of other closely related variant sequences which have the same biological activity, or substantially similar biological activity. For p35 and p40 subunits, variant sequences encode protein subunits which, when present in a Flexi-12 fusion protein of the invention, give the fusion protein one or more of the biological properties of IL-12 as described above. Similarly variant B7 sequences encode proteins having one or more of the properties of a B7 molecule as defined above.

Both DNA sequences and RNA sequences may be used as p35, p40 and B7 coding sequences in the constructs of the invention. It will be appreciated by those of skill in the art that, in RNA sequences of the invention, T residues will be replaced by U.

DNA sequences of the invention may be related to those of SEQ ID No. 1, 3 or 5 in a number of ways. For example, DNA sequences suitable for the practice of the invention may be degenerate sequences that encode the same protein, the protein of SEQ ID No. 2, 4 or 6.

Alternatively, DNA sequences of the invention may be substantially homologous to that of SEQ ID No. 1, 3 or 5 and encode a protein that differs in amino acid sequence from that of SEQ ID No. 2, 4 or 6. Typically, DNA sequences of the invention have at least 70%, at least 80%, at least 90%, at least 95% or at least 99% sequence homology to the sequence of SEQ ID No. 1, 3 or 5.

DNA sequences of the invention may, for example, be genomic DNAs or cDNAs, or hybrids between genomic DNA and cDNA, or they may be synthetic or semi-synthetic. They may originate from any species, though DNAs encoding human proteins are preferred. So far as genomic DNAs are concerned, genomic DNAs encoding the proteins of SEQ ID No. 2, 4 or 6 are particularly preferred.

DNA sequences of the invention may be single-stranded or double-stranded.

DNA sequences of the invention may differ from the sequence shown in SEQ ID No. 1, 3 or 5 by the deletion, insertion or substitution of one or more nucleotides, provided that they encode a protein with the appropriate biological activity as described above. Similarly, they may be truncated with respect to SEQ ID No. 1, 3 or 5 or extended by one or more nucleotides. For p35 and p40 subunits, the truncation may optionally be compensated for by the sequence of the linker peptide, where the truncation is a the end of the sequence joined to the linker.

Alternatively, DNA sequences of the invention may be capable of hybridising to the sequences of SEQ ID No. 1, 3 or 5. For example, they may be capable of hybridising under conditions of high stringency, e.g. 0.2×SSC at 60° C.; or lower stringency, e.g. 2×SSC at 60° C.

RNA sequences are also suitable for the practice of the invention. In particular, the invention provides for the use of the RNA sequence corresponding to those of SEQ ID No. 1, 3 or 5, which are preferred RNA sequences. The invention also provides for the use of RNA sequences that are related to thee sequences in any of the ways described above for DNA sequences. RNA sequences for the invention may be single-stranded or double-stranded.

Nucleic acids of the invention may be of any origin. For example, they may originate from any species, although DNAs and RNAs encoding human p35, p40 and B7 proteins particularly those having the sequence shown in SEQ ID No. 2, 4 or 6 are preferred. Synthetic DNAs may also be used, as may semi-synthetic RNAs.

Variant DNA and RNA sequences may be prepared by any suitable means known in the art, for example as described in Sambrook et al. For example, they may be prepared by site-directed mutagenesis or by other known techniques of molecular biology such as digestion with restriction enzymes followed by ligation to form new sequences.

Similarly, the invention provides for the use of naturally occurring variants of p35, p40 and B7 coding sequences. For example, allelic variants of the human sequences of SEQ ID No. 1, 3 and 5 may be used. These may be obtained by any means known in the art, for example by probing cDNA or genomic DNA libraries with probes derived from the sequences of SEQ ID No. 1, 3 or 5 using techniques known in the art, for example as described in Sambrook et al. Also, corresponding p35, p40 and B7 sequences may be obtained from other species by similar techniques. For example, simian (e.g. monkey, chimpanzee), rodent (e.g. mouse, rat, guinea pig or rabbit), bovine, canine, feline or other mammalian sequences may be obtained and used according to the invention. Human sequences are preferred.

In particular, the term B7 covers a family of related molecules. Of these, B7.1 is preferred but B7.2 and B7.3 are also known and may be used. B7.2 has been cloned and sequenced (Freemen et al Science 262 (5135), 909–911 (1993) Azuma et al (Nature 366 (6450), 76–79 (1993) have also reported the sequence, under the name B70. B7.3 is known to exist but has not yet been cloned or sequence. Similarly, B7 molecules isolated in the future may be used. Similarly, other non-B7 co-stimulatory molecules can be used. The EMBL accession number of B7.1 is M27533 and that of B7.2 is L25259.

p35, p40 subunits and B7 proteins of the invention are encoded by DNA orRNA sequences of the invention as defined above. Preferred proteins of the invention are the proteins of SEQ ID No. 2, 4 and 6, though the invention also provides for the use of other variant proteins having closely related sequences that differ from those of SEQ ID No. 2, 4 or 6 but have appropriate biological activity, as defined above. Thus, variant p35 and p40 proteins, when incorporated into fusion proteins of the invention, confer on the fusion proteins at least one biological property of naturally occurring IL-12. Similarly, variant B7 proteins have B7 activity, as defined above.

Variants suitable for the practice of the invention may therefore be substantially homologous to the proteins of SEQ ID No. 2, 4 or 6, typically at least 70%, at least 80%, at least 90%, at least 95% or at least 99% homologous.

Variant proteins suitable for the practice of the invention may differ from the sequence shown in SEQ ID No. 2, 4 or 6 by the deletion, insertion or substitution of one or more amino acids. Similarly, they may be truncated by one or more amino acids with respect to SEQ ID No. 2, 4 or 6 or extended with respect to SEQ ID No. 2, 4 or 6 by one or more amino acids.

In respect of substitutions, conservative substitutions are preferred. Typically, conservative substitutions are substitutions in which the substituted amino acid is of a similar nature to the one present in the naturally occurring protein, for example in terms of charge and/or size and/or polarity and/or hydrophobicity. Similarly, conservative substitutions typically have little or no effect on the activity of the protein.

Proteins of the invention that differ in sequence from naturally occurring IL-12 may be engineered to differ in activity from naturally occurring IL-12. For example p35 and p40 proteins may be engineered to confer stronger IL-12 activity on the fusion proteins. Such manipulations will typically be carried out at the nucleic acid level using recombinant techniques known in the art, as described above.

Nucleic acid constructs of the invention comprise coding sequences encoding p35 and p40 subunits of the invention, as described above, and optionally a coding region encoding a B7 subunit, as described above.

More specifically, nucleic acid constructs of the invention typically comprise: (i) a promoter operably linked to (ii) a coding region encoding an interleukin-12 (IL-12) fusion protein said coding region comprising the following components: (a) a coding sequence encoding an IL-12 p35 subunit; (b) a coding sequence encoding an IL-12 p40 subunit of IL-12; and (c) joining components (a) and (b), a coding sequence encoding a linker peptide.

As to the promoter component (i), any suitable promoter may be used to control the expression of the nucleic acid of the invention. In general, it is preferred to use a viral promoter or a promoter adapted to function in a cell into which the constructs to be introduced. Thus, in the case of a human cell, for example, it is preferred to use viral promoters, especially promoters derived from viruses that infect humans, or promoters derived from human genes.

Similarly, promoters may be chosen to function in particular cell types e.g. in COS cells, fibroblasts or tumour cells, for example leukaemia cells. Tissue-specific promoters may also be used, e.g. breast-specific, or muscle specific promoters. In particular, promoters specific to tumour cells to be transformed with vectors comprising the construct may be used. Thus, for example, where a breast tumour is to be treated, a breast-specific promoter may be used. Also, if expression of naked DNA constructs in muscle is desired, a muscle-specific promoter may be used.

Optionally, a promoter may be used in combination with any suitable enhancer.

Desirably, a "strong" promoter is used, i.e. one that secures high levels of expression of the fusion protein of the invention. Promoters that achieve overexpression of the fusion protein are desirable.

Preferred promoters include the cytomegalovirus (CMV) promoter, optionally in combination with the CMV enhancer; the human β-actin promoter; the simian virus 40 (SV40) early gene promoter; the Rous sarcoma virus (RSV) promoter; and the retroviral long terminal repeat (LTR) promoter.

The promoter is operably linked to the coding region encoding the fusion protein of the invention. Thus, the promoter is positioned relative to the coding sequence encoding the fusion protein such that it is able to direct expression of the fusion protein. Desirably, the promoter is positioned to allow it to exert its maximum effect on expression.

Preferably, the constructs of the invention also comprise a coding sequence encoding a B7 molecule, as described above. This sequence may be operably linked to a further promoter as described above. Alternatively, expression of the B7 molecule may be under the control of the same promoter. In this case, the B7 coding sequence is operably linked to the promoter that controls expression of the fusion protein.

For example, the construct may be constructed such that expression driven by a single promoter generates mRNA comprising both the sequence encoding the fusion protein and the sequence encoding the B7 molecule. In such a case, the two proteins are translated separately.

Thus, for example, whichever of the B7 coding region and the fusion protein coding region is the more downstream in the direction of translation may be preceded by, and operably linked to, an internal ribosome entry site (IRES). This will control its translation. The upstream coding sequence will comprise a stop codon at its downstream end to prevent translational read through from one coding region to the other.

Any suitable IRES element may be used. IRES elements are found in the genomes of picornoviridae, of which there are four genera: enteroviruses such as poliovirus, coxsackivirus and echovirus; rhinoviruses; cardioviruses such as encephalomyocarditis virus; and alphaviruses; (see, for example Jang et al, 1990 for a review; and Ghattas et al, 1991). IRES elements from any of these, or from any other virus, may be used. The IRES element from the encephalomyocarditis virus is preferred. It can be obtained commercially e.g. Novagen (as the pCITE vector).

The fusion protein and B7 coding regions may be arranged in either orientation relative to one another. For example, the fusion protein coding region may be upstream of the B7 coding region may be downstream. Alternatively, the B7 coding region may be upstream of the fusion protein coding region. Preferably, the fusion protein coding region is upstream of the B7 coding region.

Similarly, where the fusion protein coding region and the B7 coding region are independently operably linked to separate promoters, the two coding regions may be in either orientation relative to one another. Preferably, the fusion protein coding region is upstream of the B7 coding region.

Preferably, the fusion protein and B7 coding regions are expressed under the control of a single promoter, with the fusion protein upstream of the B7 coding region and the B7 coding region translated under the control of an IRES element. This applies especially when the construct is to be packaged into an adeno-associated virus (AAV), as AAVs are small relative to some other viruses and can hold only a limited amount of inserted DNA.

Within the fusion protein coding region, the p35 and p40 coding sequences may be in any orientation relative to one another. Thus the p35 coding sequence may be upstream of the p40 coding sequence or the p40 coding sequence may be upstream of the p35 coding sequence.

Preferably, the p40 coding sequence is upstream of the p35 coding sequence.

Within the fusion protein coding region, the linker may have any suitable sequence, as long as the fusion protein has IL-12 activity, as defined above. Specifically, the linker sequence must encode a sequence of suitable length to allow both subunits to fold correctly, as they do in nature or substantially as they do in nature, in order to retain the IL-12 activity of the fusion protein. Also, the encoded linker must have a chemical nature, e.g. polarity/hydrophobicity/configuration that allows correct folding or substantially correct folding.

Preferably, the encoded linker comprises amino acids that do not have bulky side groups and therefore do not obstruct the folding of the protein subunits. Further, it is preferred to use uncharged amino acids in the linker. Preferred amino acids include glycine, serine, alanine and threonine.

The linker may be any suitable length if correct folding of the subunits can be achieved. Preferably, the linker is from 5 to 50 amino acids in length, more preferably from 10 to 30 amino acids, more preferably from 15 to 25 amino acids. Preferably, the linker comprises the sequence (Gly-Gly Gly-Gly-Ser)n(SEQ ID NO: 24). n may be any integer from 2 to 10, preferably from 2 to 5, more preferably 3 or 4, most preferably 3.

Similarly, alternative Glycine/Serine linkers may be used e.g. (Gly-Gly-Ser-Gly-Gly)n(SEQ ID NO: 25) or (Gly-Ser-Gly-Gly-Gly)n(SEQ ID NO: 26) or (Gly-Gly-Gly-Ser-Gly) n(SEQ ID NO: 27), n being as defined above.

Linkers of the invention may also comprise hinge regions allowing flexibility. These are preferably positioned at one or both ends of the linker where the linker joins the p35 or p40 subunit. In hinge regions, small amino acids without bulky side groups are particularly preferred, especially Alanine (Ala) and Glycine (Gly). A preferred hinge sequence is Ala-Gly.

Also, the linker nucleotide sequence may encode some of the amino acids of the p35 and/or p40 subunits to which it is attached. For example, where truncated subunits are used, the sequence of the linker may compensate for some or all of the truncation (see Example).

Additionally, the constructs of the invention may comprise other components. For example, the construct may comprise a nucleic acid encoding a signal sequence, so positioned relative to the fusion protein and/or B7 coding sequence such that, on translation, it is capable of directing the protein to a given cell compartment. Any such signal sequence will typically be positioned immediately upstream or downstream of the fusion protein coding region such that the signal sequence and protein are translated as a single entity, with the signal sequence at the C- or N- terminus.

Optionally, where appropriate, the construct may comprise a transcriptional terminator downstream of the fusion protein or B7 coding region. Of course, where both coding regions are expressed under the control of a single promoter, a transcriptional terminator will not be placed between the upstream coding region and the downstream one. Any suitable transcriptional terminator known in the art may be used.

Optionally, the construct may comprise a polyadenylation signal operably linked downstream to the fusion protein or B7 coding region.

Optionally, the construct may comprise one or more selectable marker genes, e.g. antibiotic resistance genes, to allow selection of cells transformed or transfected cells with the construct.

Where a selectable marker gene is used, its expression may be controlled by an independent promoter, or it may be under the control of the promoter that controls expression of the fusion protein and/or B7 protein, with translation controlled by an IRES, as described above. Where an IRES is used, it is preferred that it is the only IRES in the construct, in order to avoid the difficulties of homologous recombination and reduced expression from downstream IRES elements, as described above. Thus, where expression of a marker is controlled by an IRES, the marker gene is typically an alternative to the B7 coding region.

Constructs of the invention may be in substantially isolated form.

Fusion proteins of the invention are encoded by the fusion protein coding regions of constructs of the invention, as described above. Thus, they comprise the following components (a) an IL-12 p35 subunit as described above; (b) an IL-12 p40 subunit as described above; and (C) joining components (a) and (b) a linker peptide as described above.

Fusion proteins of the invention may be in substantially isolated form.

The p35 and p40 subunits may be in either orientation relative to one another. Thus, in the fusion protein, the p35 subunit may be C-terminal to the p40 subunit or the p40 subunit may be C-terminal to the p35 subunit. It is preferred for the p35 subunit to be C-terminal to the p40 subunit.

As described above, any suitable linker that allows the fusion protein to retain IL-12 activity may be used.

Preferably, the fusion protein is encoded by a DNA or RNA sequence which encodes the protein of SEQ ID No. 10 (see FIG. 11), said sequence being more preferably the DNA sequence of SEQ ID No. 9 (see FIG. 11). The sequence of SEQ ID No. 10 includes a signal sequence preceding the p40 subunit. Alternatively, the fusion protein may be encoded by a DNA or RNA sequence which encoders the protein of SEQ ID No. 12 (see FIG. 11), lacking the signal sequence preceding the p40 subunit, said sequence preferably being the sequence of SEQ ID No. 11 (see FIG. 11). Optionally, an alternative signal sequence may be provided (see above).

Proteins of the invention may be engineered to differ in activity from naturally occurring IL-12. For example the p35 and p40 subunits may be engineered to confer stronger IL-12 activity on the fusion proteins. Such manipulations will typically be carried out at the nucleic acid level using recombinant techniques known in the art, as described above.

Similarly, the sequence of the linker may be engineered to confer altered activity on the fusion protein, especially increased activity. For example, the length or configuration of the linker may be manipulated to affect the overall shape of the fusion protein such that it has altered, preferably increased, activity relative to naturally occurring IL-12.

The invention also provides vectors comprising the nucleic acid constructs of the invention, particularly vectors suitable for use in cell therapy or gene therapy. In particular, viral or non-viral vectors may be used.

Suitable viral vectors include adenoviruses, adeno-associated viruses (AAVs), retroviruses, pseudotyped retroviruses, herpesviruses, vaccinia viruses, Semiliki forest virus, and baculoviruses. Adeno-associated viruses and retroviruses are preferred. Adeno-associated viruses are particularly preferred.

Suitable non-viral vectors include plasmids, liposomes, water-oil emulsions, polethylene imines and dendrimers.

Where appropriate, two or more types of vectors can be used together. For example, a plasmid vector may be used in conjunction with liposomes.

Viral vectors of the invention are preferably disabled, e.g. replication-deficient. That is, they lack one or more functional genes required for their replication, which prevents their uncontrolled replication in vivo and avoids undesirable side effects of viral infection. Preferably, all of the viral genome is removed except for the minimum genomic elements required to package the viral genore incorporating the VEGF nucleic acid into the viral coat or capsid. For example, it is desirable to delete all the viral geneome except the Long Terminal Repeats (LTRs) or Invented Terminal Repeats (ITRs) and a packaging signal. In the case of adenoviruses, deletions are typically made in the E1 region and optionally in one or more of the E2, E3 and/or E4 regions. In the case of retroviruses, genes required for replication, such as env and/or gag/pol may be deleted.

Viruses of the invention may be disabled by any suitable technique. For example, genomic deletions may involve complete removal of genes required for replication, or only partial removal. Complete removal is preferred. In general, preferred deletions are of genes required for early transcription of viral genes. Such deletions can be achieved by recombinant means, for example, involving digestion with appropriate restriction enzymes, followed by religation.

Replication-competent self-limiting or self-destructing viral vectors may also be used.

Nucleic acid constructs of the invention may be incorporated into viral genomes by any suitable means known in the art. Typically, such incorporation will be performed by ligating the construct into an appropriate restriction site in the genome of the virus. Viral genomes may then be packaged into viral coats or capsids by any suitable procedure. In particular, any suitable packaging cell line may be used to generate viral vectors of the invention. These packaging lines complement the replication-deficient viral genomes of the invention, as they include, typically incorporated into their genomes, the genes which have been deleted from the replication-deficient genome. Thus, the use of packaging lines allows viral vectors of the invention to be generated in culture.

Suitable packaging lines include derivatives of PA317 cells, ψ-2 cells, CRE cells, CRIP cells, E-86-GP cells, line 293 cells and 293GP cells.

In the case of non-viral vectors, nucleic acid may be incorporated into the non-viral vectors by any suitable means known in the art. For plasmids, this typically involves ligating the construct into a suitable restriction site. For vectors such as liposomes, water-oil emulsions, polyethylene amines and dendrimers, the vector and construct may be associated by mixing under suitable conditions known in the art.

As desired, vectors, especially viral vectors, may be selected to achieve integration of the nucleic acid of the construct of the invention, into the genome of the cells to be transformed or transfected.

When preparing vectors, especially viral vectors, of the invention, it is important to have regard to the capacity of the vector to carry exogenous nucleic acid. Some viruses, in particular, have restricted capacity. Therefore, it is important to ensure that the nucleic acid construct incorporated into the vector does not exceed this carrying capacity. The carrying capacity of given viruses and other vectors is well known to persons of skill in the art and persons of skill in the art can design constructs accordingly.

In particular, for viruses with restricted carrying capacity, it may be desirable to omit the B7 coding region or to ensure that both the B7 and Flexi-12 fusion proteins are expressed under the control of a single promoter with the translation of the more downstream coding region controlled by a IRES.

This applies particularly to AAV's which are an example of viruses with low carrying capacity. Thus, where an AAV vector is used, preferred constructs are those where the B7 and Flexi-12 fusion proteins are expressed under the control of a single promoter with the translation of the more downstream coding region controlled by a IRES. Preferably the Flexi-12 coding region is upstream and the B7 region is preceded by an IRES.

The invention also provides cells transformed or transfected with vectors of the invention, and thus containing constructs of the invention, for example incorporated into their genome.

Such cells may be eukaryotic cells, for example, mammalian, insect or yeast cells; or prokaryotic, e.g. bacterial cells, For example *E. Coli* cells. Preferred insect cells include sf21 cells. Preferred mammalian cells include tumour cells; COS cells, e.g. COS-7 cells; fibroblasts; Chinese hamster ovary (CHO) cells. Tumour cells, are particularly preferred, particularly leukaemia cells, renal, breast, cervical, ovarian and colon tumour cells, and melanoma cells. Preferably, such tumour cells are derived from the individual having a tumour to be treated, or from an individual who is immunologically compatible, as described below.

Cells of the invention may be prepared by transformation or transfection of such cells. This can be achieved by known methods of transfection in the case of viral vectors, e.g. by contacting the viral vectors with target cells, and known methods of transformation in the case of non-viral vectors. Suitable transformation techniques include lipofection, electroporation, calcium phosphate precipitation and particle bombardment.

The invention also provides methods of producing Flexi-12 proteins of the invention by culturing cells of the invention in conditions under which they express the protein. Where the construct contained by the cell includes a B7 coding region, B7 may be produced by co-expression. Similarly, B7 may be co-produced from a separate construct, independently introduced into the cell by any of the methods described above.

The Flexi-12 protein thus produced may then be recovered by any means known in the art, as may the B7 protein.

Preferred cells for the purpose of producing Flexi-12 proteins of the invention are eukaryotic cells, in order to ensure glycosylation of the protein. Preferred eukaryotic cells include insect cells, especially sf21 cells; COS cells, especially COS-7 cells; and CHO cells. Flexi-12 proteins of the invention may also be produced in bacteria, preferably $E.$ $Coli.$ The proteins, nucleic acid constructs, vectors and cells of the invention are preferably presented in the form of a pharmaceutical formulation comprising a pharmaceutically acceptable carrier. Any suitable pharmaceutical formulation may be used.

For example, suitable formulations may include aqueous and non-aqueous sterile injection solutions which may contain anti-oxidants, buffers, bacteriostats, bactericidal antibiotics and solutes which render the formulation isotonic with the bodily fluids of the intended recipient; and aqueous and non-aqueous sterile suspensions which may include suspending agents and thickening agents. The formulations may be presented in unit-dose or multi-dose containers, for example sealed ampoules and vials, and may be stored in a frozen or freeze-dried (lyophilized) condition requiring only the addition of sterile liquid carrier, for example water for injections, immediately prior to use. Some preferred ingredients are SDS, for example in the range of 0.1 to 10 mg/ml, preferably about 2.0 mg/ml; and/or mannitol or another sugar, for example in the range of 10 to 100 mg/ml, preferably about 30 mg/ml; and/or phosphate-buffered saline (PBS).

It should be understood that in addition to the ingredients particularly mentioned above the formulations of this invention may include other agents conventional in the art having regard to the type of formulation in question. Of the possible formulations, sterile pyrogen-free aqueous and non-aqueous solutions are preferred.

The proteins, nucleic acids and vectors of the invention may be delivered in any suitable dosage, and using any suitable dosage regime. Persons of skill in the art will appreciate that the dosage amount and regime may be adapted to ensure optimal treatment of the particular condition to be treated, depending on numerous factors. Some such factors may be the age, sex and clinical condition of the subject to be treated.

For the delivery of naked nucleic acid constructs, typical doses are from 0.1–5000 µg, for example 50–2000 µg, such as 50–100 µg, 100–500 µg and 500–2000 µg per dose.

For the delivery of Flexi-12 protein, suitable doses include doses of from 1 to 1000 µg for example from 1 to 10 µg, from 10 to 100 µg, from 100 to 500 µg and from 500 to 1000 µg.

The dosage used for the delivery of nucleic acid constructs of the invention by means of viral or non-viral vectors will be optimised to take into account clinical factors, including the efficiency with which the vectors deliver the nucleic acid constructs to cells, and the efficiency with which the Flexi-12 and/or B7 are expressed in the cells.

For example, viral vectors may be delivered in doses of from $10^4$ to $10^{14}$ cfu or pfu/ml, for example $10^4$ to $10^6$, $10^6$ to $10^8$, $10^8$ to $10^{10}$, $10^{10}$ to $10^{12}$ or $10^{12}$ to $10^{14}$ cfu pfu/ml. Doses in the region of $10^5$ to $10^9$ cfu or pfu/ml are preferred. The term pfu (plaque forming unit) applies to certain viruses, including adenoviruses and AAVs, and corresponds to the infectivity of a virus solution, and is determined by infection of an appropriate cell culture, and measurement, generally after 48 hours, of the number of plaques of infected cells. The term cfu (colony forming unit) applies to other viruses, including retroviruses, and is determined by means known in the art generally following 14 days incubation with a selectable marker. The techniques for determining the cfu or pfu titre of a viral solution are well known in the art.

Nucleic acid constructs associated with non-viral vectors may also be delivered in arty suitable dosage. Suitable doses are typically from 0.1 to 1000 µg of nucleic acid, for example 1 to 100 µg, 100 to 500 µg or 500 to 1000 µg, 1000 to 2000 µg, 2000 to 3000 µg or 3000 to 5000 µg. Preferred doses are in the-region of 5 to 50 µg, for example 10 to 20 µg.

For the delivery of Flexi-12 protein, suitable doses may be, for example, from 1 to 1000 µg, e.g. from 1 to 10 µg, from 10 to 100 µg or from 100 to 1000 µg. Where appropriate, B7 protein can be delivered at similar dosages.

For the purposes of cell therapy, any suitable dosage of transfected or transformed cells of the invention may be delivered.

Typically, from about $1\times10^4$ to about $1\times10^9$ cells are administered per dose, depending on clinical factors including the route of administration and the condition of the recipient. Preferred doses are in the region of $1\times10^6$ cells per dose.

Dosage schedules will also vary according to, for example, the route of administration, the species of the recipient and the condition of the recipient. However, single doses and multiple doses spread over periods of days, weeks or months are envisaged.

The present invention also provides methods of treating diseases involving uncontrolled proliferation of cells by administering effective non-toxic amounts of nucleic acid constructs, vectors, cells or fusion proteins of the invention to patients in need thereof.

Any proliferative disease that responds to IL-12 may be treated. In particular, tumours may be treated with a view to eliminating or reducing them. Such tumours include solid tumours and dispersed tumours, such as tumours of the blood, especially leukaemia. Other tumours which may be treated include renal, breast, colon, ovarian and cervical tumours, and melanomas.

Preferably, treatment is effected by delivering transformed or transfected cells of the invention, especially transformed or transfected leukaemia cells, in order to effect cell therapy.

The cells may be of any type that is compatible with the recipient's immune system. As with any transplantation of cells or tissue, the major tissue transplantation antigens of the adminstered cells will match the major tissue transplantation antigens of the recipient's cells.

Preferably the cells adminstered are derived from the recipient individual's is tumour, i.e. tumour cells may be removed from the intended recipient, transformed or transfected as appropriate then returned, in order to effect cell therapy. Alternatively, they may be derived from other individuals with compatible tissue transplantation antigens, such aa close relatives, Similarly, they may be HLA matched cells, e.g. HLA matched fibroblasts, which do not give rise to adverse immune reaction.

For the purposes of cell therapy, it is preferred to deliver the cells by intradermal or subcutaneous administration. A person of skill in the art will be able to choose an appropriate dosage i.e. the number and concentration of cells, to take into account the fact that only a limited volume of fluid may be adminstered in this manner.

Another preferred cell therapy technique is to deliver transfected fibroblast cells mixed with untransfected tumour cells, for example as demonstrated for rIL-12 by Tahara et al; 1994.

Where naked nucleic acid constructs are delivered, one preferred mode of administration is intramuscular. Preferably, a muscle-specific promoter is used. Typically, this will achieve systemic delivery of the expressed Flexi-12 protein or the B7 and Flexi-12 proteins as appropriate.

Where Flexi-12 protein is delivered, one preferred route of administration is intravenous, preferably with a view to achieving systemic delivery.

Vectors of the invention may also be delivered by any suitable means, preferably by local adminstration to the tumour to be treated, thereby to achieve gene therapy by delivering nucleic acid contructs of the invention to the tumour cells.

In general, proteins, vectors, constructs and cells of the invention may be delivered by any suitable route of administration e.g. by oral, rectal, nasal, topical, vaginal, or parenteral (including subcutaneous, intramuscular, intravenous or intradermal) adminstration. Delivery may be systemic or localised, e.g. to the tumour to be treated.

Where the construct encoders only Flexi-12, and not B7, B7 may be delivered separately, by any means of adminstration, as described above for Flexi-12. This also applies where Flexi-12 protein is delivered. Preferably, B7 is administered at the same time and in the same manner as Flexi-12 protein, though it could be adminstered separately.

All documents mentioned herein are incorporated by reference in their entirety.

The following Example illustrates the invention.

EXAMPLE

MATERIALS AND METHODS
Construction and Expression of Flexi-12.

The cDNA sequence and encoded amino acid sequences of human p35 SEQ ID No. 1) and p40 (SEQ ID No. 2) are given in FIGS. 8 and 9 respectively. The sequences are also given in Gately et al. The cDNA sequence and encoded amino acid, sequence of B7.1 is given in FIG. 10 (SEQ ID No. 5) and in Freeman et al was excised with Xho I and inserted into the Xho I site of pBK-CMV to give pCMV-35. The linker insert sequence was GAG CTC ATC TGC AGT GGT GGC GGT GGA AGC GGC GGT GGC GGA AGC GGC GGT GGC GGC AGC AGA AAC CTC CCC CTG GCC ATA CTA GT 3' (SEQ ID No. 15) and was made double stranded using Klenow fragment. This linker, after the relevant restriction digests detailed below, specifies the last two amino acids of the IL-12 p40 (Cys-Ser), the linker ([Gly-Gly-Gly-Gly-Ser]$_3$), an intervening hinge (Ala-Gly) then the first six amino acids of the IL-12 p35 subunit (Arg-Asn-Leu-Pro-Val-Ala) (SEQ ID No. 16). The linker was inserted into the Sac I/Spe I sites of pCMV 35 to give pCMV-linker-35. Clones were identified by hybridisation as described (Buluwela et al., 1989) and verified by sequencing. To bring the linker sequence and the p35 subunit in frame, pCMV-linker-35 was digested with Bal I, to give pCMV-linker-35-Bal. This also removes the signal peptide from the p35 subunit. This clone was verified by sequencing.

The cDNA for the human p40 subunit of IL-12 was excised from pBluescript with Xba I and Sac I and ligated into the Nhe I/Sac I sites of pBK-CMV to give pCMV-40. This was digested to completion with Xho I and partially digested with Pst I. pCMV-linker-35-Bal was digested to completion with Xho I and Pst I. This 864 bp fragment was ligated to pCMV-40 to give pCMV-Flexi-12. The linker portion of this clone was again verified by sequencing. This is shown schematically in FIG. 7.

Cell Culture and Transfection.

produce Flexi-12 gene product, COS-7 cells (ATCC CRL 1651) were established in AIM V serum free medium (Life Technologies, Paisley, Scotland). Prior to transfection, cells were split and 5×10$^4$ cells were allowed to reach 60–70% confluence in a 6 well plate. Cells were transfected with 5 μg DNA, prepared by Qiagen plasmid kit, (Qiagen Kent, England) using Lipofectin (Life Technologies, Paisley, Scotland) following manufacturers instructions. After 5 hours incubation at 37° C., the DNA/Lipofectin mixture was removed and replaced with fresh AIM V. Transfection efficiency was not assessed.

RT-PCRs.

Total RNA was isolated from 10$^6$ transfected COS-7 cells using the Qiagen RNeasy kit following the manufacturers instructions (Qiagen, Kent, England). The RNA was digested by 1 μg/ml DNase I at 37° C. for 60 minutes to remove any contaminating plasmid DNA. 2.5 μg total RNA was reverse transcribed into cDNA using random hexonmers. The cDNA was PCR amplified using the primers described below. Primers to amplify β-actin served as a control. The PCR was carried out for 30 cycles of 94° C. for 1 minute, 60° C. for 1 minute and 72° C. for 2 minutes. The PCR products were analysed by electrophoresis through either a 1% or 3% agarose gel. Oligonucleotides were:- β-actin 5'-TGC TAT CCA GGT TGT GCT AT-3' and 5'-GAT GGA GTT GAA GGT AGT TT-3'; (SEQ ID No. 17) p40 5' CTG TGA CAC CCC TGA AGA AGA TGG 3' (SEQ ID No. 18) and 5' ACG CAG AAT GTC AGG GAG AAG TAG G 3' (SEQ ID No. 19); Flexi-12 5' TCA GAG GGG ACA ACA AGG AGT ATG 3' (SEQ ID No. 20) and 5' GGA GTG GCC AGG GGG AGG TTT CT 3' (SEQ ID No. 21).

IL-12 and INF-γ ELISA ASSAYS.

ELISA kits were purchased from R+D Systems and used according to the manufacturer's instructions.

WESTERN BLOTS.

Western blots were performed as described (Sambrook et al., 1989). Briefly 1 ng IL-12 together with 50 μl supernatant from either Flexi-12 transfected or Mock transfected COS-7 cells were denatured by boiling for 2 minutes in the presence of 2.3% SDS and 0.75M β-mercaptoethanol. These samples were then run through a 10% SDS-polyacrylamide gel. Rainbow markers (Amersham International, Amersham, England) ranging from 14.3–200 kDa were also run. Proteins were transferred to a nitrocellulose membrane (Arnersham International, Amersham, England) and the membrane blocked by incubation in PBST buffer (PBS containing 0.05% Tween 20 (v/v) and 5% dried milk (w/v)), The filter was probed with polyclonal anti-IL-12 antibodies (R and D Systems, Oxford, England at 1:10 000 dilution). After three washes with PBST buffer, the membranes were incubated with peroxidase-conjugated rabbit anti-goat IgG antibody (DAKO Limited Denmark at 1:10 000 dilution) at room temperature. Signal was detected by enhanced chemiluminescence (ECL Amersham International, Amersham, England) according to the manufacturer's instructions.

Cell Proliferation Assays.

These were performed as described (Stern et al., 1990). Mononuclear cells from the peripheral blood of healthy donors were obtained by density gradient centrifugation on Lymphoprep (Nycomed, Oslo, Norway). These cells were then monocyte depleted by plastic adherence and the non-adherent cells suspended at $2\times10^6$ cells/ml in AIM-V serum free medium containing 2 µg/ml phytohaemagglutinin (PHA) (Sigma Chemical Co., Dorset, England) and cultured for 3 days. Cells were then split 1:1 with fresh AIM-V containing 20 IU/ml rIL-2 (Boehringer-Mannheim, Lewes, UK) and incubated for further 24 hours. The PHA blasts were then washed with RPMI pH 5.8 and then rested in RPMI/0.5% human AB serum for 4 hours. The cell concentration was adjusted to $2\times10^6$ cells/ml in AIM-V and 1 µg/ml of polyclonal neutralising anti-IL-2 (R+D Systems Oxford, England) was added to block IL-2 induced proliferation. These cells were demonstrated by FACS analysis to be>98% CD3+ T cells.

For the proliferation assay, 50 µl cell suspension was mixed with 50 µl of COS cell supernatant from either mock or Flexi-12 transfected COS cells. For comparison, rIL-12 was added in amounts equivalent to the measured amount of the Flexi-12. Dilutions of both Flexi-12 and rIL-12 were performed using mock supernatant. In experiments where neutralising anti-IL-12 antibodies were used, these were added to the supernatant prior to the addition of the supernatant to the cells. Proliferation was measured by MTT assay (Promega, Southampton, England) after 48 hours of culture.

Immunoprecipitation Assays.

These were performed as described (Bacon et al., 1995a). Briefly, PHA stimulated blasts were prepared as described above. Cells were collected by centrifugation, washed in PBS, lysed and incubated on ice for 30 minutes, Cleared lysates were obtained by centrifugation at 15000 g for 20 minutes. Protein-A conjugated sepharose beads (Pharmacia, Uppsala, Sweden) were incubated with anti-STAT 4 antibodies C-20 (Santa Cruz Biotechnology, California), for 3 hours at room temperature. Cell lysates were added to the beads and incubated overnight. The beads were washed 5 times and then the bound protein eluted from the beads by boiling for 5 minutes in the presence of 2.3% SDS and 0.75M β-mercaptoethanol. After cooling, the beads were removed by centrifugation and the sample loaded directly on to a SDS-polyacrylamide gel as described above. Filters were probed with anti-phosphotyrosine antibodies PY-20 (Santa Cruz Biotechnology, California, at 1:10 000 dilution) and after three washes as above, the membranes were incubated with peroxidase-conjugated goat anti-mouse IgG antibody (Santa Cruz Biotechnology, California at 1:10 000 dilution) at room temperature. Signal was detected by ECL. The blot was stripped with 100 mM β-mercaptoethanol, 2% SDS, 62.5 mM Tris-Cl pH 6.7 at 60° C. for 45 minutes. The blot was then reprobed with anti-STAT 4 antibodies L-18 (Santa Cruz Biotechnology, California), as above, after verifying that the blot had been completely stripped by using goat anti-mouse IgG antibody as described above.

Enhanced NK Activity of PBL.

NK cell-mediated cytotoxicity of the erythroleukaemic cell line K562 was performed as previously reported (Hatam et al., 1994). Effector PBLs were prepared as described (Chehimi et al., 1992). Briefly, PBLs were obtained as above and after monocyte depletion by plastic adherence, re-suspended at $5\times10^6$/ml in AIM V containing either 1 ng/ml Flexi-12, rIL-12 or an equal volume of mock transfected COS-7 cell supernatant, Target K562 cells ($5\times10^6$ cells in logarithmic growth phase) were washed in HBSS and resuspended in 0.5 ml labelling diluent (Sigma Chemical Co. Dorset, England). An equal volume of PKH26 at 1 mM in labelling diluent was added and the cells were incubated at room temperature for 2 minutes. The labelling was stopped by the addition of 0.5 ml foetal calf serum (Life Technologies, Paisley, Scotland) for 1 minute. The labelled cells were washed twice in RPMI 1640/10% FCS and resuspended at $10^6$/ml. 100 µl volumes of effector and target cells were co-incubated in triplicate in 12×75 mm polystyrene tubes at 37° C. and 5% $CO_2$ for four hours. Background target cell death was determined from tubes containing target cells alone. At the end of the incubation a period, 0.5 ml isotonic propidium iodide (5 µg/ml) was added to each tube and they were immediately analysed by flow cytometry (FACScan, Becton Dickinson UK Ltd, with Lysig II software). $10^4$ K562 target cells were acquired after live gating on PKH26 expression. Propidium iodide uptake was measured and the proportion of dead cells determined in each tube. The mean background cell death was determined from three replicate samples and this was subtracted from all other results to produce percent specific lysis.

RESULTS.

Flexi-12 Production From COS-7 Cells.

COS-7 cells were transfected with 5 µg Flexi-12 DNA. This was not done to achieve a stable transfectant but to produce supernatant containing the Flexi-12 gene product. Therefore aliquots of supernatant were assayed for IL-12 using a commercially available ELISA. 48 hours post transfection, 5.7±2.7 ng/ml (mean±SD; n=5) IL-12 was produced. The ELISA was unable to detect any IL-12 from the supernatant from the mock infected cells. The sensitivity of the ELISA is 7.8 pg/ml.

The regulation of IL-12 has recently been described (Murphy et al., 1995) and the p40 subunit has been considered the regulatory component of IL-12 expression (D'Andrea et al., 1992). In the Flexi-12 construct, the p35 cDNA is downstream of the p40 cDNA. It is possible that the p40 cDNA of the construct is being transcribed but the linker places the p35 subunit out of frame, The construct was sequenced but a mutation could have occurred in the bacterial preparation before the DNA was transfected into the COS-7 cells. As many cells have been reported to constitutively express IL-12 p35 mMNA (D'Andrea et al., 1992), the possibility of human IL-12 p40 and COS cell derived p35 creating a human/simian IL-12 hybrid was investigated. Several lines of evidence including RT-PCR and western blot analysis, suggest that this is not happening.

First, COS-7 cells were lysed and total RNA extracted. RT-PCR was performed as described above. Using primers specific for p35 that amplify both murine and human p35, simian COS-7 cells did not give a band but a specific band was seen with human 293 cells. Murine and human p35 are approximately 60% identical (Zou et al., 1995). Although this data does not preclude the possibility of a human/simian IL-12 hybrid, undetectable free p35 in COS-7 cells is encouraging.

Second, COS-7 cells were then transfected with either Flexi-12 or an IL-12 IRES construct (Anderson et al., 1995). Both cell populations were shown to be producing IL-12 by ELISA, then were lysed and total RNA extracted. RT-PCR was performed as described above. To verify that the PCR was distinguishing RNA rather than DNA, the actin control primers were chosen to span an intron, so that they would give different sized bands with each substrate. Using the RT product from Flexi-12, IRES-12 or mock transfected COS-7 cells, the primers give a specific 181 bp band (FIG. 1A Lanes A, B and C), However, with DNA extracted from normal human bone marrow, they give a 608 bp band (FIG. 1A Lane D). Molecular weight markers are designated in Lane M.

Using primers specific for p40, the RT products from both Flexi-12 and the IL-12 IRES transfected cells gave a specific band of 678 bp (FIG. 1B Lanes A and B respectively), whilst mock infected cells (FIG. 1B Lane C) gave no signal. By using primer pairs designed to include a primer specific for the linker/p35 junction region of the fusion protein, again with the RT products from both Flexi-12 and the IL-12 IRES transfected cells a specific band of 981 bp was only observed with the Flexi-12 transfected cells (FIG. 1B Lane E) and not with either IRES-12 transfected (FIG. 1B Lane D) or mock transfected (FIG. 1B Lane F).

Third, to verify that the Flexi-12 protein was a single 70–75 kDa band, Western blot analysis was performed on the COS-7 supernatant, Under the denaturing conditions used, 1 ng rIL-12 resolves into two bands corresponding to the previously reported 35 kDa and 40 kDa bands (FIG. 2 Lane A). The multiple close spaced bands of 35 kDa and 40 kDa are due to differential glycosylation of the two subunits by the Sf21 insect cells used to produce the rIL-12 (manufacturers data). A small amount of non-denatured p70 heterodimer can be seen. 100 µl and 50 µl mock transfected COS-7 cell supernatant (FIG. 2 Lanes B and C respectively) failed to show any bands with the anti-IL-12 polyclonal antibodies. In the lanes loaded with supernatant from Flexi-12 transfected COS-7 cells, 0.5 ng and 1 ng IL-12 equivalent (FIG. 2 Lanes D and E respectively) a single 70–75 kDa band was detected indicating that the Flexi-12 was produced as a single chain. No bands were detected that correspond to either the 35 kDa or 40 kDa subunits on over exposure of the gel, which indicates that transcription is complete along the Flexi-12 mRNA and no free p40 or p35 are produced from the construct.

PHA Blast Proliferation Assays.

After establishing that Flexi-12 construct was responsible for the IL-12 secreted from the COS-7 cells, the biological characteristics of Flexi-12 were investigated. One of the effects that IL-12 displays is its ability to induce the proliferation of PHA stimulated blasts. Therefore we prepared PHA stimulated blasts and exposed them for 48 hours to either rIL-12, Flexi-12 transfected or mock transfected COS-7 cell supernatant. The PHA blasts were phenotyped by flow cytometry and were >98% CD3+, <1% CD19+. FIG. 3 shows the effect of these additions to PHA blasts. Mock transfected COS-7 cell supernatant had no proliferative effect on PHA blasts, indeed it showed a mild inhibitory effect. Both rIL-12, diluted in mock supernatant, (dotted line, closed triangles) and Flexi-12 infected COS-7 cell supernatant (solid line, closed squares) showed a mitogenic effect on PHA blasts in a dose dependent manner. The results are expressed as the means ±SD of six independent experiments less the mean of unatimulated control cells. There is no significant difference between the results obtained with the rIL-12 and the Flexi-12. Both rIL-12 and Flexi-12 showed a proliferative effect at doses as low as 10 pg/ml (cf Stern et al., 1990 for rIL-12).

To demonstrate that this effect was due to IL-12 rather than any other secreted COS-7 cell protein, polyclonal neutralising antibodies were used to try to block this proliferation. This is also shown in FIG. 3. Addition of 10 µg/ml anti-IL-12 antibodies was able to prevent the proliferative effect of both the IL-12 (dotted lines, open triangles) and the Flexi-12 transfected COS-7 cell supernatant (solid line, open squares). Indeed, the anti-IL-12 antibodies prevented any proliferation with the Flexi-12 and only a very modest proliferation with the rIL-12. The addition of anti-IL-12 alone had no effect on baseline proliferation.

INF-γ Production Assays.

Another effect of IL-12 on activated T and NK cells is the induction of INF-γ. We therefore investigated whether PHA blasts incubated with either rIL-12, Flexi-12 transfected or mock transfected COS-7 cell supernatant could be induced to produce INF-γ. $10^6$ PHA blasts, as described above, were incubated for 36 hours in the presence of either rIL-12, Flexi-12 transfected or mock transfected COS-7 cell supernatant. This is shown in FIG. 4. Using 0.5 ng/ml IL-12 gave 186 ng/ml INF-γ and with 0.5 ng/ml Flexi-12 gave 160 ng/ml INF-γ and the mock supernatant gave 61 ng/ml INF-γ. These results are comparable to previous data where it was shown that 0.5–1 ng/ml IL-12, in the presence of 100 IU IL-2 could stimulate $10^6$ activated NK cells to produce 20–45 ng/ml of INF-γ (D'Andrea et al., 1992).

Flexi-12 Enhanced NK Activity.

The next biological characteristic of IL-12 that we investigated was the ability of IL-12 to enhance NK activity (Chehimi et al., 1992). Assays were performed to assess whether the Flexi-12 was capable of increasing the ability of IL-2 stimulated PBLs to lyse K562 targets. FIG. 5 shows the mean percent specific lysis for each effector cell culture system. Both rIL-12 and Flexi-12, (both at 1 ng/ml) gave enhanced killing of K562 compared to that seen with PBL incubated in mock supernatant.

STAT 4 Immunoprecipitation Assays.

Finally, we wanted to determine whether Flexi-12 was mediating its effects through the same receptor as rIL-12. It has been shown that after PHA activated T cells are exposed to rIL-12, tyrosine phosphorylation of JAK 2 and STAT 4 occurs (Bacon et al., 1995a; Bacon et al., 1995b). To determine whether Flexi-12 transfected COS-7 cell supernatant could induce tyrosine phosphorylation via STAT 4, $2\times10^7$ PHA activated T cells were exposed to either mock transfected cell supernatant or 1.0 ng/ml Flexi-12 in COS-7 transfected supernatant for 15 or 30 minutes (FIG. 6A, lanes B and C respectively) or 1.0 ng/ml rIL-12 in mock transfected COS-7 supernatant for 5, 15 and 30 minutes (FIG. 6A Lanes D, E and F respectively). The cell lysates were immunoprecipitated with anti-STAT 4 mAbs and the precipitates resolved by SDS-PAGE. Analyses were then performed by probing with an anti-phosphotyrosine antibody. As FIG. 7 Left hand panel shows, despite the added linker sequence of Flexi-12, binding is to the same receptor as IL-12 as evidenced by intercellular signalling via the same STAT 4 pathway. It has previously been shown (Bacon et al., 1995a; Bacon et al., 1995b), that tyrosine phosphorylation of STAT 4 increases after IL-12 binds to its receptor. Here we show that both rIL-12 and Flexi-12 increase the tyrosine phosphorylation of STAT4 in a time dependent manner. After stripping the blot of the anti-phosphotyrosine antibody, and subsequent checking that the signal had been lost, the filter was reprobed with another anti-STAT 4 antibody to verify that the loading was uniform across the gel. This is shown in FIG. 6B.

DISCUSSION

The biological activity of Flexi-12 was compared to rIL-12 in a series of assays. Both Flexi-12 and rIL-12 were able to induce the production of INF-γ from PHA blasts and the enhanced cytoxicity effects of Flexi-12 were similar to that seen with rIL-12 in our NK cytotoxicty assay. Indeed, the expression of Flexi-12 cDNA in COS-7 cells produces biologically active IL-12 at similar levels to that seen by retrovirally transformed fibroblasts (Tahara et al., 1994). Thus by the criteria used in these studies, the Flexi-12 possesses the same biological qualities as rIL-12.

Although the biological effects observed for Flexi-12 were the same as rIL-12, we were concerned that the addition of the linker might mediate binding to a different receptor than the naturally occurring cytokine. The transcription factor, Signal Transducers and Activators of Transcription (STAT 4) is expressed in haematopoietic tissue and it has recently been demonstrated that STAT 4 is a member of the IL-12 induced INF-γ response element (Bacon et al., 1995a). To date, only the binding of IL-12 to its receptor has been shown to induce tyrosine phosphorylation of STAT 4 in activated T cells. Consequently, we analysed the effects of rIL-12 and Flexi-12 on signalling via STAT 4. Both rIL-12 and Flexi-12 were able to induce tyrosine phosphorylation of STAT 4 in a time dependant manner indicating that both molecules are mediating their effects at a molecular level in the same manner in the cell.

These data demonstrate that Flexi-12 possesses similar biological activities to rIL-12. The fact that Flexi-12 is derived from a single cDNA means that there are several potential advantages for its use in immunotherapy protocols. By simplifying the production of IL-12 to a single polypeptide, viral vectors can also be simplified allowing the delivery of the cytokine to a tumour cell either in combination with a selectable marker or a co-stimulatory molecule in a manner that only requires the use of one IRES element. These simpler expression systems mean that there is both a reduced chance of recombination events and that the possibility of unregulated expression of the IL-12 p35 and p40 subunits is avoided. This ensures that no free homodimeric p40, an antagonist of p70 in the murine system, can be produced.

Construction of the Interleukin 12/B7.1 Gene Cassette

The cDNA encoding human B7.1 was cloned by PCR into the EcoRI/SalI sites of pUC 18 and verified against the published sequence by sequencing. pCITE-1 plasmid (Novagen Ltd.) containg the encephalomyocarditis virus 5' non coding region (containing the IRES element) was excised with PvuII/XbaI and inserted into the EcoRV/XbaI sites of modified pUC 18 described below. This plasmid was cleaved with NcoI/SalI and the NcoI/SalI fragment of B7.1 ligated in. To facilitate optimal expression downstream of an IRES element, it is important that the 11th AUG condon of the IRES is used to initiate translation. For expression of B7.1, this was acheived by removing the 12 base pairs between the 11th AUG of the IRES and the AUG condon of B7.1 leaving transcription in a perfect Kozak consensus sequence. This yielded pUC/CITE/B7.1.

The full Flexi-12/B7.1 construct was made by digesting pUC/CITE/B7.1 with AseI/PstI to release a 1.5 kbp CITE/B7.1 fragment, blunting this with T4 DNA polymerase and ligating into the blunted XhoI site of pCMV-Flexi, to yield pCMV-Flexi/CITE/B7.1. Digestion of this plasmid with SmaI NsiI and blunting with T4 DNA polymerase facilitated susequent cloning into AAV.

Recombinant AAV Plasmid Construction pUC 18 was modified by the insertion of a pair of linkers:- 5' CAT CGA TGG CCA GAT CTG ATA TCG ATG 3' (SEQ ID NO: 22) and 5' CAT GGT AGC TAC CGG TCT AGA CTA TAG CTA CCT AG 3' (SEQ ID No. 23) between the Kpn I/Barn HI sites to give an exteneded multiple cloning site with additional Cla I, Bal I, Bgl II and Eco Rv sites. This modification facilitated further manipulation. Wild type AAV, obtained from the American Type Culture Collection, was digested with Bgl II and this fragment cloned into the modified pUC18 to give pUC/AAB. Digestion of pUC/AAS with Dra III and NCo I removes the two gene rep and cap, essentially leaving the ITRs of the wild type virus, blunting the Dra III/Nco I ends with T4 DNA polymerase allows ligation of the CMV-Flexi/B7.1 plasmid (above) to yield pUC/AAV/Flexi/B7.1 (the vector plasmid).

ITR-free AAV (the helper plasmid) was obtained by sequential digest of the pUC/AAV with SnaBI and EcoRV to remove the 3' ITR and then Bal I and Sma I to remove the 5' ITR.

Generation of Recombinant AAV

The transformed human ernbryonal kidney cell line 293, in Earles modified MEM supplemented with 10% horse serum, were grown in 250 mm$^3$ tissue culture flasks to 70% confluency. 15 µg DNA at a helper to vector ratio of 3.1 (see above) was suspended in 1 ml. Opti-MEM (Life Technologies). Lipofectin (Life Technologies) was suspended in another 1 ml. aliquot of Opti-MEM such that the DNA/Lipofectin ratio was 1:4. The Opti-MEM was mixed by inversion and added to the cells after they had been washed with phosphate buffered saline. After 5 hours incubation at 37° C., the Opti-MEM was removed and replaced with complete medium containing wild type adenovirus type 5 at a concentration of 3–5 infectious units per cell. After 48 hours, or until 85% cytopathic effect was observed, rAAV was harvested by first pelleting the cells by centrifugation at 500 g for 10 minutes then resuspending the pellet in PBS. rAAV was released from the cells by three cycles of freezing and thawing. Contaminating adenovirus was inactivated by heating the lysate to 56° C. for 1 hour,

RESULTS

Expression of Flexi-12 and B7.1 from the Flexi-12/IRES/B7.1 plasmid construct after lipofection of the plasmid into COS-7 cells Interleukin 12 assay The supernatant of IL-12 plasmid-transfected tissue culture cells, in this case COS-7 cells, was assayed by a commercially available ELISA (Enzyme Linked Immuno-Sorbant Assay), in this case from R&D Systems.

Results are shown in the Table below, Columns A, B, C and D indicate the amount of IL-12 activity in four separate clones, whilst columns F, G, and H indicate the IL-12 activity of four controls using rIL-12 in the doses indicated. Column E is a control with the construct comprising Flexi-12 only and not B7.

| A | B | C | D | E | F | G | H |
| --- | --- | --- | --- | --- | --- | --- | --- |
| clone 1 | clone 2 | clone 4 | clone 7 | Flexi only | control 500 pg | control 250 pg | control 125 pg |
| 0.646 | 0.390 | 0.564 | 0.483 | 2.062 | 2.189 | 1.269 | 0.719 |

These data show that the cells transfected with the plasmid construct produce Flexi-12, and that Flexi-12 has IL-12 activity B7 expression This was assayed using a Fluorescent Activated Cell Scanner (FACS) machine. Cells were harvested then washed twice in Ranks Balanced Salt Solution prior to labelling in 12×75 mm round bottomed tubes (Falcon). After the final wash the cells were incubated for 15 minutes with the following monoclonal antibodies. 10 µl antiB7.1-FITC (Pharmingen). After incubation the cells were washed once in HBSS and then resuspended in FACSFlow (Becton Dickinson) prior to flow cytometric analysis (FACScan—Becton Dickinson). 10,000 viable cells as determined by light scatter were analysed from each sample using 3 colour flow cytometry.

A negative control was included which was cells that were mock transfected i.e. only empty plasmid was introduced to the cells. Expression of B7.1 was plotted as flow histograms for each sample.

In these histograms, the curves representing the four clones were right-shifted compared to the control, indicating that they have greater fluorescence, and therefore greater B7 content than the control. This demonstrates B7 expression.

These data show that the plasmid is capable of producing both secretable IL-12 and the surface expression of B7.1 The same calls that secrete IL-12 also express B7.1

Again, this was assayed using a Fluorescent Activated Cell Scanner (FACS) machine. Chinese Hamster Ovary (CHO) cells transfected with the empty plasmid pBK CMV or pBK CMV Flexi-B7-1 were grown in Ham's F12 medium (Gibco) on 9 cm tissue culture plates.

When the cells had reached 50% confluence monensin (Sigma) was added to the cultures at a final concentration of 3 uM and incubated for 12 hours at 37° C. and 5% $CO_2$. Cells were harvested then washed twice in Hanks Balanced Salt Solution prior to labelling in 12×75 mm round bottomed tubes (Falcon). After the final wash the cells were incubated for 15 minutes with 10 ul antiB71-FITC (pharmingen). After incubation the cells were washed once in HBSS and then resuspended in 500 ul of FACS Permeabilising solution (Becton Dickinson) and incubated for 10 minutes at room temperature in the dark. The cells were then washed in PBS+0.5% bovine serum albumin+0.1% sodium azide and then incubated for 30 minutes at room temperature in the dark with anti-IL-12-PE (Pharmingen) followed by a further washing step in PBS+0.5% BSA+0.1% sodium azide. After this washing step the cells were resuspended in PBS+1% paraformaldehyde before flow cytometric analysis (FACScan—Becton Dickinson). 10,000 viable cells as determined by light scatter were analysed from each sample. This was performed on CHO cells transfected with the empty plasmid as the negative control and CHO cells stably transfected with the pBK CMV Flex/B7-1 construct. Dot plots were then constructed with fluorescence intensity from IL-12 PE on the y axis and fluorescence intensity from B7-1 FITC on the x axis, demonstrating some individual cells expressing both intracellular IL-12 and surface B7-1.

Flexi-12 and B7 expression from the Flexi-12/IRES/B7.1 construct in AAV in leukaemic blasts (i.e. disease cells from patients, as distinct from cultive cell lines as above).

Interleukin 12 assay

The supernatant of IL-12 plasmid transfected COS-7 was assayed by a commercially available ELISA (Enzyme Linked Immuno-Sorbant Assay), in this case from R & D Systems. These data are from the same patient described below in respect of B7. The amount of IL-12 activity secreted from these AML blasts is about 100 times less than that from the COS cells but within the levels of detection of the ELISA. AAV-transfected leukaemic blasts transfected with the Flexi-12/IRES/B7 construct express Flexi-12 and show IL-12 activity.

B7 expression

Cells were incubated with AAV at an MOI (multiplicity of Infection) of 10–100:1 for 48 hours AAV adsorbs irreversibly to cells in suspension with 1–2 hours post infection, and uncoats in the nucleus soon after. Cells were in grown in Vancouver medium (MEM-Alpha supplemented with 12.5% foetal calf serum, 12.5% Horse serum, $10^{-4}$ M mercaptoethanol, 0.4 mg.ml glutamine, 0.04 g/ml Inositol, 0.01 mg/ml folic acid, $10^{-6}$ M hydrocortisone succinate), at a concentration of $10^5$ cells/ml with Stem Cell Factor at 20 ng/ml IL-3 at 10 ng/ml and GM-CSF at 10 ng/ml. 48 hours post incubation with AAV surface expression of B7.1 was assayed as described above suing a FACS scanner.

Again, the curve representing the transfected cells was right-shifted compared to the control curve, demonstrating that B7 expression occurred.

These data show that, like cells transformed with the plasmid vector, AAV-transfected cells also express B7 and Flexi-12, which has IL-12 activity.

REFERENCES

Anderson, R. J., Macdonald, I. D., Corbett, T. J., and Prentice, H. G. (1995). Adeno-Associated Virus Mediated Transfer Of Interleukin-12 to Human CD34+ Bone Marrow Derived Stem Cells. Experimental Haematology 23, 939 (Abstract)

Bacon, C. M., McVicar, D. W., Ortaldo, J. R., Rees, R. C., O'Shea, J. J., and Johnston, J. A. (1995a). Interleukin 12 (IL-12) induces tyrosine phosphorylation of JAK2 and TYK2: differential use of Janus family tyrosine kinases by IL-2 and IL-12. J. Ex. Med 181, 399–404.

Bacon, C. M., Petricoin, E. F., 3rd, Ortaldo, J. R., Rees, R. C., Larner, A. C., Johnston, JA, and O'Shea, J. J. (1995b). Interleukin 12 induces tyrosine phosphorylation and activation of STAT4 in human lymphocytes. Proc. Natl. Acad. Sci. USA. 92, 7307–7311.

Brunda, M. J., Luistro, L., Warrier, R. R., Wright, R. B., Hubbard, B. R., Murphy, M., Wolf, S. F., and Gately, M. K. (1993). Antitumor and antimetastatic activity of interleukin 12 against murine tumors. J. Ex. Med 178, 1223–1230.

Buluwela, L., Forster, A., Boehm, T., and Rabbitts, T. H. (1989). A rapid procedure for colony screening using nylon filters. Nuc. Acids Res. 17, 452.

Chehimi, J., Starr, S. E., Frank, I., Rengaraju, M., Jackson, S. J., Llanes, C., Kobayashi, M., Perussia, B., Young, D., Nickbarg, E., and et al. (1992). Natural killer (NK) cell stimulatory factor increases the cytotoxic activity of NK cells from both healthy donors and human immunodeficiency virus-infected patients. J. Ex. Med 175, 789–796.

D'Andrea, A., Rengaraju, M., Valiante, N. M., Chehimi, J., Kubin, M., Aste, M., Chan, S. H., Kobayashi, M., Young, D., Nickbarg, B., and et al. (1992). Production of natural killer cell stimulatory factor (interleukin 12) by peripheral blood mononuclear cells. J. Ex. Med 176, 1387–1398.

Freeman et al J. Immunol. Vol. 143, 2714–2722 No. 8 (1989). Gately, M. K., Desai, B. B., Wolitzky, A. G., Quinn, P. M., Dwyer, C. M., Podlaski, F. J., Familletti, P. C., Sinigaglia, F., Chizonnite, R., Gubler, U., and et al. (1991). Regulation of human lymphocyte proliferation by a heterodimeric cytokine, IL-12 (cytotoxic lymphocyte maturation factor). J. Immunol. 147, 874–882.

Gazzinelli, R. T., Hieny, S., Wynn, T. A., Wolf, S., and Sher, A. (1993). Interleukin 12 is required for the T-lymphocyte-independent induction of interferon gamma by an intracellular parasite and induces resistance in T-cell-deficient hosts. Proc. Natl. Acad. Sci. USA. 90, 6115–6119.

Ghattas, I. R., Sanes, J. R., and Majors, J. E. The encephalomyocarditis virus internal ribosome entry site allows efficient coexpression of two genes from a recombinant provirus in cultured cells and in embryos. molecular & cellular biology 11 (12):5848–5859.

Gubler, U., Chua, A. O., Schoenhaut, D. S., Dwyer, C. M., McComas, W., Motyka, R., Nabavi, N., Wolitzky, A. G., Quinn, P. M., Familletti, P. C., and et al. (1991). Coexpression of two distinct genes is required to generate secreted bioactive cytotoxic lymphocyte maturation factor. Proc. Natl. Acad. Sci. USA, 88, 4143–4147.

Hatam, L., Schuval, S., and Bonagura, V. R. (1994). Flow cytometric analysis of natural killer cell function as a clinical assay. Cytometry 26, 59–68.

Jang, S. K., Pestova, T. V., Hellen, C. U., Witherell, G. W., and Wimmer, E. Cap-independent translation of picornavirus RNAs: structure and function of the interal ribosomal entry site. [Review]. enzyme 44 (1–4): 292–309, 1990.

Kobayashi, M., Pitz, L., Ryan, M., Hewick, R. M., Clark, S. C., Chan, S., Loudon, R., Sherman, P., Perussia, B., and Trinchieri, G. (1989). Identification and purification of natural killer cell stimulatory factor (NKSF), a cytokine with multiple biologic effects on human lymphocytes. J. Ex. Med 170, 827–845.

Kubin, M,, Kamoun, M., and Trinchieri, G. (1994). Interleukin 12 synergizes with B7/CD28 interaction in inducing efficient proliferation and cytokine production of human T cells. J. Ex. Med 180, 211–222.

Manetti, R., Parronchi, P., Giudizi, M. G., Piccinni, M. P., Maggi, E., Trinchieri, G, and Romagnani, S. (1993). Natural killer cell stimulatory factor (interleukin 12 [IL-12]) induces T helper type 1 (Th1)-specific immune responses and inhibits the development of IL-4-producing Th cells. J. Ex. Med 177, 1199–1204.

Mattner, F., Fischer, S., Guckes, S., Jin, S., Kaulen, H, Schmitt, E., Rude, E., and Germann, T. (1993). The interleukin-12 subunit p40 specifically inhibits effects of the interleukin-12 heterodimer. Eur. J. Immunol. 23, 2202–2208.

Mu, J., Zou, J. P., Yamamoto, N., Tautsui, T., Tai, X. G., Kobayashi, M., Herrmann, S., Fujiwara, H., and Hamaoka, T. (1995). Administration of recombinint interleukin 12 prevents outgrowth of tumor cells metastasizing spontaneously to lung and lymph nodes. Cancer Res. 55, 4404–4408.

Murphy, E. E., Terres, G., Macatonia. S. E., Hsieh, C. S., Mattsont J., Lanier, L., Wysocka, M., Trinchieri, G., Murphy, K., and O'Garra, A. (1994). B7 and interleukin 12 cooperate for proliferation and interferon gamma production by mouse T helper clones that are unresponsive to B7 costimulation. J. Ex. Med 180, 223–231.

Murphy, T. L., Cleveland, M. G., Kulesza, P., Magram, J., and Murphy, K. M. (1995). Regulation of interleukin 12 p40 expression through an NF- kappa b half-site. Mol. Cell Biol. 15, 5258–5267.

Nastala, C. L., Edington, H. D., McKinney, T. G., Tahara, H., Nalesnik, M. A., Brunda, M. J., Gately, M. K., Wolf, S. F., Schreiber, R. D., Storkus, W. J., and et al (1994). Recombinant IL-12 administration induces tumor regression in association with IFN-gamma production. J. Immunol. 153, 1697–1706.

Sambrook, J., Fritsch, E. F., and Maniatis, T. (1989). Molecular Cloning A Laboratory Manual second Edition (Cold Spring Harbor Laboratory Press).

Scott, P. (1993). IL-12: initiation cytokine for cell-mediated immunity. Science 260, 496–497.

Stern, A. S., Podlaski, F. J., Hulmes, J. D., Pan, Y. C., Quinn, P. M., Wolitzky, A. G., Farnilletti, P. C., Stremlo, D. L., Truitt, T., Chizzonite, R., and et al. (1990). Purification to homogeneity and partial characterization of cytotoxic lymphocyte maturation factor from human B-lymphoblastoid cells. Proc. Natl. Acad. Sci. USA. 87, 6808–6812.

Sykes, M., Szot. G. L., Nguyen, P. L., and Pearson, D. A. (1995). Interleukin-12 inhibits murine graft-versus-host disease. Blood 86, 2429–2438.

Tahara, H., Zeh, H. J., 3rd, Storkus, W. J., Pappo, I., Watkins, S. C., Gubler, U., Wolf, S. F., Robbins, P. D., and Lotze, M. T. (1994). Fibroblasts genetically engineered to secrete interleukin 12 can suppress tumor growth and induce antitumor immunity to a murine melanoma in vivo. Cancer Res. 54, 182–189.

Tahara, H., Zitvogel, L., Storkus, W. J., Zeh, H. J., McKinney, T. G., Schreiber, R. D., Gublert U., Robbins, P. D., and Lotze, M. T. (1995). Effective eradication of established murine tumors with IL-12 gene therapy using a polycistronic retroviral vector. J. Immunol. 154, 6466–6474.

Wolf, S. F., Temple, P. A., Kobayashi, M., Young, D., Dicig, M., Lowe, L., Dzialo, R., Fitz, L., Ferenz, C., Hewick, R. M., and et al. (1991). Cloning of cDNA for natural killer cell stimulatory factor, a heterodimeric cytokine with multiple biologic effects on T and natural killer cells. J. Immunol. 146, 3074–3061.

Zitvogel, L., Tahara, H., Cai, Q., Storkus, W. J., Muller, G., Wolf, S. F., Gately, M., Robbins, P. D., and Lotze, M. T. (1994). Construction and characterization of retroviral vectors expressing biologically active human interleukin-12. Hum. Gene Ther. 5, 1493–1506.

Zou, J. J., Schoenhaut, D. S., Carvajal, D. M., Warrier, R. R., Presky, D. H., Gately, M. K., and Gubler, U. (1995). Structure-function analysis of the p35 subunit of mouse interleukin 12. J. Biol. Chem. 270, 5864–5871.

---

We claim:

1. A nucleic acid construct comprising a coding region encoding an interleukin-12 (IL-12) fusion protein, said fusion protein comprising: (a) an IL-12 p35 subunit; (b) an IL-12 p40 subunit; and (c) joining said subunits, a linker peptide, said construct further comprising a coding region encoding a B7 protein.

2. A nucleic acid construct according to claim 1 wherein, in the encoded fusion protein, the p35 coding sequence is C-terminal to the p40 coding sequence.

3. A nucleic acid construct according to claim 1 wherein, in the encoded fusion protein, the linker peptide comprises the sequence (Gly-Gly-Gly-Gly-Ser)n.

4. A nucleic acid construct according to claim 3 wherein n is 3 or 4.

5. A viral vector comprising a nucleic acid construct comprising a coding region encoding an interleukin-12 (IL-12) fusion protein, said fusion protein comprising: (a) an IL-12 p35 subunit; (b) an IL-12 p40 subunit, and (c) joining said subunits, a linker peptide, said construct further comprising a coding region encoding a B7 protein.

6. A viral vector according to claim 5 wherein, in the encoded fusion protein, the p35 subunit is C-terminal to the p40 coding sequence.

7. A viral vector according to claim 5 wherein, in the encoded fusion protein, the linker peptide comprises the sequence (Gly-Gly-Gly-Gly-Ser)n.

8. A viral vector according to claim 7 wherein n is 3 or 4.

9. A host cell transfected with a viral vector comprising a nucleic acid construct comprising a coding region encoding an interleukin-12 (IL-12) fusion protein said fusion protein comprising: (a) an IL-12 p35 subunit; (b) an IL-12 p40 subunit; and (c) joining said subunits, a linker peptide, said construct further comprising a coding region encoding a B7 protein.

10. A host cell according to claim 9 wherein, in the encoded fusion protein, the p35 subunit is C-terminal to the p40 coding sequence.

11. A host cell according to claim 9 wherein, in the encoded fusion protein, the linker peptide comprises the sequence (Gly-Gly-Gly-Gly-Ser)n.

12. A host cell according to claim 11 wherein n is 3 or 4.

13. A host cell according to claim 9 which is a mammalian cell.

14. A pharmaceutical composition comprising a viral vector comprising a nucleic acid construct, said construct comprising a coding region encoding an interleukin-12 (IL-12) fusion protein, said fusion protein comprising: (a) an IL-12 p35 subunit; (b) an IL-12 p40 subunit; and (c) joining said subunits, a linker peptide, said construct further comprising a coding region encoding a B7 protein; and a pharmaceutically acceptable carrier.

15. A pharmaceutical composition comprising a host cell transfected with a viral vector comprising a nucleic acid construct comprising a coding region encoding an interleukin-12 (IL-12) fusion protein, said fusion protein comprising: an IL-12 p35 subunit; (b) an IL-12 p40 subunit; and (c) joining said subunits a linker peptide, said construct further comprising a coding region encoding a B7 protein; and a pharmaceutically acceptable carrier.

* * * * *

SEQUENCE LISTING (1) GENERAL INFORMATION:

(iii) NUMBER OF SEQUENCES:80

(2) INFORMATION FOR SEQ ID NO: 1:

(i) SEQUENCE CHARACTERISTICS:
        (A) LENGTH: 1026 base pairs
        (B) TYPE: nucleic acid
        (C) STRANDEDNESS: double
        (D) TOPOLOGY: linear (ii) MOLECULE TYPE: cDNA (ix) FEATURE:
     (A) NAME/KEY: CDS
     (B) LOCATION:170..826

(xi) SEQUENCE DESCRIPTION: SEQ ID NO: 1:

```
GAATTCCCAG AAAGCAAGAG ACCAGAGTCC CGGGAAAGTC CTGCCGCGCC TCGGGACAAT      60

TATAAAATG TGGCCCCCTG GGTCAGCCTC CCAGCCACCG CCCTCACCTG CCGCGGCCAC      120

AGGTCTGCAT CCAGCGGCTC GCCCTGTGTC CTGCAGTGC CGGCTCAGC ATG TGT          175
                                                     Met Cys
                                                      1

CCA GCG CGC AGC CTC CTC CTT GTG GCT ACC CTG GTC CTC CTG GAC CAC      223
Pro Ala Arg Ser Leu Leu Leu Val Ala Thr Leu Val Leu Leu Asp His
        5                   10                  15

CTC AGT TTG GCC AGA AAC CTC CCC GTG GCC ACT CCA GAC CCA GGA ATG      271
Leu Ser Leu Ala Arg Asn Leu Pro Val Ala Thr Pro Asp Pro Gly Met
    20                  25                  30

TTC CCA TGC CTT CAC CAC TCC CAA AAC CTG CTG AGG GCC GTC AGC AAC      319
Phe Pro Cys Leu His His Ser Gln Asn Leu Leu Arg Ala Val Ser Asn
35                  40                  45                  50

ATG CTC CAG AAG GCC AGA CAA ACT CTA GAA TTT TAC CCT TGC ACT TCT      367
Met Leu Gln Lys Ala Arg Gln Thr Leu Glu Phe Tyr Pro Cys Thr Ser
                55                  60                  65

GAA GAG ATT GAT CAT GAA GAT ATC ACA AAA GAT AAA ACC AGC ACA GTG      415
Glu Glu Ile Asp His Glu Asp Ile Thr Lys Asp Lys Thr Ser Thr Val
            70                  75                  80

GAG GCC TGT TTA CCA TTG GAA TTA ACC AAG AAT GAG AGT TGC CTA AAT      463
Glu Ala Cys Leu Pro Leu Glu Leu Thr Lys Asn Glu Ser Cys Leu Asn
        85                  90                  95

TCC AGA GAG ACC TCT TTC ATA ACT AAT GGG AGT TGC CTG GCC TCC AGA      511
Ser Arg Glu Thr Ser Phe Ile Thr Asn Gly Ser Cys Leu Ala Ser Arg
    100                 105                 110

AAG ACC TCT TTT ATG ATG GCC CTG TGC CTT AGT AGT ATT TAT GAA GAC      559
Lys Thr Ser Phe Met Met Ala Leu Cys Leu Ser Ser Ile Tyr Glu Asp
115                 120                 125                 130

TTG AAG ATG TAC CAG GTG GAG TTC AAG ACC ATG AAT GCA AAG CTT CTG      607
Leu Lys Met Tyr Gln Val Glu Phe Lys Thr Met Asn Ala Lys Leu Leu
                135                 140                 145

ATG GAT CCT AAG AGG CAG ATC TTT CTA GAT CAA AAC ATG CTG GCA GTT      655
Met Asp Pro Lys Arg Gln Ile Phe Leu Asp Gln Asn Met Leu Ala Val
            150                 155                 160

ATT GAT GAG CTG ATG CAG GCC CTG AAT TTC AAC AGT GAG ACT GTG CCA      703
Ile Asp Glu Leu Met Gln Ala Leu Asn Phe Asn Ser Glu Thr Val Pro
        165                 170                 175

CAA AAA TCC TCC CTT GAA GAA CCG GAT TTT TAT AAA ACT AAA ATC AAG      751
Gln Lys Ser Ser Leu Glu Glu Pro Asp Phe Tyr Lys Thr Lys Ile Lys
    180                 185                 190

CTC TGC ATA CTT CTT CAT GCT TTC AGA ATT CGG GCA GTG ACT ATT GAC      799
Leu Cys Ile Leu Leu His Ala Phe Arg Ile Arg Ala Val Thr Ile Asp
195                 200                 205                 210

AGA GTG ACG AGC TAT CTG AAT GCT TCC TAAAAGCGA GGTCCCTCCA             846
Arg Val Thr Ser Tyr Leu Asn Ala Ser
                215

AACCGTTGTC ATTTTTATAA AACTTTGAAA TGAGGAAACT TGATAGGAT GTGGATTAAG     906

AACTAGGGAG GGGGAAAGAA GGATGGGACT ATTACATCCA CATGATACCT CTGATCAAGT    966

ATTTTTGACA TTTACTGTGG ATAAATTGTT TTTAAGTTTT CATGAATGAA TTGCTAAGAA    1026
```

(2) INFORMATION FOR SEQ ID NO: 2:

(i) SEQUENCE CHARACTERISTICS:

(A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO: 2:

Met Cys Pro Ala Arg Ser Leu Leu Leu Val Ala Thr Leu Val Leu Leu
 1               5                  10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
                100                 105                 110

Ser Arg Lys Thr Ser Phe Met Met Ala Leu Cys Leu Ser Ser Ile Tyr
            115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
                180                 185                 190

Ile Lys Leu Cys Ile Leu Leu His Ala Phe Arg Ile Arg Ala Val Thr
            195                 200                 205

Ile Asp Arg Val Thr Ser Tyr Leu Asn Ala Ser
    210                 215

(2) INFORMATION FOR SEQ ID NO: 3:

(i) SEQUENCE CHARACTERISTICS:
        (A) LENGTH: 1399 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION:43..1026

(xi) SEQUENCE DESCRIPTION: SEQ ID NO: 3:

CTGTTTCAGG GCCATTGGAC TCTCCGTCCT GCCCAGAGCA AG ATG TGT CAC CAG          54
                                             Met Cys His Gln
                                              220

CAG TTG GTC ATC TCT TGG TTT TCC CTG GTT TTT CTG GCA TCT CCC CTC        102
Gln Leu Val Ile Ser Trp Phe Ser Leu Val Phe Leu Ala Ser Pro Leu
    225                 230                 235

GTG GCC ATA TGG GAA CTG AAG AAA GAT GTT TAT GTC GTA GAA TTG GAT        150
Val Ala Ile Trp Glu Leu Lys Lys Asp Val Tyr Val Val Glu Leu Asp
240                 245                 250                 255

TGG TAT CCG GAT GCC CCT GGA GAA ATG GTG GTC CTC ACC TGT GAC ACC        198

```
Trp Tyr Pro Asp Ala Pro Gly Glu Met Val Val Leu Thr Cys Asp Thr
            260                 265                 270

CCT GAA GAA GAT GGT ATC ACC TGG ACC TTG GAC CAG AGC AGT GAG GTC         246
Pro Glu Glu Asp Gly Ile Thr Trp Thr Leu Asp Gln Ser Ser Glu Val
            275                 280                 285

TTA GGC TCT GGC AAA ACC CTG ACC ATC CAA GTC AAA GAG TTT GGA GAT         294
Leu Gly Ser Gly Lys Thr Leu Thr Ile Gln Val Lys Glu Phe Gly Asp
            290                 295                 300

GCT GGC CAG TAC ACC TGT CAC AAA GGA GGC GAG GTT CTA AGC CAT TCG         342
Ala Gly Gln Tyr Thr Cys His Lys Gly Gly Glu Val Leu Ser His Ser
        305                 310                 315

CTC CTG CTG CTT CAC AAA AAG GAA GAT GGA ATT TGG TCC ACT GAT ATT         390
Leu Leu Leu Leu His Lys Lys Glu Asp Gly Ile Trp Ser Thr Asp Ile
320                 325                 330                 335

TTA AAG GAC CAG AAA GAA CCC AAA AAT AAG ACC TTT CTA AGA TGC GAG         438
Leu Lys Asp Gln Lys Glu Pro Lys Asn Lys Thr Phe Leu Arg Cys Glu
            340                 345                 350

GCC AAG AAT TAT TCT GGA CGT TTC ACC TGC TGG TGG CTG ACG ACA ATC         486
Ala Lys Asn Tyr Ser Gly Arg Phe Thr Cys Trp Trp Leu Thr Thr Ile
            355                 360                 365

AGT ACT GAT TTG ACA TTC AGT GTC AAA AGC AGC AGA GGC TCT TCT GAC         534
Ser Thr Asp Leu Thr Phe Ser Val Lys Ser Ser Arg Gly Ser Ser Asp
            370                 375                 380

CCC CAA GGG GTG ACG TGC GGA GCT GCT ACA CTC TCT GCA GAG AGA GTC         582
Pro Gln Gly Val Thr Cys Gly Ala Ala Thr Leu Ser Ala Glu Arg Val
        385                 390                 395

AGA GGG GAC AAC AAG GAG TAT GAG TAC TCA GTG GAG TGC CAG GAG GAC         630
Arg Gly Asp Asn Lys Glu Tyr Glu Tyr Ser Val Glu Cys Gln Glu Asp
400                 405                 410                 415

AGT GCC TGC CCA GCT GCT GAG GAG AGT CTG CCC ATT GAG GTC ATG GTG         678
Ser Ala Cys Pro Ala Ala Glu Glu Ser Leu Pro Ile Glu Val Met Val
            420                 425                 430

GAT GCC GTT CAC AAG CTC AAG TAT GAA AAC TAC ACC AGC AGC TTC TTC         726
Asp Ala Val His Lys Leu Lys Tyr Glu Asn Tyr Thr Ser Ser Phe Phe
            435                 440                 445

ATC AGG GAC ATC ATC AAA CCT GAC CCA CCC AAG AAC TTG CAG CTG AAG         774
Ile Arg Asp Ile Ile Lys Pro Asp Pro Pro Lys Asn Leu Gln Leu Lys
            450                 455                 460

CCA TTA AAG AAT TCT CGG CAG GTG GAG GTC AGC TGG GAG TAC CCT GAC         822
Pro Leu Lys Asn Ser Arg Gln Val Glu Val Ser Trp Glu Tyr Pro Asp
465                 470                 475

ACC TGG AGT ACT CCA CAT TCC TAC TTC TCC CTG ACA TTC TGC GTT CAG         870
Thr Trp Ser Thr Pro His Ser Tyr Phe Ser Leu Thr Phe Cys Val Gln
480                 485                 490                 495

GTC CAG GGC AAG AGC AAG AGA GAA AAG AAA GAT AGA GTC TTC ACG GAC         918
Val Gln Gly Lys Ser Lys Arg Glu Lys Lys Asp Arg Val Phe Thr Asp
            500                 505                 510

AAG ACC TCA GCC ACG GTC ATC TGC CGC AAA AAT GCC AGC ATT AGC GTG         966
Lys Thr Ser Ala Thr Val Ile Cys Arg Lys Asn Ala Ser Ile Ser Val
            515                 520                 525

CGG GCC CAG GAC CGC TAC TAT AGC TCA TCT TGG AGC GAA TGG GCA TCT        1014
Arg Ala Gln Asp Arg Tyr Tyr Ser Ser Ser Trp Ser Glu Trp Ala Ser
            530                 535                 540

GTG CCC TGC AGT TAGGTTCTGA TCCAGGATGA AAATTTGGAG GAAAAGTGGA            1066
Val Pro Cys Ser
        545

AGATATTAAG CAAAATGTTT AAAGACACAA CGGAATAGAC CCAAAAAGAT AATTTCTATC      1126

TGATTTGCTT TAAAACGTTT TTTAGGATC ACAATGATAT CTTTGCTGTA TTTGTATAGT       1186

TAGATGCTAA ATGCTCATTG AAACAATCAG CTAATTTATG TATAGATTTT CCAGCTCTCA      1246
```

```
AGTTGCCATG GGCCTTCATG CTATTTAAAT ATTTAAGTAA TTTATGTATT TATTAGTATA      1306

TTACTGTTAT TTAACGTTTG TCTGCCAGGA TGTATGGAAT GTTTCATACT CTTATGACCT      1366

GATCCATCAG GATCAGTCCC TATTATGCAA AAT                                   1399
```

(2) INFORMATION FOR SEQ ID NO: 4:

(i) SEQUENCE CHARACTERISTICS:
        (A) LENGTH: 328 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Cys His Gln Gln Leu Val Ile Ser Trp Phe Ser Leu Val Phe Leu
 1               5                  10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
```

325

(2) INFORMATION FOR SEQ ID NO: 5:

(i) SEQUENCE CHARACTERISTICS:
        (A) LENGTH: 1491 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION:318..1181

(xi) SEQUENCE DESCRIPTION: SEQ ID NO: 5:

```
CCAAAGAAAA AGTGATTTGT CATTGCTTTA TAGACTGTAA GAAGAGAACA TCTCAGAAGT      60

GGAGTCTTAC CCTGAAATCA AAGGATTTAA AGAAAAAGTG GAATTTTTCT TCAGCAAGCT     120

GTGAAACTAA ATCCACAACC TTTGGAGACC CAGGAACACC CTCCAATCTC TGTGTGTTTT     180

GTAAACATCA CTGGAGGGTC TTCTACGTGA GCAATTGGAT TGTCATCAGC CCTGCCTGTT     240

TTGCACCTGG GAAGTGCCCT GGTCTTACTT GGGTCCAAAT TGTTGGCTTT CACTTTTGAC     300

CCTAAGCATC TGAAGCC ATG GGC CAC ACA CGG AGG CAG GGA ACA TCA CCA        350
                 Met Gly His Thr Arg Arg Gln Gly Thr Ser Pro
                         330                 335

TCC AAG TGT CCA TAC CTC AAT TTC TTT CAG CTC TTG GTG CTG GCT GGT       398
Ser Lys Cys Pro Tyr Leu Asn Phe Phe Gln Leu Leu Val Leu Ala Gly
340                 345                 350                 355

CTT TCT CAC TTC TGT TCA GGT GTT ATC CAC GTG ACC AAG GAA GTG AAA       446
Leu Ser His Phe Cys Ser Gly Val Ile His Val Thr Lys Glu Val Lys
                360                 365                 370

GAA GTG GCA ACG CTG TCC TGT GGT CAC AAT GTT TCT GTT GAA GAG CTG       494
Glu Val Ala Thr Leu Ser Cys Gly His Asn Val Ser Val Glu Glu Leu
                375                 380                 385

GCA CAA ACT CGC ATC TAC TGG CAA AAG GAG AAG AAA ATG GTG CTG ACT       542
Ala Gln Thr Arg Ile Tyr Trp Gln Lys Glu Lys Lys Met Val Leu Thr
                390                 395                 400

ATG ATG TCT GGG GAC ATG AAT ATA TGG CCC GAG TAC AAG AAC CGG ACC       590
Met Met Ser Gly Asp Met Asn Ile Trp Pro Glu Tyr Lys Asn Arg Thr
            405                 410                 415

ATC TTT GAT ATC ACT AAT AAC CTC TCC ATT GTG ATC CTG GCT CTG CGC       638
Ile Phe Asp Ile Thr Asn Asn Leu Ser Ile Val Ile Leu Ala Leu Arg
420                 425                 430                 435

CCA TCT GAC GAG GGC ACA TAC GAG TGT GTT GTT CTG AAG TAT GAA AAA       686
Pro Ser Asp Glu Gly Thr Tyr Glu Cys Val Val Leu Lys Tyr Glu Lys
                440                 445                 450

GAC GCT TTC AAG CGG GAA CAC CTG GCT GAA GTG ACG TTA TCA GTC AAA       734
Asp Ala Phe Lys Arg Glu His Leu Ala Glu Val Thr Leu Ser Val Lys
                455                 460                 465

GCT GAC TTC CCT ACA CCT AGT ATA TCT GAC TTT GAA ATT CCA ACT TCT       782
Ala Asp Phe Pro Thr Pro Ser Ile Ser Asp Phe Glu Ile Pro Thr Ser
            470                 475                 480

AAT ATT AGA AGG ATA ATT TGC TCA ACC TCT GGA GGT TTT CCA GAG CCT       830
Asn Ile Arg Arg Ile Ile Cys Ser Thr Ser Gly Gly Phe Pro Glu Pro
            485                 490                 495

CAC CTC TCC TGG TTG GAA AAT GGA GAA GAA TTA AAT GCC ATC AAC ACA       878
His Leu Ser Trp Leu Glu Asn Gly Glu Glu Leu Asn Ala Ile Asn Thr
500                 505                 510                 515

ACA GTT TCC CAA GAT CCT GAA ACT GAG CTC TAT GCT GTT AGC AGC AAA       926
Thr Val Ser Gln Asp Pro Glu Thr Glu Leu Tyr Ala Val Ser Ser Lys
                520                 525                 530
```

```
CTG GAT TTC AAT ATG ACA ACC AAC CAC AGC TTC ATG TGT CTC ATC AAG    974
Leu Asp Phe Asn Met Thr Thr Asn His Ser Phe Met Cys Leu Ile Lys
            535                 540                 545

TAT GGA CAT TTA AGA GTG AAT CAG ACC TTC AAC TGG AAT ACA ACC AAG   1022
Tyr Gly His Leu Arg Val Asn Gln Thr Phe Asn Trp Asn Thr Thr Lys
            550                 555                 560

CAA GAG CAT TTT CCT GAT AAC CTG CTC CCA TCC TGG GCC ATT ACC TTA   1070
Gln Glu His Phe Pro Asp Asn Leu Leu Pro Ser Trp Ala Ile Thr Leu
            565                 570                 575

ATC TCA GTA AAT GGA ATT TTT GTG ATA TGC TGC CTG ACC TAC TGC TTT   1118
Ile Ser Val Asn Gly Ile Phe Val Ile Cys Cys Leu Thr Tyr Cys Phe
580                 585                 590                 595

GCC CCA AGA TGC AGA GAG AGA AGG AGG AAT GAG AGA TTG AGA AGG GAA   1166
Ala Pro Arg Cys Arg Glu Arg Arg Arg Asn Glu Arg Leu Arg Arg Glu
                    600                 605                 610

AGT GTA CGC CCT GTA TAACAGTGTC CGCAGAAGCA AGGGGCTGAA AAGATCTGAA   1221
Ser Val Arg Pro Val
                615

GGTAGCCTCC GTCATCTCTT CTGGGATACA TGGATCGTGG GGATCATGAG GCATTCTTCC   1281

CTTAACAAAT TTAAGCTGTT TTACCCACTA CCTCACCTTC TTAAAAACCT CTTTCAGATT   1341

AAGCTGAACA GTTACAAGAT GGCTGGCATC CCTCTCCTTT CTCCCCATAT GCAATTTGCT   1401

TAATGTAACC TCTTCTTTTG CCATGTTTCC ATTCTGCCAT CTTGAATTGT CTTGTCAGCC   1461

AATTCATTAT CTATTAAACA CTAATTTGAG                                   1491

(2) INFORMATION FOR SEQ ID NO: 6:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO: 6:

Met Gly His Thr Arg Arg Gln Gly Thr Ser Pro Ser Lys Cys Pro Tyr
 1               5                  10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175
```

```
Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
            210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
            245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
            275                 280                 285

(2) INFORMATION FOR SEQ ID NO: 7:

(i) SEQUENCE CHARACTERISTICS:
        (A) LENGTH: 6139 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION:3222..4841

(xi) SEQUENCE DESCRIPTION: SEQ ID NO: 7:

GCACTTTTCG GGAAATGTGT CGCGGAACCC CTATTTGTTT ATTTTTCTAA ATACATTCAA    60

ATATGTATCC GCTCATGAGA CAATAACCCT GATAAATGCT TCAATAATAT TGAAAAGGA   120

AGAGTCCTGA GGCGGAAAGA ACCAGCTGTG AATGTGTGT CAGTTAGGGT GTGGAAAGTC   180

CCCAGGCTCC CCAGCAGGCA GAAGTATGCA AAGCATGCAT CTCAATTAGT CAGCAACCAG   240

GTGTGGAAAG TCCCCAGGCT CCCCAGCAGG CAGAAGTATG CAAAGCATGC ATCTCAATTA   300

GTCAGCAACC ATAGTCCCGC CCCTAACTCC GCCCATCCCG CCCCTAACTC CGCCCAGTTC   360

CGCCCATTCT CCGCCCCATG GCTGACTAAT TTTTTTTATT TATGCAGAGG CCGAGGCCGC   420

CTCGGCCTCT GAGCTATTCC AGAAGTAGTG AGGAGGCTTT TTTGGAGGCC TAGGCTTTTG   480

CAAAGATCGA TCAAGAGACA GGATGAGGAT CGTTTCGCAT GATTGAACAA GATGGATTGC   540

ACGCAGGTTC TCCGGCCGCT TGGGTGGAGA GGCTATTCGG CTATGACTGG GCACAACAGA   600

CAATCGGCTG CTCTGATGCC GCCGTGTTCC GGCTGTCAGC GCAGGGGCGC CCGGTTCTTT   660

TTGTCAAGAC CGACCTGTCC GGTGCCCTGA ATGAACTGCA AGACGAGGCA GCGCGGCTAT   720

CGTGGCTGGC CACGACGGGC GTTCCTTGCG CAGCTGTGCT CGACGTTGTC ACTGAAGCGG   780

GAAGGGACTG GCTGCTATTG GGCGAAGTGC CGGGGCAGGA TCTCCTGTCA TCTCACCTTG   840

CTCCTGCCGA GAAAGTATCC ATCATGGCTG ATGCAATGCG GCGGCTGCAT ACGCTTGATC   900

CGGCTACCTG CCCATTCGAC CACCAAGCGA AACATCGCAT CGAGCGAGCA CGTACTCGGA   960

TGGAAGCCGG TCTTGTCGAT CAGGATGATC TGGACGAAGA GCATCAGGGG CTCGCGCCAG  1020

CCGAACTGTT CGCCAGGCTC AAGGCGAGCA TGCCCGACGG CGAGGATCTC GTCGTGACCC  1080

ATGGCGATGC CTGCTTGCCG AATATCATGG TGGAAAATGG CCGCTTTTCT GGATTCATCG  1140

ACTGTGGCCG GCTGGGTGTG GCGGACCGCT ATCAGGACAT AGCGTTGGCT ACCCGTGATA  1200

TTGCTGAAGA GCTTGGCGGC GAATGGGCTG ACCGCTTCCT CGTGCTTTAC GGTATCGCCG  1260
```

```
CTCCCGATTC GCAGCGCATC GCCTTCTATC GCCTTCTTGA CGAGTTCTTC TGAGCGGGAC    1320
TCTGGGGTTC GAAATGACCG ACCAAGCGAC GCCCAACCTG CCATCACGAG ATTTCGATTC    1380
CACCGCCGCC TTCTATGAAA GGTTGGGCTT CGGAATCGTT TTCCGGGACG CCGGCTGGAT    1440
GATCCTCCAG CGCGGGATC TCATGCTGGA GTTCTTCGCC CACCCTAGGG GGAGGCTAAC    1500
TGAAACACGG AAGGAGACAA TACCGGAAGG AACCCGCGCT ATGACGGCAA TAAAAAGACA    1560
GAATAAAACG CACGGTGTTG GGTCGTTTGT TCATAAACGC GGGGTTCGGT CCCAGGGCTG    1620
GCACTCTGTC GATACCCCAC CGAGACCCCA TTGGGGCCAA TACGCCCGCG TTTCTTCCTT    1680
TTCCCCACCC CACCCCCCAA GTTCGGGTGA AGGCCCAGGG CTCGCAGCCA ACGTCGGGGC    1740
GGCAGGCCCT GCCATAGCCT CAGGTTACTC ATATATACTT TAGATTGATT TAAAACTTCA    1800
TTTTTAATTT AAAAGGATCT AGGTGAAGAT CCTTTTTGAT AATCTCATGA CCAAAATCCC    1860
TTAACGTGAG TTTTCGTTCC ACTGAGCGTC AGACCCCGTA GAAAAGATCA AAGGATCTTC    1920
TTGAGATCCT TTTTTTCTGC GCGTAATCTG CTGCTTGCAA ACAAAAAAAC CACCGCTACC    1980
AGCGGTGGTT TGTTTGCCGG ATCAAGAGCT ACCAACTCTT TTTCCGAAGG TAACTGGCTT    2040
CAGCAGAGCG CAGATACCAA ATACTGTCCT TCTAGTGTAG CCGTAGTTAG GCCACCACTT    2100
CAAGAACTCT GTAGCACCGC CTACATACCT CGCTCTGCTA ATCCTGTTAC CAGTGGCTGC    2160
TGCCAGTGGC GATAAGTCGT GTCTTACCGG GTTGGACTCA AGACGATAGT TACCGGATAA    2220
GGCGCAGCGG TCGGGCTGAA CGGGGGGTTC GTGCACACAG CCCAGCTTGG AGCGAACGAC    2280
CTACACCGAA CTGAGATACC TACAGCGTGA GCTATGAGAA AGCGCCACGC TTCCCGAAGG    2340
GAGAAAGGCG GACAGGTATC CGGTAAGCGG CAGGGTCGGA ACAGGAGAGC GCACGAGGGA    2400
GCTTCCAGGG GGAAACGCCT GGTATCTTTA TAGTCCTGTC GGGTTTCGCC ACCTCTGACT    2460
TGAGCGTCGA TTTTTGTGAT GCTCGTCAGG GGGCGGAGC CTATGGAAAA ACGCCAGCAA    2520
CGCGGCCTTT TTACGGTTCC TGGCCTTTTG CTGGCCTTTT GCTCACATGT TCTTTCCTGC    2580
GTTATCCCCT GATTCTGTGG ATAACCGTAT TACCGCCATG CATTAGTTAT TAATAGTAAT    2640
CAATTACGGG GTCATTAGTT CATAGCCCAT ATATGGAGTT CCGCGTTACA TAACTTACGG    2700
TAAATGGCCC GCCTGGCTGA CCGCCCAACG ACCCCCGCCC ATTGACGTCA ATAATGACGT    2760
ATGTTCCCAT AGTAACGCCA ATAGGGACTT TCCATTGACG TCAATGGGTG GAGTATTTAC    2820
GGTAAACTGC CCACTTGGCA GTACATCAAG TGTATCATAT GCCAAGTACG CCCCCTATTG    2880
ACGTCAATGA CGGTAAATGG CCCGCCTGGC ATTATGCCCA GTACATGACC TTATGGGACT    2940
TTCCTACTTG GCAGTACATC TACGTATTAG TCATCGCTAT TACCATGGTG ATGCGGTTTT    3000
GGCAGTACAT CAATGGGCGT GGATAGCGGT TTGACTCACG GGGATTTCCA AGTCTCCACC    3060
CCATTGACGT CAATGGGAGT TTGTTTTGGC ACCAAAATCA ACGGGACTTT CCAAAATGTC    3120
GTAACAACTC CGCCCCATTG ACGCAAATGG GCGGTAGGCG TGTACGGTGG GAGGTCTATA    3180
TAAGCAGAGC TGGTTTAGTG AACCGTCAGA TCCGCTAGAC C ATG GGT CAC CAG        3233
                                             Met Gly His Gln
                                              1
CAG TTG GTC ATC TCT TGG TTT TCC CTG GTT TTT CTG GCA TCT CCC CTC     3281
Gln Leu Val Ile Ser Trp Phe Ser Leu Val Phe Leu Ala Ser Pro Leu
  5              10                  15                  20
GTG GCC ATA TGG GAA CTG AAG AAA GAT GTT TAT GTC GTA GAA TTG GAT     3329
Val Ala Ile Trp Glu Leu Lys Lys Asp Val Tyr Val Val Glu Leu Asp
          25                  30                  35
TGG TAT CCG GAT GCC CCT GGA GAA ATG GTG GTC CTC ACC TGT GAC ACC     3377
Trp Tyr Pro Asp Ala Pro Gly Glu Met Val Val Leu Thr Cys Asp Thr
      40                  45                  50
```

| | | | | | | | | | | | | | | | | |
|---|---|---|---|---|---|---|---|---|---|---|---|---|---|---|---|---|
| CCT | GAA | GAA | GAT | GGT | ATC | ACC | TGG | ACC | TTG | GAC | CAG | AGC | AGT | GAG | GTC | 3425 |
| Pro | Glu | Glu | Asp | Gly | Ile | Thr | Trp | Thr | Leu | Asp | Gln | Ser | Ser | Glu | Val | |
| | | 55 | | | | 60 | | | | | 65 | | | | | |
| TTA | GGC | TCT | GGC | AAA | ACC | CTG | ACC | ATC | CAA | GTC | AAA | GAG | TTT | GGA | GAT | 3473 |
| Leu | Gly | Ser | Gly | Lys | Thr | Leu | Thr | Ile | Gln | Val | Lys | Glu | Phe | Gly | Asp | |
| 70 | | | | | 75 | | | | | 80 | | | | | | |
| GCT | GGC | CAG | TAC | ACC | TGT | CAC | AAA | GGA | GGC | GAG | GTT | CTA | AGC | CAT | TCG | 3521 |
| Ala | Gly | Gln | Tyr | Thr | Cys | His | Lys | Gly | Gly | Glu | Val | Leu | Ser | His | Ser | |
| 85 | | | | | 90 | | | | | 95 | | | | | 100 | |
| CTC | CTG | CTG | CTT | CAC | AAA | AAG | GAA | GAT | GGA | ATT | TGG | TCC | ACT | GAT | ATT | 3569 |
| Leu | Leu | Leu | Leu | His | Lys | Lys | Glu | Asp | Gly | Ile | Trp | Ser | Thr | Asp | Ile | |
| | | | | 105 | | | | | 110 | | | | | 115 | | |
| TTA | AAG | GAC | CAG | AAA | GAA | CCC | AAA | AAT | AAG | ACC | TTT | CTA | AGA | TGC | GAG | 3617 |
| Leu | Lys | Asp | Gln | Lys | Glu | Pro | Lys | Asn | Lys | Thr | Phe | Leu | Arg | Cys | Glu | |
| | | 120 | | | | 125 | | | | | 130 | | | | | |
| GCC | AAG | AAT | TAT | TCT | GGA | CGT | TTC | ACC | TGC | TGG | TGG | CTG | ACG | ACA | ATC | 3665 |
| Ala | Lys | Asn | Tyr | Ser | Gly | Arg | Phe | Thr | Cys | Trp | Trp | Leu | Thr | Thr | Ile | |
| | | 135 | | | | | 140 | | | | | 145 | | | | |
| AGT | ACT | GAT | TTG | ACA | TTC | AGT | GTC | AAA | AGC | AGC | AGA | GGC | TCT | TCT | GAC | 3713 |
| Ser | Thr | Asp | Leu | Thr | Phe | Ser | Val | Lys | Ser | Ser | Arg | Gly | Ser | Ser | Asp | |
| | 150 | | | | | 155 | | | | | 160 | | | | | |
| CCC | CAA | GGG | GTG | ACG | TGC | GGA | GCT | GCT | ACA | CTC | TCT | GCA | GAG | AGA | GTC | 3761 |
| Pro | Gln | Gly | Val | Thr | Cys | Gly | Ala | Ala | Thr | Leu | Ser | Ala | Glu | Arg | Val | |
| 165 | | | | 170 | | | | | 175 | | | | | 180 | | |
| AGA | GGG | GAC | AAC | AAG | GAG | TAT | GAG | TAC | TCA | GTG | GAG | TGC | CAG | GAG | GAC | 3809 |
| Arg | Gly | Asp | Asn | Lys | Glu | Tyr | Glu | Tyr | Ser | Val | Glu | Cys | Gln | Glu | Asp | |
| | | | | 185 | | | | | 190 | | | | | 195 | | |
| AGT | GCC | TGC | CCA | GCT | GCT | GAG | GAG | AGT | CTG | CCC | ATT | GAG | GTC | ATG | GTG | 3857 |
| Ser | Ala | Cys | Pro | Ala | Ala | Glu | Glu | Ser | Leu | Pro | Ile | Glu | Val | Met | Val | |
| | | | 200 | | | | | 205 | | | | | 210 | | | |
| GAT | GCC | GTT | CAC | AAG | CTC | AAG | TAT | GAA | AAC | TAC | ACC | AGC | AGC | TTC | TTC | 3905 |
| Asp | Ala | Val | His | Lys | Leu | Lys | Tyr | Glu | Asn | Tyr | Thr | Ser | Ser | Phe | Phe | |
| | | 215 | | | | | 220 | | | | | 225 | | | | |
| ATC | AGG | GAC | ATC | ATC | AAA | CCT | GAC | CCA | CCC | AAG | AAC | TTG | CAG | CTG | AAG | 3953 |
| Ile | Arg | Asp | Ile | Ile | Lys | Pro | Asp | Pro | Pro | Lys | Asn | Leu | Gln | Leu | Lys | |
| | 230 | | | | | 235 | | | | | 240 | | | | | |
| CCA | TTA | AAG | AAT | TCT | CGG | CAG | GTG | GAG | GTC | AGC | TGG | GAG | TAC | CCT | GAC | 4001 |
| Pro | Leu | Lys | Asn | Ser | Arg | Gln | Val | Glu | Val | Ser | Trp | Glu | Tyr | Pro | Asp | |
| 245 | | | | | 250 | | | | | 255 | | | | | 260 | |
| ACC | TGG | AGT | ACT | CCA | CAT | TCC | TAC | TTC | TCC | CTG | ACA | TTC | TGC | GTT | CAG | 4049 |
| Thr | Trp | Ser | Thr | Pro | His | Ser | Tyr | Phe | Ser | Leu | Thr | Phe | Cys | Val | Gln | |
| | | | | 265 | | | | | 270 | | | | | 275 | | |
| GTC | CAG | GGC | AAG | AGC | AAG | AGA | GAA | AAG | AAA | GAT | AGA | GTC | TTC | ACG | GAC | 4097 |
| Val | Gln | Gly | Lys | Ser | Lys | Arg | Glu | Lys | Lys | Asp | Arg | Val | Phe | Thr | Asp | |
| | | | 280 | | | | | 285 | | | | | 290 | | | |
| AAG | ACC | TCA | GCC | ACG | GTC | ATC | TGC | CGC | AAA | AAT | GCC | AGC | ATT | AGC | GTG | 4145 |
| Lys | Thr | Ser | Ala | Thr | Val | Ile | Cys | Arg | Lys | Asn | Ala | Ser | Ile | Ser | Val | |
| | | 295 | | | | | 300 | | | | | 305 | | | | |
| CGG | GCC | CAG | GAC | CGC | TAC | TAT | AGC | TCA | TCT | TGG | AGC | GAA | TGG | GCA | TCT | 4193 |
| Arg | Ala | Gln | Asp | Arg | Tyr | Tyr | Ser | Ser | Ser | Trp | Ser | Glu | Trp | Ala | Ser | |
| | 310 | | | | | 315 | | | | | 320 | | | | | |
| GTG | CCC | TGC | AGT | GGT | GGC | GGT | GGA | AGC | GGC | GGT | GGC | GGA | AGC | GGC | GGT | 4241 |
| Val | Pro | Cys | Ser | Gly | Gly | Gly | Gly | Ser | Gly | Gly | Gly | Gly | Ser | Gly | Gly | |
| 325 | | | | | 330 | | | | | 335 | | | | | 340 | |
| GGC | GGC | AGC | AGA | AAC | CTC | CCC | CTG | GCC | ACT | CCA | GAC | CCA | GGA | ATG | TTC | 4289 |
| Gly | Gly | Ser | Arg | Asn | Leu | Pro | Leu | Ala | Thr | Pro | Asp | Pro | Gly | Met | Phe | |
| | | | | 345 | | | | | 350 | | | | | 355 | | |
| CCA | TGC | CTT | CAC | CAC | TCC | CAA | AAC | CTG | CTG | AGG | GCC | GTC | AGC | AAC | ATG | 4337 |
| Pro | Cys | Leu | His | His | Ser | Gln | Asn | Leu | Leu | Arg | Ala | Val | Ser | Asn | Met | |
| | | | 360 | | | | | 365 | | | | | 370 | | | |

-continued

```
CTC CAG AAG GCC AGA CAA ACT CTA GAA TTT TAC CCT TGC ACT TCT GAA    4385
Leu Gln Lys Ala Arg Gln Thr Leu Glu Phe Tyr Pro Cys Thr Ser Glu
        375                 380                 385

GAG ATT GAT CAT GAA GAT ATC ACA AAA GAT AAA ACC AGC ACA GTG GAG    4433
Glu Ile Asp His Glu Asp Ile Thr Lys Asp Lys Thr Ser Thr Val Glu
390                 395                 400

GCC TGT TTA CCA TTG GAA TTA ACC AAG AAT GAG AGT TGC CTA AAT TCC    4481
Ala Cys Leu Pro Leu Glu Leu Thr Lys Asn Glu Ser Cys Leu Asn Ser
405                 410                 415                 420

AGA GAG ACC TCT TTC ATA ACT AAT GGG AGT TGC CTG GCC TCC AGA AAG    4529
Arg Glu Thr Ser Phe Ile Thr Asn Gly Ser Cys Leu Ala Ser Arg Lys
                425                 430                 435

ACC TCT TTT ATG ATG GCC CTG TGC CTT AGT AGT ATT TAT GAA GAC TTG    4577
Thr Ser Phe Met Met Ala Leu Cys Leu Ser Ser Ile Tyr Glu Asp Leu
            440                 445                 450

AAG ATG TAC CAG GTG GAG TTC AAG ACC ATG AAT GCA AAG CTT CTG ATG    4625
Lys Met Tyr Gln Val Glu Phe Lys Thr Met Asn Ala Lys Leu Leu Met
            455                 460                 465

GAT CCT AAG AGG CAG ATC TTT CTA GAT CAA AAC ATG CTG GCA GTT ATT    4673
Asp Pro Lys Arg Gln Ile Phe Leu Asp Gln Asn Met Leu Ala Val Ile
        470                 475                 480

GAT GAG CTG ATG CAG GCC CTG AAT TTC AAC AGT GAG ACT GTG CCA CAA    4721
Asp Glu Leu Met Gln Ala Leu Asn Phe Asn Ser Glu Thr Val Pro Gln
485                 490                 495                 500

AAA TCC TCC CTT GAA GAA CCG GAT TTT TAT AAA ACT AAA ATC AAG CTC    4769
Lys Ser Ser Leu Glu Glu Pro Asp Phe Tyr Lys Thr Lys Ile Lys Leu
                505                 510                 515

TGC ATA CTT CTT CAT GCT TTC AGA ATT CGG GCA GTG ACT ATT GAC AGA    4817
Cys Ile Leu Leu His Ala Phe Arg Ile Arg Ala Val Thr Ile Asp Arg
            520                 525                 530

GTG ACG AGC TAT CTG AAT GCT TCC TAAAAAGCGA GGTCCCTCCA AACCGTTGTC    4871
Val Thr Ser Tyr Leu Asn Ala Ser
            535                 540

ATTTTTATAA AACTTTGAAA TGAGGAAACT TGATAGGAT GTGGATTAAG AACTAGGGAG    4931

GGGGAAAGAA GGATGGGACT ATTACATCCA CATGATACCT CTGATCAAGT ATTTTTGACA    4991

TTTACTGTGG ATAAATTGTT TTTAAGTTTT CATGAATGAA TTGCTAAGAA GGGGGGAATT    5051

CTTTTGCTTT TTACCCTCGA GAGTACTTCT AGAGCGGCCG CGGGCCCATC GATTTTCCAC    5111

CCGGGTGGGG TACCAGGTAA GTGTACCCAA TTCGCCCTAT AGTGAGTCGT ATTACAATTC    5171

ACTGGCCGTC GTTTTACAAC GTCGTGACTG GGAAAACCCT GGCGTTACCC AACTTAATCG    5231

CCTTGCAGCA CATCCCCCTT TCGCCAGCTG GCGTAATAGC GAAGAGGCCC GCACCGATCG    5291

CCCTTCCCAA CAGTTGCGCA GCCTGAATGG CGAATGGAGA TCCAATTTTT AAGTGTATAA    5351

TGTGTTAAAC TACTGATTCT AATTGTTTGT GTATTTTAGA TTCACAGTCC CAAGGCTCAT    5411

TTCAGGCCCC TCAGTCCTCA CAGTCTGTTC ATGATCATAA TCAGCCATAC CACATTTGTA    5471

GAGGTTTTAC TTGCTTTAAA AAACCTCCCA CACCTCCCCC TGAACCTGAA ACATAAAATG    5531

AATGCAATTG TTGTTGTTAA CTTGTTTATT GCAGCTTATA ATGGTTACAA ATAAAGCAAT    5591

AGCATCACAA ATTTCACAAA TAAAGCATTT TTTTCACTGC ATTCTAGTTG TGGTTTGTCC    5651

AAACTCATCA ATGTATCTTA ACGCGTAAAT TGTAAGCGTT AATATTTTGT TAAAATTCGC    5711

GTTAAATTTT TGTTAAATCA GCTCATTTTT TAACCAATAG GCCGAAATCG GCAAAATCCC    5771

TTATAAATCA AAAGAATAGA CCGAGATAGG GTTGAGTGTT GTTCCAGTTT GGAACAAGAG    5831

TCCACTATTA AGAACGTGG ACTCCAACGT CAAAGGGCGA AAAACCGTCT ATCAGGGCGA    5891

TGGCCCACTA CGTGAACCAT CACCCTAATC AAGTTTTTTG GGGTCGAGGT GCCGTAAAGC    5951
```

```
ACTAAATCGG AACCCTAAAG GGAGCCCCCG ATTTAGAGCT TGACGGGGAA AGCCGGCGAA    6011

CGTGGCGAGA AAGGAAGGGA AGAAAGCGAA AGGAGCGGGC GCTAGGGCGC TGGCAAGTGT    6071

AGCGGTCACG CTGCGCGTAA CCACCACACC CGCCGCGCTT AATGCGCCGC TACAGGGCGC    6131

GTCAGGTG                                                              6139
```

(2) INFORMATION FOR SEQ ID NO: 8:

(i) SEQUENCE CHARACTERISTICS:
        (A) LENGTH: 540 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Gly His Gln Gln Leu Val Ile Ser Trp Phe Ser Leu Val Phe Leu
  1               5                  10                  15

Ala Ser Pro Leu Val Ala Ile Trp Glu Leu Lys Lys Asp Val Tyr Val
             20                  25                  30

Val Glu Leu Asp Trp Tyr Pro Asp Ala Pro Gly Glu Met Val Val Leu
         35                  40                  45

Thr Cys Asp Thr Pro Glu Glu Asp Gly Ile Thr Trp Thr Leu Asp Gln
 50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
             100                 105                 110

Ser Thr Asp Ile Leu Lys Asp Gln Lys Glu Pro Lys Asn Lys Thr Phe
         115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320
```

```
Glu Trp Ala Ser Val Pro Cys Ser Gly Gly Gly Ser Gly Gly Gly
            325                 330                 335

Gly Ser Gly Gly Gly Ser Arg Asn Leu Pro Leu Ala Thr Pro Asp
            340                 345                 350

Pro Gly Met Phe Pro Cys Leu His Ser Gln Asn Leu Leu Arg Ala
            355                 360                 365

Val Ser Asn Met Leu Gln Lys Ala Arg Gln Thr Leu Glu Phe Tyr Pro
370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415

Cys Leu Asn Ser Arg Glu Thr Ser Phe Ile Thr Asn Gly Ser Cys Leu
                420                 425                 430

Ala Ser Arg Lys Thr Ser Phe Met Met Ala Leu Cys Leu Ser Ser Ile
                435                 440                 445

Tyr Glu Asp Leu Lys Met Tyr Gln Val Glu Phe Lys Thr Met Asn Ala
            450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
                485                 490                 495

Thr Val Pro Gln Lys Ser Ser Leu Glu Glu Pro Asp Phe Tyr Lys Thr
                500                 505                 510

Lys Ile Lys Leu Cys Ile Leu Leu His Ala Phe Arg Ile Arg Ala Val
            515                 520                 525

Thr Ile Asp Arg Val Thr Ser Tyr Leu Asn Ala Ser
            530                 535                 540

(2) INFORMATION FOR SEQ ID NO: 9:

(i) SEQUENCE CHARACTERISTICS:
        (A) LENGTH: 1623 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION:1..1620

(xi) SEQUENCE DESCRIPTION: SEQ ID NO: 9:

ATG GGT CAC CAG CAG TTG GTC ATC TCT TGG TTT TCC CTG GTT TTT CTG      48
Met Gly His Gln Gln Leu Val Ile Ser Trp Phe Ser Leu Val Phe Leu
            2050                2055                2060

GCA TCT CCC CTC GTG GCC ATA TGG GAA CTG AAG AAA GAT GTT TAT GTC      96
Ala Ser Pro Leu Val Ala Ile Trp Glu Leu Lys Lys Asp Val Tyr Val
            2065                2070                2075

GTA GAA TTG GAT TGG TAT CCG GAT GCC CCT GGA GAA ATG GTG GTC CTC     144
Val Glu Leu Asp Trp Tyr Pro Asp Ala Pro Gly Glu Met Val Val Leu
            2080                2085                2090

ACC TGT GAC ACC CCT GAA GAA GAT GGT ATC ACC TGG ACC TTG GAC CAG     192
Thr Cys Asp Thr Pro Glu Glu Asp Gly Ile Thr Trp Thr Leu Asp Gln
            2095                2100                2105

AGC AGT GAG GTT TTA GGC TCT GGC AAA ACC CTG ACC ATC CAA GTC AAA     240
Ser Ser Glu Val Leu Gly Ser Gly Lys Thr Leu Thr Ile Gln Val Lys
2110                2115                2120                2125

GAG TTT GGA GAT GCT GGC CAG TAC ACC TGT CAC AAA GGA GGC GAG GTT     288
```

```
Glu Phe Gly Asp Ala Gly Gln Tyr Thr Cys His Lys Gly Glu Val
                2130                2135                2140

CTA AGC CAT TCG CTC CTG CTT CAC AAA AAG GAA GAT GGA ATT TGG        336
Leu Ser His Ser Leu Leu Leu His Lys Lys Glu Asp Gly Ile Trp
                2145                2150                2155

TCC ACT GAT ATT TTA AAG GAC CAG AAA GAA CCC AAA AAT AAG ACC TTT    384
Ser Thr Asp Ile Leu Lys Asp Gln Lys Glu Pro Lys Asn Lys Thr Phe
            2160                2165                2170

CTA AGA TGC GAG GCC AAG AAT TAT TCT GGA CGT TTC ACC TGC TGG TGG    432
Leu Arg Cys Glu Ala Lys Asn Tyr Ser Gly Arg Phe Thr Cys Trp Trp
        2175                2180                2185

CTG ACG ACA ATC AGT ACT GAT TTG ACA TTC AGT GTC AAA AGC AGC AGA    480
Leu Thr Thr Ile Ser Thr Asp Leu Thr Phe Ser Val Lys Ser Ser Arg
2190                2195                2200                2205

GGC TCT TCT GAC CCC CAA GGG GTG ACG TGC GGA GCT GCT ACA CTC TCT    528
Gly Ser Ser Asp Pro Gln Gly Val Thr Cys Gly Ala Ala Thr Leu Ser
            2210                2215                2220

GCA GAG AGA GTC AGA GGG GAC AAC AAG GAG TAT GAG TAC TCA GTG GAG    576
Ala Glu Arg Val Arg Gly Asp Asn Lys Glu Tyr Glu Tyr Ser Val Glu
        2225                2230                2235

TGC CAG GAG GAC AGT GCC TGC CCA GCT GCT GAG GAG AGT CTG CCC ATT    624
Cys Gln Glu Asp Ser Ala Cys Pro Ala Ala Glu Glu Ser Leu Pro Ile
            2240                2245                2250

GAG GTC ATG GTG GAT GCC GTT CAC AAG CTC AAG TAT GAA AAC TAC ACC    672
Glu Val Met Val Asp Ala Val His Lys Leu Lys Tyr Glu Asn Tyr Thr
        2255                2260                2265

AGC AGC TTC TTC ATC AGG GAC ATC ATC AAA CCT GAC CCA CCC AAG AAC    720
Ser Ser Phe Phe Ile Arg Asp Ile Ile Lys Pro Asp Pro Pro Lys Asn
2270                2275                2280                2285

TTG CAG CTG AAG CCA TTA AAG AAT TCT CGG CAG GTG GAG GTC AGC TGG    768
Leu Gln Leu Lys Pro Leu Lys Asn Ser Arg Gln Val Glu Val Ser Trp
            2290                2295                2300

GAG TAC CCT GAC ACC TGG AGT ACT CCA CAT TCC TAC TTC TCC CTG ACA    816
Glu Tyr Pro Asp Thr Trp Ser Thr Pro His Ser Tyr Phe Ser Leu Thr
        2305                2310                2315

TTC TGC GTT CAG GTC CAG GGC AAG AGC AAG AGA GAA AAG AAA GAT AGA    864
Phe Cys Val Gln Val Gln Gly Lys Ser Lys Arg Glu Lys Lys Asp Arg
        2320                2325                2330

GTC TTC ACG GAC AAG ACC TCA GCC ACG GTC ATC TGC CGC AAA AAT GCC    912
Val Phe Thr Asp Lys Thr Ser Ala Thr Val Ile Cys Arg Lys Asn Ala
        2335                2340                2345

AGC ATT AGC GTG CGG GCC CAG GAC CGC TAC TAT AGC TCA TCT TGG AGC    960
Ser Ile Ser Val Arg Ala Gln Asp Arg Tyr Tyr Ser Ser Ser Trp Ser
2350                2355                2360                2365

GAA TGG GCA TCT GTG CCC TGC AGT GGT GGC GGT GGA AGC GGC GGT GGC   1008
Glu Trp Ala Ser Val Pro Cys Ser Gly Gly Gly Gly Ser Gly Gly Gly
            2370                2375                2380

GGA AGC GGC GGT GGC GGC AGC AGA AAC CTC CCC CTG GCC ACT CCA GAC   1056
Gly Ser Gly Gly Gly Gly Ser Arg Asn Leu Pro Leu Ala Thr Pro Asp
        2385                2390                2395

CCA GGA ATG TTC CCA TGC CTT CAC CAC TCC CAA AAC CTG CTG AGG GCC   1104
Pro Gly Met Phe Pro Cys Leu His His Ser Gln Asn Leu Leu Arg Ala
        2400                2405                2410

GTC AGC AAC ATG CTC CAG AAG GCC AGA CAA ACT CTA GAA TTT TAC CCT   1152
Val Ser Asn Met Leu Gln Lys Ala Arg Gln Thr Leu Glu Phe Tyr Pro
        2415                2420                2425

TGC ACT TCT GAA GAG ATT GAT CAT GAA GAT ATC ACA AAA GAT AAA ACC   1200
Cys Thr Ser Glu Glu Ile Asp His Glu Asp Ile Thr Lys Asp Lys Thr
2430                2435                2440                2445

AGC ACA GTG GAG GCC TGT TTA CCA TTG GAA TTA ACC AAG AAT GAG AGT   1248
```

```
Ser Thr Val Glu Ala Cys Leu Pro Leu Glu Leu Thr Lys Asn Glu Ser
            2450                2455                2460

TGC CTA AAT TCC AGA GAG ACC TCT TTC ATA ACT AAT GGG AGT TGC CTG      1296
Cys Leu Asn Ser Arg Glu Thr Ser Phe Ile Thr Asn Gly Ser Cys Leu
            2465                2470                2475

GCC TCC AGA AAG ACC TCT TTT ATG ATG GCC CTG TGC CTT AGT AGT ATT      1344
Ala Ser Arg Lys Thr Ser Phe Met Met Ala Leu Cys Leu Ser Ser Ile
            2480                2485                2490

TAT GAA GAC TTG AAG ATG TAC CAG GTG GAG TTC AAG ACC ATG AAT GCA      1392
Tyr Glu Asp Leu Lys Met Tyr Gln Val Glu Phe Lys Thr Met Asn Ala
            2495                2500                2505

AAG CTT CTG ATG GAT CCT AAG AGG CAG ATC TTT CTA GAT CAA AAC ATG      1440
Lys Leu Leu Met Asp Pro Lys Arg Gln Ile Phe Leu Asp Gln Asn Met
2510                2515                2520                2525

CTG GCA GTT ATT GAT GAG CTG ATG CAG GCC CTG AAT TTC AAC AGT GAG      1488
Leu Ala Val Ile Asp Glu Leu Met Gln Ala Leu Asn Phe Asn Ser Glu
            2530                2535                2540

ACT GTG CCA CAA AAA TCC TCC CTT GAA GAA CCG GAT TTT TAT AAA ACT      1536
Thr Val Pro Gln Lys Ser Ser Leu Glu Glu Pro Asp Phe Tyr Lys Thr
            2545                2550                2555

AAA ATC AAG CTC TGC ATA CTT CTT CAT GCT TTC AGA ATT CGG GCA GTG      1584
Lys Ile Lys Leu Cys Ile Leu Leu His Ala Phe Arg Ile Arg Ala Val
            2560                2565                2570

ACT ATT GAC AGA GTG ACG AGC TAT CTG AAT GCT TCC TAA                  1623
Thr Ile Asp Arg Val Thr Ser Tyr Leu Asn Ala Ser
            2575                2580                2585

(2) INFORMATION FOR SEQ ID NO: 10:

(i) SEQUENCE CHARACTERISTICS:
        (A) LENGTH: 540 amino acids
        (B) TYPE: amino acid
        (D) TOPOLOGY: linear (ii) MOLECULE TYPE: protein (xi) SEQUENCE DESCRIPTION: SEQ ID NO: 10:

Met Gly His Gln Gln Leu Val Ile Ser Trp Phe Ser Leu Val Phe Leu
 1               5                  10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175
```

```
Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly
                325                 330                 335

Gly Ser Gly Gly Gly Gly Ser Arg Asn Leu Pro Leu Ala Thr Pro Asp
            340                 345                 350

Pro Gly Met Phe Pro Cys Leu His His Ser Gln Asn Leu Leu Arg Ala
            355                 360                 365

Val Ser Asn Met Leu Gln Lys Ala Arg Gln Thr Leu Glu Phe Tyr Pro
    370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415

Cys Leu Asn Ser Arg Glu Thr Ser Phe Ile Thr Asn Gly Ser Cys Leu
            420                 425                 430

Ala Ser Arg Lys Thr Ser Phe Met Met Ala Leu Cys Leu Ser Ser Ile
        435                 440                 445

Tyr Glu Asp Leu Lys Met Tyr Gln Val Glu Phe Lys Thr Met Asn Ala
450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
                485                 490                 495

Thr Val Pro Gln Lys Ser Ser Leu Glu Glu Pro Asp Phe Tyr Lys Thr
            500                 505                 510

Lys Ile Lys Leu Cys Ile Leu Leu His Ala Phe Arg Ile Arg Ala Val
        515                 520                 525

Thr Ile Asp Arg Val Thr Ser Tyr Leu Asn Ala Ser
530                 535                 540

(2) INFORMATION FOR SEQ ID NO: 11:

(i) SEQUENCE CHARACTERISTICS:
        (A) LENGTH: 1560 base pairs
        (B) TYPE: nucleic acid
        (C) STRANDEDNESS: double
        (D) TOPOLOGY: linear (ii) MOLECULE TYPE: cDNA
```

(ix) FEATURE:
    (A) NAME/KEY: CDS
    (B) LOCATION:1..1557

(xi) SEQUENCE DESCRIPTION: SEQ ID NO: 11:

| | | | | | | | | | | | | | | | |
|---|---|---|---|---|---|---|---|---|---|---|---|---|---|---|---|
| GCC | ATA | TGG | GAA | CTG | AAG | AAA | GAT | GTT | TAT | GTC | GTA | GAA | TTG | GAT | TGG | 48 |
| Ala | Ile | Trp | Glu | Leu | Lys | Lys | Asp | Val | Tyr | Val | Val | Glu | Leu | Asp | Trp |
|  |  |  |  | 545 |  |  |  | 550 |  |  |  | 555 |  |  |  |

```
GCC ATA TGG GAA CTG AAG AAA GAT GTT TAT GTC GTA GAA TTG GAT TGG      48
Ala Ile Trp Glu Leu Lys Lys Asp Val Tyr Val Val Glu Leu Asp Trp
                545                 550                 555

TAT CCG GAT GCC CCT GGA GAA ATG GTG GTC CTC ACC TGT GAC ACC CCT      96
Tyr Pro Asp Ala Pro Gly Glu Met Val Val Leu Thr Cys Asp Thr Pro
                560                 565                 570

GAA GAA GAT GGT ATC ACC TGG ACC TTG GAC CAG AGC AGT GAG GTC TTA     144
Glu Glu Asp Gly Ile Thr Trp Thr Leu Asp Gln Ser Ser Glu Val Leu
            575                 580                 585

GGC TCT GGC AAA ACC CTG ACC ATC CAA GTC AAA GAG TTT GGA GAT GCT     192
Gly Ser Gly Lys Thr Leu Thr Ile Gln Val Lys Glu Phe Gly Asp Ala
            590                 595                 600

GGC CAG TAC ACC TGT CAC AAA GGA GGC GAG GTT CTA AGC CAT TCG CTC     240
Gly Gln Tyr Thr Cys His Lys Gly Gly Glu Val Leu Ser His Ser Leu
605                 610                 615                 620

CTG CTG CTT CAC AAA AAG GAA GAT GGA ATT TGG TCC ACT GAT ATT TTA     288
Leu Leu Leu His Lys Lys Glu Asp Gly Ile Trp Ser Thr Asp Ile Leu
                625                 630                 635

AAG GAC CAG AAA GAA CCC AAA AAT AAG ACC TTT CTA AGA TGC GAG GCC     336
Lys Asp Gln Lys Glu Pro Lys Asn Lys Thr Phe Leu Arg Cys Glu Ala
            640                 645                 650

AAG AAT TAT TCT GGA CGT TTC ACC TGC TGG TGG CTG ACG ACA ATC AGT     384
Lys Asn Tyr Ser Gly Arg Phe Thr Cys Trp Trp Leu Thr Thr Ile Ser
            655                 660                 665

ACT GAT TTG ACA TTC AGT GTC AAA AGC AGC AGA GGC TCT TCT GAC CCC     432
Thr Asp Leu Thr Phe Ser Val Lys Ser Ser Arg Gly Ser Ser Asp Pro
            670                 675                 680

CAA GGG GTG ACG TGC GGA GCT GCT ACA CTC TCT GCA GAG AGA GTC AGA     480
Gln Gly Val Thr Cys Gly Ala Ala Thr Leu Ser Ala Glu Arg Val Arg
685                 690                 695                 700

GGG GAC AAC AAG GAG TAT GAG TAC TCA GTG GAG TGC CAG GAG GAC AGT     528
Gly Asp Asn Lys Glu Tyr Glu Tyr Ser Val Glu Cys Gln Glu Asp Ser
                705                 710                 715

GCC TGC CCA GCT GCT GAG GAG AGT CTG CCC ATT GAG GTC ATG GTG GAT     576
Ala Cys Pro Ala Ala Glu Glu Ser Leu Pro Ile Glu Val Met Val Asp
            720                 725                 730

GCC GTT CAC AAG CTC AAG TAT GAA AAC TAC ACC AGC AGC TTC TTC ATC     624
Ala Val His Lys Leu Lys Tyr Glu Asn Tyr Thr Ser Ser Phe Phe Ile
            735                 740                 745

AGG GAC ATC ATC AAA CCT GAC CCA CCC AAG AAC TTG CAG CTG AAG CCA     672
Arg Asp Ile Ile Lys Pro Asp Pro Pro Lys Asn Leu Gln Leu Lys Pro
            750                 755                 760

TTA AAG AAT TCT CGG CAG GTG GAG GTC AGC TGG GAG TAC CCT GAC ACC     720
Leu Lys Asn Ser Arg Gln Val Glu Val Ser Trp Glu Tyr Pro Asp Thr
765                 770                 775                 780

TGG AGT ACT CCA CAT TCC TAC TTC TCC CTG ACA TTC TGC GTT CAG GTC     768
Trp Ser Thr Pro His Ser Tyr Phe Ser Leu Thr Phe Cys Val Gln Val
                785                 790                 795

CAG GGC AAG AGC AAG AGA GAA AAG AAA GAT AGA GTC TTC ACG GAC AAG     816
Gln Gly Lys Ser Lys Arg Glu Lys Lys Asp Arg Val Phe Thr Asp Lys
            800                 805                 810

ACC TCA GCC ACG GTC ATC TGC CGC AAA AAT GCC AGC ATT AGC GTG CGG     864
Thr Ser Ala Thr Val Ile Cys Arg Lys Asn Ala Ser Ile Ser Val Arg
            815                 820                 825

GCC CAG GAC CGC TAC TAT AGC TCA TCT TGG AGC GAA TGG GCA TCT GTG     912
Ala Gln Asp Arg Tyr Tyr Ser Ser Ser Trp Ser Glu Trp Ala Ser Val
```

-continued

| | | | | | | | | | | | | | | |
|---|---|---|---|---|---|---|---|---|---|---|---|---|---|---|
| | 830 | | | 835 | | | | 840 | | | | | | |
| CCC | TGC | AGT | GGT | GGC | GGT | GGA | AGC | GGC | GGT | GGC | GGA | AGC | GGC | GGT | GGC | 960 |
| Pro | Cys | Ser | Gly | Gly | Gly | Gly | Ser | Gly | Gly | Gly | Gly | Ser | Gly | Gly | Gly | |
| 845 | | | | 850 | | | | 855 | | | | | 860 | | | |

| GGC | AGC | AGA | AAC | CTC | CCC | CTG | GCC | ACT | CCA | GAC | CCA | GGA | ATG | TTC | CCA | 1008 |
| Gly | Ser | Arg | Asn | Leu | Pro | Leu | Ala | Thr | Pro | Asp | Pro | Gly | Met | Phe | Pro | |
| | | | | 865 | | | | 870 | | | | | 875 | | | |

| TGC | CTT | CAC | CAC | TCC | CAA | AAC | CTG | CTG | AGG | GCC | GTC | AGC | AAC | ATG | CTC | 1056 |
| Cys | Leu | His | His | Ser | Gln | Asn | Leu | Leu | Arg | Ala | Val | Ser | Asn | Met | Leu | |
| | | | 880 | | | | | 885 | | | | | 890 | | | |

| CAG | AAG | GCC | AGA | CAA | ACT | CTA | GAA | TTT | TAC | CCT | TGC | ACT | TCT | GAA | GAG | 1104 |
| Gln | Lys | Ala | Arg | Gln | Thr | Leu | Glu | Phe | Tyr | Pro | Cys | Thr | Ser | Glu | Glu | |
| | | 895 | | | | 900 | | | | | 905 | | | | | |

| ATT | GAT | CAT | GAA | GAT | ATC | ACA | AAA | GAT | AAA | ACC | AGC | ACA | GTG | GAG | GCC | 1152 |
| Ile | Asp | His | Glu | Asp | Ile | Thr | Lys | Asp | Lys | Thr | Ser | Thr | Val | Glu | Ala | |
| | 910 | | | | 915 | | | | | 920 | | | | | | |

| TGT | TTA | CCA | TTG | GAA | TTA | ACC | AAG | AAT | GAG | AGT | TGC | CTA | AAT | TCC | AGA | 1200 |
| Cys | Leu | Pro | Leu | Glu | Leu | Thr | Lys | Asn | Glu | Ser | Cys | Leu | Asn | Ser | Arg | |
| 925 | | | | 930 | | | | | 935 | | | | | 940 | | |

| GAG | ACC | TCT | TTC | ATA | ACT | AAT | GGG | AGT | TGC | CTG | GCC | TCC | AGA | AAG | ACC | 1248 |
| Glu | Thr | Ser | Phe | Ile | Thr | Asn | Gly | Ser | Cys | Leu | Ala | Ser | Arg | Lys | Thr | |
| | | | | 945 | | | | | 950 | | | | | 955 | | |

| TCT | TTT | ATG | ATG | GCC | CTG | TGC | CTT | AGT | AGT | ATT | TAT | GAA | GAC | TTG | AAG | 1296 |
| Ser | Phe | Met | Met | Ala | Leu | Cys | Leu | Ser | Ser | Ile | Tyr | Glu | Asp | Leu | Lys | |
| | | | 960 | | | | | 965 | | | | | 970 | | | |

| ATG | TAC | CAG | GTG | GAG | TTC | AAG | ACC | ATG | AAT | GCA | AAG | CTT | CTG | ATG | GAT | 1344 |
| Met | Tyr | Gln | Val | Glu | Phe | Lys | Thr | Met | Asn | Ala | Lys | Leu | Leu | Met | Asp | |
| | | 975 | | | | | 980 | | | | | 985 | | | | |

| CCT | AAG | AGG | CAG | ATC | TTT | CTA | GAT | CAA | AAC | ATG | CTG | GCA | GTT | ATT | GAT | 1392 |
| Pro | Lys | Arg | Gln | Ile | Phe | Leu | Asp | Gln | Asn | Met | Leu | Ala | Val | Ile | Asp | |
| | 990 | | | | | 995 | | | | | 1000 | | | | | |

| GAG | CTG | ATG | CAG | GCC | CTG | AAT | TTC | AAC | AGT | GAG | ACT | GTG | CCA | CAA | AAA | 1440 |
| Glu | Leu | Met | Gln | Ala | Leu | Asn | Phe | Asn | Ser | Glu | Thr | Val | Pro | Gln | Lys | |
| 1005 | | | | 1010 | | | | | 1015 | | | | | 1020 | | |

| TCC | TCC | CTT | GAA | GAA | CCG | GAT | TTT | TAT | AAA | ACT | AAA | ATC | AAG | CTC | TGC | 1488 |
| Ser | Ser | Leu | Glu | Glu | Pro | Asp | Phe | Tyr | Lys | Thr | Lys | Ile | Lys | Leu | Cys | |
| | | | | 1025 | | | | | 1030 | | | | | 1035 | | |

| ATA | CTT | CTT | CAT | GCT | TTC | AGA | ATT | CGG | GCA | GTG | ACT | ATT | GAC | AGA | GTG | 1536 |
| Ile | Leu | Leu | His | Ala | Phe | Arg | Ile | Arg | Ala | Val | Thr | Ile | Asp | Arg | Val | |
| | | | 1040 | | | | | 1045 | | | | | 1050 | | | |

| ACG | AGC | TAT | CTG | AAT | GCT | TCC | TAA | | | | | | | | | 1560 |
| Thr | Ser | Tyr | Leu | Asn | Ala | Ser | | | | | | | | | | |
| | | | 1055 | | | | | | | | | | | | | |

(2) INFORMATION FOR SEQ ID NO: 12:

(i) SEQUENCE CHARACTERISTICS:
        (A) LENGTH: 519 amino acids
        (B) TYPE: amino acid
        (D) TOPOLOGY: linear (ii) MOLECULE TYPE: protein (xi) SEQUENCE DESCRIPTION: SEQ ID NO: 12:

| Ala | Ile | Trp | Glu | Leu | Lys | Lys | Asp | Val | Tyr | Val | Val | Glu | Leu | Asp | Trp |
|---|---|---|---|---|---|---|---|---|---|---|---|---|---|---|---|
| 1 | | | | 5 | | | | | 10 | | | | | 15 | |

| Tyr | Pro | Asp | Ala | Pro | Gly | Glu | Met | Val | Val | Leu | Thr | Cys | Asp | Thr | Pro |
| | | | 20 | | | | | 25 | | | | | 30 | | |

| Glu | Glu | Asp | Gly | Ile | Thr | Trp | Thr | Leu | Asp | Gln | Ser | Ser | Glu | Val | Leu |
| | | | 35 | | | | | 40 | | | | | 45 | | |

| Gly | Ser | Gly | Lys | Thr | Leu | Thr | Ile | Gln | Val | Lys | Glu | Phe | Gly | Asp | Ala |

```
                50                  55                  60
Gly Gln Tyr Thr Cys His Lys Gly Gly Glu Val Leu Ser His Ser Leu
 65                  70                  75                  80

Leu Leu Leu His Lys Lys Glu Asp Gly Ile Trp Ser Thr Asp Ile Leu
                 85                  90                  95

Lys Asp Gln Lys Glu Pro Lys Asn Lys Thr Phe Leu Arg Cys Glu Ala
                100                 105                 110

Lys Asn Tyr Ser Gly Arg Phe Thr Cys Trp Trp Leu Thr Thr Ile Ser
                115                 120                 125

Thr Asp Leu Thr Phe Ser Val Lys Ser Ser Arg Gly Ser Ser Asp Pro
130                 135                 140

Gln Gly Val Thr Cys Gly Ala Ala Thr Leu Ser Ala Glu Arg Val Arg
145                 150                 155                 160

Gly Asp Asn Lys Glu Tyr Glu Tyr Ser Val Glu Cys Gln Glu Asp Ser
                165                 170                 175

Ala Cys Pro Ala Ala Glu Glu Ser Leu Pro Ile Glu Val Met Val Asp
                180                 185                 190

Ala Val His Lys Leu Lys Tyr Glu Asn Tyr Thr Ser Ser Phe Phe Ile
                195                 200                 205

Arg Asp Ile Ile Lys Pro Asp Pro Pro Lys Asn Leu Gln Leu Lys Pro
210                 215                 220

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
                245                 250                 255

Gln Gly Lys Ser Lys Arg Glu Lys Lys Asp Arg Val Phe Thr Asp Lys
                260                 265                 270

Thr Ser Ala Thr Val Ile Cys Arg Lys Asn Ala Ser Ile Ser Val Arg
                275                 280                 285

Ala Gln Asp Arg Tyr Tyr Ser Ser Ser Trp Ser Glu Trp Ala Ser Val
290                 295                 300

Pro Cys Ser Gly Gly Gly Ser Gly Gly Gly Ser Gly Gly Gly
305                 310                 315                 320

Gly Ser Arg Asn Leu Pro Leu Ala Thr Pro Asp Pro Gly Met Phe Pro
                325                 330                 335

Cys Leu His His Ser Gln Asn Leu Leu Arg Ala Val Ser Asn Met Leu
                340                 345                 350

Gln Lys Ala Arg Gln Thr Leu Glu Phe Tyr Pro Cys Thr Ser Glu Glu
                355                 360                 365

Ile Asp His Glu Asp Ile Thr Lys Asp Lys Thr Ser Thr Val Glu Ala
370                 375                 380

Cys Leu Pro Leu Glu Leu Thr Lys Asn Glu Ser Cys Leu Asn Ser Arg
385                 390                 395                 400

Glu Thr Ser Phe Ile Thr Asn Gly Ser Cys Leu Ala Ser Arg Lys Thr
                405                 410                 415

Ser Phe Met Met Ala Leu Cys Leu Ser Ser Ile Tyr Glu Asp Leu Lys
                420                 425                 430

Met Tyr Gln Val Glu Phe Lys Thr Met Asn Ala Lys Leu Leu Met Asp
                435                 440                 445

Pro Lys Arg Gln Ile Phe Leu Asp Gln Asn Met Leu Ala Val Ile Asp
                450                 455                 460

Glu Leu Met Gln Ala Leu Asn Phe Asn Ser Glu Thr Val Pro Gln Lys
465                 470                 475                 480
```

```
Ser Ser Leu Glu Glu Pro Asp Phe Tyr Lys Thr Lys Ile Lys Leu Cys
            485                 490                 495

Ile Leu Leu His Ala Phe Arg Ile Arg Ala Val Thr Ile Asp Arg Val
        500                 505                 510

Thr Ser Tyr Leu Asn Ala Ser
        515
```

(2) INFORMATION FOR SEQ ID NO: 13:

(i) SEQUENCE CHARACTERISTICS:
        (A) LENGTH: 61 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION:1..61

(xi) SEQUENCE DESCRIPTION: SEQ ID NO: 13:

```
GGT GGC GGT GGA AGC GGC GGT GGC GGA AGC GGC GGT GGC GGC AGC AGA      48
Gly Gly Gly Gly Ser Gly Gly Gly Gly Ser Gly Gly Gly Gly Ser Arg
520                 525                 530                 535

AAC CTC CCC CTG  G                                                   61
Asn Leu Pro Leu
```

(2) INFORMATION FOR SEQ ID NO: 14:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 14:

```
Gly Gly Gly Gly Ser Gly Gly Gly Ser Gly Gly Gly Gly Ser Arg
 1               5                  10                  15

Asn Leu Pro Leu
        20
```

(2) INFORMATION FOR SEQ ID NO: 15:

(i) SEQUENCE CHARACTERISTICS:
        (A) LENGTH: 77 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 15:

```
GAGCTCATCT GCAGTGGTGG CGGTGGAAGC GGTGGAAGCG GCGGTGGCAG CAGAAACCTC     60

CCCCTGGCCA TACTAGT                                                   77
```

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 16:

```
    Arg Asn Leu Pro Val Ala
     1               5
```

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE PRIMER"

(xi) SEQUENCE DESCRIPTION: SEQ ID NO: 17:

```
TGCTATCCAG GTTGTGCTAT                                              20
```

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE PRIMER"

(xi) SEQUENCE DESCRIPTION: SEQ ID NO: 18:

```
CTGTGACACC CCTGAAGAAG ATGG                                         24
```

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE PRIMER"

(xi) SEQUENCE DESCRIPTION: SEQ ID NO: 19:

```
ACGCAGAATG TCAGGGAGAA GTAGG                                        25
```

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE PRIMER"

(xi) SEQUENCE DESCRIPTION: SEQ ID NO: 20:

```
TCAGAGGGGA CAACAAGGAG TATG                                         24
```

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "OLIGONUCLEOTIDE PRIMER"

(xi) SEQUENCE DESCRIPTION: SEQ ID NO: 21:

GGAGTGGCCA GGGGGAGGTT TCT                                                    23

(2) INFORMATION FOR SEQ ID NO: 22:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: other nucleic acid
        (A) DESCRIPTION:   /desc = "LINKER DNA"

(xi) SEQUENCE DESCRIPTION: SEQ ID NO: 22:

CATCGATGGC CAGATCTGAT ATCGATG                                                27

(2) INFORMATION FOR SEQ ID NO: 23:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: other nucleic acid
        (A) DESCRIPTION:   /desc = "LINKER DNA"

(xi) SEQUENCE DESCRIPTION: SEQ ID NO: 23:

CATGGTAGCT ACCGGTCTAG ACTATAGCTA CCTAG                                       35

(2) INFORMATION FOR SEQ ID NO: 24:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION:1..5
        (D) OTHER INFORMATION:/note= "THIS SEQUENCE IS REPEATED
          FROM 2 TO 10 TIMES, PREFERABLY FROM 2 TO 5 TIMES, MORE
          PREFERABLY 3 OR 4 TIMES, MOST PREFERABLY 3 TIMES."

(xi) SEQUENCE DESCRIPTION: SEQ ID NO: 24:

Gly Gly Gly Gly Ser
1               5

(2) INFORMATION FOR SEQ ID NO: 25:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION:1..5
        (D) OTHER INFORMATION:/note= "THIS SEQUENCE IS REPEATED
          FROM 2 TO 10 TIMES, PREFERABLY FROM 2 TO 5 TIMES, MORE
          PREFERABLY 3 OR 4 TIMES, MOST PREFERABLY 3 TIMES."

(xi) SEQUENCE DESCRIPTION: SEQ ID NO: 25:

Gly Gly Ser Gly Gly

```
  1               5
```

(2) INFORMATION FOR SEQ ID NO: 26:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION:1..5
        (D) OTHER INFORMATION:/note= "THIS SEQUENCE IS REPEATED
            FROM 2 TO 10 TIMES, PREFERABLY FROM 2 TO 5 TIMES, MORE
            PREFERABLY 3 OR 4 TIMES, MOST PREFERABLY 3 TIMES."

(xi) SEQUENCE DESCRIPTION: SEQ ID NO: 26:

```
Gly Ser Gly Gly Gly
  1               5
```

(2) INFORMATION FOR SEQ ID NO: 27:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION:1..5
        (D) OTHER INFORMATION:/note= "THIS SEQUENCE IS REPEATED
            FROM 2 TO 10 TIMES, PREFERABLY FROM 2 TO 5 TIMES, MORE
            PREFERABLY 3 OR 4 TIMES, MOST PREFERABLY 3 TIMES."

(xi) SEQUENCE DESCRIPTION: SEQ ID NO: 27:

```
Gly Gly Gly Ser Gly
  1               5
```

(2) INFORMATION FOR SEQ ID NO: 28:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO: 28:

```
Thr Phe Arg Gly Asn Val Arg Gly Thr Pro Ile Cys Leu Phe Phe Ile
  1               5                  10                  15

His Ser Asn Met Tyr Pro Leu Met Arg Gln
                 20                  25
```

(2) INFORMATION FOR SEQ ID NO: 29:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 29:

```
Lys Arg Lys Ser Pro Glu Ala Glu Arg Thr Ser
  1               5                  10
```

(2) INFORMATION FOR SEQ ID NO: 30:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 30:

```
Cys Gly Met Cys Val Ser
 1               5
```

(2) INFORMATION FOR SEQ ID NO: 31:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO: 31:

```
Gly Val Glu Ser Pro Gln Ala Pro Gln Gln Ala Glu Val Cys Lys Ala
 1               5                  10                  15

Cys Ile Ser Ile Ser Gln Gln Pro Gly Val Glu Ser Pro Gln Ala Pro
                20                  25                  30

Gln Gln Ala Glu Val Cys Lys Ala Cys Ile Ser Ile Ser Gln Gln Pro
        35                  40                  45
```

(2) INFORMATION FOR SEQ ID NO: 32:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 32:

```
Leu Arg Pro Ser Arg Pro
 1               5
```

(2) INFORMATION FOR SEQ ID NO: 33:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 33:

```
Leu Arg Pro Val Pro Pro Ile Leu Arg Pro Met Ala Asp
 1               5                  10
```

(2) INFORMATION FOR SEQ ID NO: 34:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO: 34:

```
Phe Phe Leu Phe Met Gln Arg Pro Arg Pro Pro Arg Pro Leu Ser Tyr
```

```
                 1               5              10              15
Ser  Arg  Ser  Ser  Glu  Glu  Ala  Phe  Leu  Glu  Ala
                         20                  25
```

(2) INFORMATION FOR SEQ ID NO: 35:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 35:

```
Ala  Phe  Ala  Lys  Ile  Asp  Gln  Glu  Thr  Gly
 1              5                        10
```

(2) INFORMATION FOR SEQ ID NO: 36:

(i) SEQUENCE CHARACTERISTICS:
        (A) LENGTH: 268 amino acids
        (B) TYPE: amino acid
        (D) TOPOLOGY: linear (ii) MOLECULE TYPE: protein (xi) SEQUENCE DESCRIPTION: SEQ ID NO: 36:

```
Gly  Ser  Phe  Arg  Met  Ile  Glu  Gln  Asp  Gly  Leu  His  Ala  Gly  Ser  Pro
 1                   5                       10                      15

Ala  Ala  Trp  Val  Glu  Arg  Leu  Phe  Gly  Tyr  Asp  Trp  Ala  Gln  Gln  Thr
                    20                       25                      30

Ile  Gly  Cys  Ser  Asp  Ala  Ala  Val  Phe  Arg  Leu  Ser  Ala  Gln  Gly  Arg
           35                       40                       45

Pro  Val  Leu  Phe  Val  Lys  Thr  Asp  Leu  Ser  Gly  Ala  Leu  Asn  Glu  Leu
 50                       55                       60

Gln  Asp  Glu  Ala  Ala  Arg  Leu  Ser  Trp  Leu  Ala  Thr  Thr  Gly  Val  Pro
 65                  70                       75                           80

Cys  Ala  Ala  Val  Leu  Asp  Val  Val  Thr  Glu  Ala  Gly  Arg  Asp  Trp  Leu
                     85                       90                           95

Leu  Leu  Gly  Glu  Val  Pro  Gly  Gln  Asp  Leu  Leu  Ser  Ser  His  Leu  Ala
                    100                      105                     110

Pro  Ala  Glu  Lys  Val  Ser  Ile  Met  Ala  Asp  Ala  Met  Arg  Arg  Leu  His
                    115                      120                     125

Thr  Leu  Asp  Pro  Ala  Thr  Cys  Pro  Phe  Asp  His  Gln  Ala  Lys  His  Arg
 130                      135                      140

Ile  Glu  Arg  Ala  Arg  Thr  Arg  Met  Glu  Ala  Gly  Leu  Val  Asp  Gln  Asp
145                      150                      155                     160

Asp  Leu  Asp  Glu  Glu  His  Gln  Gly  Leu  Ala  Pro  Ala  Glu  Leu  Phe  Ala
                         165                      170                     175

Arg  Leu  Lys  Ala  Ser  Met  Pro  Asp  Gly  Glu  Asp  Leu  Val  Val  Thr  His
                    180                      185                     190

Gly  Asp  Ala  Cys  Leu  Pro  Asn  Ile  Met  Val  Glu  Asn  Gly  Arg  Phe  Ser
                    195                      200                     205

Gly  Phe  Ile  Asp  Cys  Gly  Arg  Leu  Gly  Val  Ala  Asp  Arg  Tyr  Gln  Asp
          210                      215                      220

Ile  Ala  Leu  Ala  Thr  Arg  Asp  Ile  Ala  Glu  Glu  Leu  Gly  Gly  Glu  Trp
225                      230                      235                     240

Ala  Asp  Arg  Phe  Leu  Val  Leu  Tyr  Gly  Ile  Ala  Ala  Pro  Asp  Ser  Gln
                         245                      250                     255
```

```
Arg Ile Ala Phe Tyr Arg Leu Leu Asp Glu Phe Phe
        260                 265
```

(2) INFORMATION FOR SEQ ID NO: 37:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 37:

```
Ala Gly Leu Trp Gly Ser Lys
 1           5
```

(2) INFORMATION FOR SEQ ID NO: 38:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO: 38:

```
Pro Thr Lys Arg Arg Pro Thr Cys His His Glu Ile Ser Ile Pro Pro
 1               5                  10                  15
Pro Pro Ser Met Lys Gly Trp Ala Ser Glu Ser Phe Ser Gly Thr Pro
                20                  25                  30
Ala Gly
```

(2) INFORMATION FOR SEQ ID NO: 39:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO: 39:

```
Ser Ser Ser Ala Gly Ile Ser Cys Trp Ser Ser Ser Pro Thr Leu Gly
 1               5                  10                  15
Gly Gly
```

(2) INFORMATION FOR SEQ ID NO: 40:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 40:

```
Leu Lys His Gly Arg Arg Gln Tyr Arg Lys Glu Pro Ala Leu
 1               5                  10
```

(2) INFORMATION FOR SEQ ID NO: 41:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO: 41:

Lys Asp Arg Ile Lys Arg Thr Val Leu Gly Arg Leu Phe Ile Asn Ala
1               5                   10                  15

Gly Phe Gly Pro Arg Ala Gly Thr Leu Ser Ile Pro His Arg Asp Pro
            20                  25                  30

Ile Gly Ala Asn Thr Pro Ala Phe Leu Pro Phe Pro His Pro Thr Pro
        35                  40                  45

Gln Val Arg Val Lys Ala Gln Gly Ser Gln Pro Thr Ser Gly Arg Gln
    50                  55                  60

Ala Leu Pro
65

(2) INFORMATION FOR SEQ ID NO: 42:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 42:

Pro Gln Val Thr His Ile Tyr Phe Arg Leu Ile
1               5                   10

(2) INFORMATION FOR SEQ ID NO: 43:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 43:

Asn Phe Ile Phe Asn Leu Lys Gly Ser Arg
1               5                   10

(2) INFORMATION FOR SEQ ID NO: 44:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:44:

Arg Ser Phe Leu Ile Ile Ser
1               5

(2) INFORMATION FOR SEQ ID NO: 45:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 45:

Pro Lys Ser Leu Asn Val Ser Phe Arg Ser Thr Glu Arg Gln Thr Pro
1               5                   10                  15

(2) INFORMATION FOR SEQ ID NO: 46:

(i) SEQUENCE CHARACTERISTICS:
    (A) LENGTH: 14 amino acids
    (B) TYPE: amino acid
    (D) TOPOLOGY: linear (ii) MOLECULE TYPE: protein (xi) SEQUENCE DESCRIPTION: SEQ ID NO: 46:

Lys Arg Ser Lys Asp Leu Leu Glu Ile Leu Phe Phe Cys Ala
 1               5                  10

(2) INFORMATION FOR SEQ ID NO: 47:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO: 47:

Ser Ala Ala Cys Lys Gln Lys Asn His Arg Tyr Gln Arg Trp Phe Val
 1               5                  10                  15
Cys Arg Ile Lys Ser Tyr Gln Leu Phe Phe Arg Arg
            20                  25

(2) INFORMATION FOR SEQ ID NO: 48:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 48:

Leu Ala Ser Ala Glu Arg Arg Tyr Gln Ile Leu Ser Phe
 1               5                  10

(2) INFORMATION FOR SEQ ID NO: 49:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 49:

Cys Ser Arg Ser (2) INFORMATION FOR SEQ ID NO: 50:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:50:

Ala Thr Thr Ser Arg Thr Leu
 1               5

(2) INFORMATION FOR SEQ ID NO: 51:

(i) SEQUENCE CHARACTERISTICS:
        (A) LENGTH: 8 amino acids
        (B) TYPE: amino acid

```
            (D) TOPOLOGY: linear (ii) MOLECULE TYPE: protein (xi) SEQUENCE DESCRIPTION: SEQ ID NO: 51:

His Arg Leu His Thr Ser Leu Cys
 1               5

(2) INFORMATION FOR SEQ ID NO: 52:

(i) SEQUENCE CHARACTERISTICS:
         (A) LENGTH: 50 amino acids
         (B) TYPE: amino acid
         (D) TOPOLOGY: linear (ii) MOLECULE TYPE: protein (xi) SEQUENCE DESCRIPTION: SEQ ID NO: 52:

Ser Cys Tyr Gln Trp Leu Leu Pro Val Ala Ile Ser Arg Val Leu Pro
 1               5                  10                  15

Gly Trp Thr Gln Asp Asp Ser Tyr Arg Ile Arg Arg Ser Gly Arg Ala
                20                  25                  30

Glu Arg Gly Val Arg Ala His Ser Pro Ala Trp Ser Glu Arg Pro Thr
            35                  40                  45

Pro Asn
    50

(2) INFORMATION FOR SEQ ID NO: 53:

(i) SEQUENCE CHARACTERISTICS:
         (A) LENGTH: 23 amino acids
         (B) TYPE: amino acid
         (D) TOPOLOGY: linear (ii) MOLECULE TYPE: protein (xi) SEQUENCE DESCRIPTION: SEQ ID NO: 53:

Asp Thr Tyr Ser Val Ser Tyr Glu Lys Ala Pro Arg Phe Pro Lys Gly
 1               5                  10                  15

Glu Arg Arg Thr Gly Ile Arg
                20

(2) INFORMATION FOR SEQ ID NO: 54:

(i) SEQUENCE CHARACTERISTICS:
         (A) LENGTH: 88 amino acids
         (B) TYPE: amino acid
         (D) TOPOLOGY: linear (ii) MOLECULE TYPE: protein (xi) SEQUENCE DESCRIPTION: SEQ ID NO: 54:

Ala Ala Gly Ser Glu Gln Glu Ser Ala Arg Gly Ser Phe Gln Gly Glu
 1               5                  10                  15

Thr Pro Gly Ile Phe Ile Val Leu Ser Gly Phe Ala Thr Ser Asp Leu
                20                  25                  30

Ser Val Asp Phe Cys Asp Ala Arg Gln Gly Gly Ala Tyr Gly Lys
            35                  40                  45

Thr Pro Ala Thr Arg Pro Phe Tyr Gly Ser Trp Pro Phe Ala Gly Leu
        50                  55                  60

Leu Leu Thr Cys Ser Phe Leu Arg Tyr Pro Leu Ile Leu Trp Ile Thr
65                  70                  75                  80

Val Leu Pro Pro Cys Ile Ser Tyr
            85
```

(2) INFORMATION FOR SEQ ID NO: 55:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO: 55:

```
Ser Ile Thr Gly Ser Leu Val His Ser Pro Tyr Met Glu Phe Arg Val
 1               5                  10                  15
Thr
```

(2) INFORMATION FOR SEQ ID NO: 56:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 56:

```
Leu Thr Val Asn Gly Pro Pro Gly
 1               5
```

(2) INFORMATION FOR SEQ ID NO: 57:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO: 57:

```
Pro Pro Asn Asp Pro Arg Pro Leu Thr Ser Ile Met Thr Tyr Val Pro
 1               5                  10                  15
Ile Val Thr Pro Ile Gly Thr Phe His
                20                  25
```

(2) INFORMATION FOR SEQ ID NO: 58:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 58:

```
Arg Gln Trp Val Glu Tyr Leu Arg
 1               5
```

(2) INFORMATION FOR SEQ ID NO: 59:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO: 59:

```
Thr Ala His Leu Ala Val His Gln Val Tyr His Met Pro Ser Thr Pro
 1               5                  10                  15
```

```
Pro Ile Asp Val Asn Asp Gly Lys Trp Pro Ala Trp His Tyr Ala Gln
            20                  25                  30

Tyr Met Thr Leu Trp Asp Phe Pro Thr Trp Gln Tyr Ile Tyr Val Leu
        35                  40                  45

Val Ile Ala Ile Thr Met Val Met Arg Phe Trp Gln Tyr Ile Asn Gly
    50                  55                  60

Arg Gly
65
```

(2) INFORMATION FOR SEQ ID NO: 60:

(i) SEQUENCE CHARACTERISTICS:
        (A) LENGTH: 63 amino acids
        (B) TYPE: amino acid
        (D) TOPOLOGY: linear (ii) MOLECULE TYPE: protein (xi) SEQUENCE DESCRIPTION: SEQ ID NO: 60:

```
Arg Phe Asp Ser Arg Gly Phe Pro Ser Leu His Pro Ile Asp Val Asn
1               5                  10                  15

Gly Ser Leu Phe Trp His Gln Asn Gln Arg Asp Phe Pro Lys Cys Arg
            20                  25                  30

Asn Asn Ser Ala Pro Leu Thr Gln Met Gly Gly Arg Arg Val Arg Trp
        35                  40                  45

Glu Val Tyr Ile Ser Arg Ala Gly Leu Val Asn Arg Gln Ile Arg
    50                  55                  60
```

(2) INFORMATION FOR SEQ ID NO: 61:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 61:

```
Lys Ala Arg Ser Leu Gln Thr Val Val Ile Phe Ile Lys Leu
1               5                  10
```

(2) INFORMATION FOR SEQ ID NO: 62:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO: 62:

```
Asn Glu Glu Thr Leu Ile Gly Cys Gly Leu Arg Thr Arg Glu Gly Glu
1               5                  10                  15

Arg Arg Met Gly Leu Leu His Pro His Asp Thr Ser Asp Gln Val Phe
            20                  25                  30

Leu Thr Phe Thr Val Asp Lys Leu Phe Leu Ser Phe His Glu
        35                  40                  45
```

(2) INFORMATION FOR SEQ ID NO: 63:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO: 63:

Ile Ala Lys Lys Gly Gly Ile Leu Leu Leu Phe Thr Leu Glu Ser Thr
1               5                   10                  15

Ser Arg Ala Ala Ala Gly Pro Ser Ile Phe His Pro Gly Gly Val Pro
                20                  25                  30

Gly Lys Cys Thr Gln Phe Ala Leu
                35                  40

(2) INFORMATION FOR SEQ ID NO: 64:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 64:

Val Val Leu Gln Phe Thr Gly Arg Arg Phe Thr Thr Ser
1               5                   10

(2) INFORMATION FOR SEQ ID NO: 65:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 65:

Leu Gly Lys Pro Trp Arg Tyr Pro Thr
1               5

(2) INFORMATION FOR SEQ ID NO: 66:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 66:

Ser Pro Cys Ser Thr Ser Pro Phe Arg Gln Leu Ala
1               5                   10

(2) INFORMATION FOR SEQ ID NO: 67:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO: 67:

Arg Arg Gly Pro His Arg Ser Pro Phe Pro Thr Val Ala Gln Pro Glu
1               5                   10                  15

Trp Arg Met Glu Ile Gln Phe Leu Ser Val
                20                  25

(2) INFORMATION FOR SEQ ID NO: 68:

(i) SEQUENCE CHARACTERISTICS:
    (A) LENGTH: 12 amino acids
    (B) TYPE: amino acid
    (D) TOPOLOGY: linear (ii) MOLECULE TYPE: protein (xi) SEQUENCE DESCRIPTION: SEQ ID NO: 68:

Cys Val Lys Leu Leu Ile Leu Ile Val Cys Val Phe
1               5                   10

(2) INFORMATION FOR SEQ ID NO: 69:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 69:

Ile His Ser Pro Lys Ala His Phe Arg Pro Leu Ser Pro His Ser Leu
1               5                   10                  15

Phe Met Ile Ile Ile Ser His Thr Thr Phe Val Glu Val Leu Leu Ala
            20                  25                  30

Leu Lys Asn Leu Pro His Leu Pro Leu Asn Leu Lys His Lys Met Asn
        35                  40                  45

Ala Ile Val Val Val Asn Leu Phe Ile Ala Ala Tyr Asn Gly Tyr Lys
    50                  55                  60

(2) INFORMATION FOR SEQ ID NO: 70:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO: 70:

Ser Asn Ser Ile Thr Asn Phe Thr Asn Lys Ala Phe Phe Ser Leu His
1               5                   10                  15

Ser Ser Cys Gly Leu Ser Lys Leu Ile Asn Val Ser
            20                  25

(2) INFORMATION FOR SEQ ID NO: 71:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 71:

Arg Val Asn Cys Lys Arg
1               5

(2) INFORMATION FOR SEQ ID NO: 72:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 72:

```
Tyr Phe Val Lys Ile Arg Val Lys Phe Leu Leu Asn Gln Leu Ile Phe
 1               5                  10                  15
```

(2) INFORMATION FOR SEQ ID NO: 73:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 73:

```
Pro Ile Gly Arg Asn Arg Gln Asn Pro Leu
 1               5                  10
```

(2) INFORMATION FOR SEQ ID NO: 74:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO: 74:

```
Ile Lys Arg Ile Asp Arg Asp Arg Val Glu Cys Ser Ser Leu Glu Gln
 1               5                  10                  15

Glu Ser Thr Ile Lys Glu Arg Gly Leu Gln Arg Gln Arg Ala Lys Asn
                20                  25                  30

Arg Leu Ser Gly Arg Trp Pro Thr Thr
                35                  40
```

(2) INFORMATION FOR SEQ ID NO: 75:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 75:

```
Thr Ile Thr Leu Ile Lys Phe Phe Gly Val Glu Val Pro
 1               5                  10
```

(2) INFORMATION FOR SEQ ID NO: 76:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 76:

```
Ser Thr Lys Ser Glu Pro
 1               5
```

(2) INFORMATION FOR SEQ ID NO: 77:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 77:

Arg Glu Pro Pro Ile
 1               5

(2) INFORMATION FOR SEQ ID NO: 78:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO: 78:

Ser Leu Thr Gly Lys Ala Gly Glu Arg Gly Glu Lys Gly Arg Glu Glu
 1               5                  10                  15

Ser Glu Arg Ser Gly Arg
                20

(2) INFORMATION FOR SEQ ID NO: 79:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO: 79:

Gly Ala Gly Lys Cys Ser Gly His Ala Ala Arg Asn His His Thr Arg
 1               5                  10                  15

Arg Ala (2) INFORMATION FOR SEQ ID NO: 80:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 80:

Cys Ala Ala Thr Gly Arg Val Arg
 1               5